United States Patent [19]

Bouboutou et al.

[11] Patent Number: 5,468,888
[45] Date of Patent: Nov. 21, 1995

[54] LUPANE DERIVATIVES, THEIR PREPARATION AND THE PHARMACEUTICAL COMPOSITIONS WHICH CONTAIN THEM

[75] Inventors: Romaine Bouboutou, Arcueil; Norbert Dereu, Viry Chatillon, both of France; Michel Evers, Liège, Belgium; Jean-Christophe Gueguen, Saint-Cloud, France; Claude James, Lesigny, France; Christèle Poujade, Joinville, France; Daniel Reisdorf; Yves Ribeill, both of Thiais, France; Françoise Soler, Paris, France

[73] Assignee: Rhone-Poulenc Rorer S.A., Antony Cedex, France

[21] Appl. No.: 243,341

[22] Filed: May 12, 1994

[51] Int. Cl.⁶ .................................................. C07C 233/80
[52] U.S. Cl. ................ 554/58; 554/502; 554/35; 554/51; 554/54; 554/57; 554/59; 554/61; 554/63
[58] Field of Search ................ 554/55, 51, 57, 554/56, 58, 59, 61, 63, 502, 169, 120

Primary Examiner—José G. Dees
Assistant Examiner—Deborah D. Carr
Attorney, Agent, or Firm—James A. Nicholson; Raymond S. Parker, III; Martin F. Savitzky

[57] ABSTRACT

The present invention relates to new lupane derivatives of the general formula:

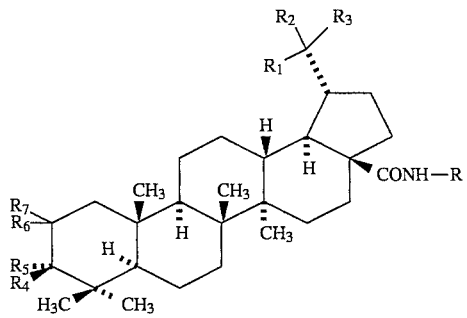

to their salts, to their preparation and to the pharmaceutical compositions which contain them.

8 Claims, No Drawings

LUPANE DERIVATIVES, THEIR PREPARATION AND THE PHARMACEUTICAL COMPOSITIONS WHICH CONTAIN THEM

The present invention relates to new lupane derivatives of general formula:

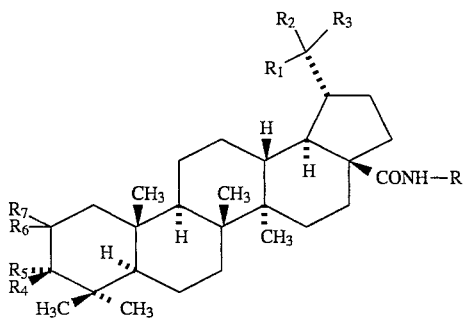

to their salts, to their preparation and to the pharmaceutical compositions which contain them.

Japanese Patent Application J 01,143,832 described betulin derivatives of general formula:

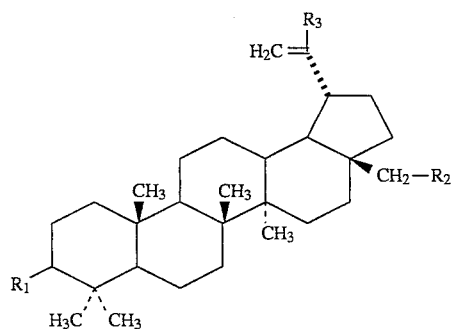

in which $R_1$ and $R_2$ are hydroxyl or acyloxy and $R_3$ is, in particular, methyl. These derivatives are useful in the anti-cancer field.

It has now been found that the lupane derivatives of general formula (I) in which:
R represents a radical of general formula:

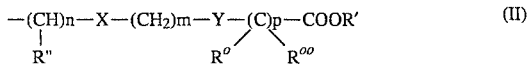

in which R' and R", which are identical or different, are hydrogen atoms or alkyl radicals, X is a bond or represents a carbamoyl, N-methylcarbamoyl, aminocarbonyl or N-methylaminocarbonyl radical, Y is a bond or represents a phenylene radical, $R^o$ and $R^{oo}$, which are identical or different, are hydrogen atoms or alkyl radicals (it being understood that $R^o$ and $R^{oo}$ are not necessarily identical on each unit —$CR^oR^{oo}$—), or $R^o$ is hydroxyl, hydroxyalkyl, phenyl, benzyl, carbamoylmethyl or else, when Y is a bond and X is carbamoyl, $R^o$ can form a 5- or 6-membered ring with the nitrogen atom contained in X, it being possible for this ring to additionally comprise another hetero atom chosen from oxygen or sulphur and, n, m and p are integers from 0 to 16 such that m+n+p is between 4 and 16, $R_1$ is a methyl radical, or forms with $R_3$ a methylene radical or an oxo radical, $R_2$ is a hydroxyl, methyl or hydroxymethyl radical or a radical —$CH_2OR'_2$, —$CH_2SR'_2$ or —$CH_2NHR'_2$ for which $R'_2$ is alkyl, hydroxyalkyl, dihydroxyalkyl, acetamidoalkyl or acetyl, or $R_2$ is an amino radical substituted with a hydroxyalkyl or carboxyhydroxyalkyl radical, or a dialkylamino radical, the alkyl parts of which can form, with the nitrogen atom to which they are joined, a 5- or 6-membered heterocycle optionally containing another hetero atom chosen from oxygen, sulphur or nitrogen and, optionally, N-alkyl, $R_3$ is a hydrogen atom or forms, with $R_1$ or $R_2$, a methylene radical or an oxo radical, $R_4$ and $R_5$ are different and represent a hydrogen atom or a hydroxyl radical, or together form an oxo, hydroxyimino or optionally substituted (with a carboxyl or dialkylamino radical, the alkyl parts of which can form, with the nitrogen atom to which they are joined, a 5- or 6-membered heterocycle optionally containing another hetero atom chosen from oxygen, nitrogen or sulphur and optionally substituted with an alkyl radical) alkyloxyimino radical and $R_6$ and $R_7$ are hydrogen atoms, or else $R_4$ and $R_5$, and $R_6$ and $R_7$, together form oxo radicals, as well as their pharmaceutically acceptable salts, when they exist, display a cytoprotecting effect for cells infected with an HIV virus (Human Immunodeficiency Virus) as well as an inhibitory activity on the production of reverse transcriptase in an HIV virus.

In the general formula above, it is understood that the alkyl radicals are straight or branched and contain 1 to 4 carbon atoms.

According to the invention, the products of general formula (I) can be obtained by reacting an amino acid of general formula:

$$H_2N—R \qquad (III)$$

in which R is defined as above and, if appropriate, the acidic functional group of which was protected beforehand, with the chloride of the acid of general formula:

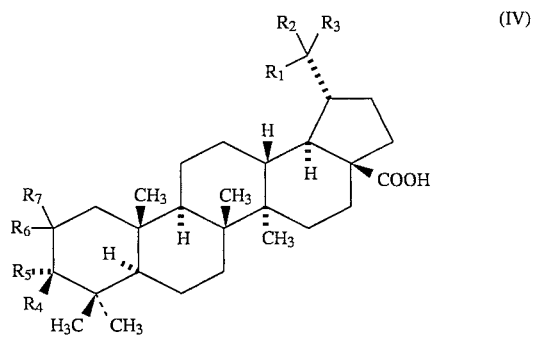

in which $R_1$, $R_2$, $R_3$, $R_4$, $R_5$, $R_6$ and $R_7$ are defined as above, followed, if appropriate, by the conversion to an ester for which the symbol R' is alkyl and then by the removal of the protecting groups.

It is understood that when $R_2$, $R_4$ or $R_5$ represent or contain a hydroxyl radical, the latter is protected beforehand; this is likewise the case if $R_2$ contains a carboxyl radical or if the substituent —$CR_1R_2R_3$ in position 19 is a carboxyl radical.

The reaction of the amino acid with the chloride of the 20(29)-lupen-28-oic acid of general formula (IV) is carried out according to conventional methods which do not change the rest of the molecule. The reaction is, in particular, carried out in the presence of a nitrogenous organic base such as a trialkylamine (triethylamine, for example) in an organic solvent such as a chlorinated solvent (chloroform, 1,2-dichloroethane, dichloromethane) or in tetrahydrofuran or in a mixture of these solvents, at a temperature between 15° and 30° C.

The acidic functional group of the amino acid of general formula (III) is protected by any compatible radical which can be introduced and removed without changing the rest of the molecule. Likewise, the radicals $R_2$, $R_4$ or $R_5$ of the lupane derivative of general formula (IV) are protected by compatible radicals which can be introduced and removed without affecting the rest of the molecule. The protecting groups can be chosen, for example, from the radicals described by T. W. Greene, Protective Groups in Organic Synthesis, J. Wiley-Interscience Publications (1991) or by McOmie, Protective Groups in Organic Chemistry, Plenum Press (1973). It is in particular advantageous to use protecting groups which can be simultaneously removed. Radicals will be chosen which can be removed in neutral, basic or acidic medium. Protections can be advantageously carried out in the form of esters. In this case, removal of the protecting groups is carried out by hydrolysis in basic medium, in particular in the presence of sodium hydroxide solution at a temperature of between 10° and 50° C.

For example, hydroxyl radicals can be protected as esters (formyloxy, acetoxy, i-butoxy, trichloroacetyloxy, phenoxyacetyloxy or benzyloxy), as ketones, in the carbonate form with a radical —COOR$_a$ in which R$_a$ is an optionally substituted alkyl or benzyl radical or even with a trialkylsilyl radical; the acid protecting groups can be chosen from alkyl radicals (methyl, ethyl or t-butyl), substituted alkyl (trichloroethyl, haloethyl, p-toluenesulphonylethyl, benzyl, benzyl substituted with a nitro radical, benzhydryl, triphenylmethyl, benzyloxymethyl and the like), alkyloxyalkyl (methoxymethyl), tetrahydropyranyl or trimethylsilyl.

Lupane derivatives of general formula (I) in which the radical R has a chiral centre exhibit isomeric forms. It is understood that these isomeric forms and their mixtures come within the scope of the present invention. The preparation of one or the other of these forms depends on the choice of starting amino acid.

If appropriate, the conversion to an ester for which R' is an alkyl radical is carried out according to conventional methods which do not change the rest of the molecule. In particular, the conversion is performed by reacting with an alkyl iodide.

According to the invention, the lupane derivative of general formula (I) for which $R_4$ and $R_5$ together form a hydroxyimino or optionally substituted alkyloxyimino radical as defined above, and the other radicals are defined as above, can also be obtained by reacting hydroxylamine or one of its derivatives of general formula:

$$R_8\text{—O—NH}_2 \qquad (V)$$

in which $R_8$ is a hydrogen atom or an optionally substituted (with a carboxyl radical or dialkylamino radical, the alkyl parts of which can form, with the nitrogen atom to which they are joined, a 5- or 6-membered heterocycle optionally containing another hetero atom chosen from oxygen, nitrogen or sulphur and optionally substituted with an alkyl radical) alkyl radical, with the lupane derivative of general formula (I) in which $R_4$ and $R_5$ together form an oxo radical and then, if appropriate, by releasing from the protecting groups.

It is understood that if $R_8$ contains a carboxyl radical or if the lupane derivative of general formula (I) contains carboxyl or hydroxyl radicals, the latter are protected beforehand. The protection and the release of the protecting groups is carried out according to the methods mentioned above.

Reaction is advantageously carried out from the hydrochloride of the derivative of general formula (V) in pyridine at the reflux temperature of the reaction mixture, or in an alcohol in the presence of an alkali metal carbonate at the reflux temperature of the reaction mixture.

According to the invention, the lupane derivative of general formula (I) for which $R_1$ and $R_2$ are methyl radicals, $R_3$ is a hydrogen atom and the other radicals are defined as above can also be obtained by reduction of a lupane derivative of general formula (I) for which $R_1$ and $R_3$ together form a methylene radical and $R_2$ is defined as above.

Reduction is carried out by any known method which does not affect the rest of the molecule. In particular, the reduction is carried out by catalytic hydrogenation in the presence of palladium-on-charcoal, at atmospheric pressure, at a temperature of between 15° and 25° C. in a solvent such as an alcohol (methanol or ethanol, for example).

If appropriate, radicals capable of interfering with the reaction are protected beforehand. Protection and removal of the protecting groups is carried out according to the methods mentioned above.

According to the invention, the lupane derivative of general formula (I) for which $R_2$ is a hydroxyl radical, $R_1$ is a methyl radical, $R_3$ is a hydrogen atom and the other radicals are defined as above can also be obtained by reduction of a lupane derivative of general formula (I) for which $R_2$ and $R_3$ together form an oxo radical and $R_1$ is a methyl radical.

Reduction is carried out by any known method which does not affect the rest of the molecule. In particular, reduction is carried out with an alkali metal borohydride (sodium borohydride, for example) in the presence of tetrabutylammonium or tetraethylammonium chloride, in a solvent such as an aromatic hydrocarbon (toluene, for example), at a temperature of between 50° C. and the reflux temperature of the reaction mixture.

If appropriate, radicals capable of interfering with the reaction are protected beforehand. Protection and removal of the protecting groups is carried out according to the methods mentioned above.

According to the invention the lupane derivative of general formula (I) for which $R_1$ and $R_3$ together form an oxo radical, $R_2$ is a hydroxyl radical and the other radicals are as defined above can also be obtained by oxidation of a lupane derivative of general formula (I) for which $R_1$ and $R_3$ together form an oxo radical and $R_2$ is a methyl radical.

Reaction is generally carried out by the action of a hypochlorite or a hypobromite; for example, by the action of sodium hypobromite which can be prepared in situ, in aqueous/organic medium, especially in dioxane, at a temperature of between −10° and 20° C.

If appropriate, radicals capable of interfering with the reaction are protected beforehand. Protection and removal of the protecting groups is carried out according to the methods mentioned above.

According to the invention, the lupane derivative of general formula (I) for which X (in radical R) represents a carbamoyl radical and the other radicals are defined as above can also be obtained from a lupane derivative of general formula:

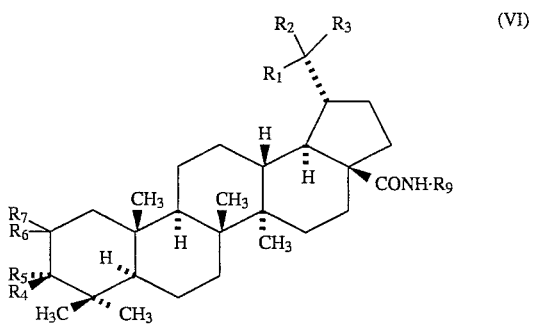

in which $R_1$, $R_2$, $R_3$, $R_4$, $R_5$, $R_6$ and $R_7$ are defined as above and $R_9$ represents a radical of general formula

in which n and R" are defined as above, by reacting with an amine of general formula:

in which R', $R^o$, $R^{oo}$, m and p are defined as above, then, if appropriate, by converting the acid obtained to an ester for which R' is an alkyl radical and, if appropriate, by removing the protecting groups.

It is understood that radicals representing or containing radicals which can interfere with the reaction are protected beforehand. Protection and release of the protecting groups is carried out as described above.

The condensation of the amine of general formula (VIII) is preferably carried out from the hydrochloride of the amine. The reaction is carried out according to the conventional methods for condensing an amine with an acid. In particular, the condensation is carried out in the presence of an acid acceptor such as a nitrogenous organic base (trialkylamine, pyridine, N-methylmorpholine, 1,8-diazabicyclo[5.4.0]undec-7-ene or 1,5-diazabicyclo[4.3.0]non-5-ene, for example) in an organic solvent such as a chlorinated solvent (dichloromethane, dichloroethane or chloroform, for example) or an amide (dimethylformamide, for example). It is also possible to carry out the condensation in the presence of a condensing agent such as a carbodiimide (dicyclohexylcarbodiimide or 1-(3-dimethylaminopropyl)-3-ethylcarbodiimide hydrochloride, for example) and optionally in the presence of a catalyst such as N-hydroxybenzotriazole or N-hydroxysuccinimide, at a temperature of between −20° and 40° C.

The amino acid of general formula (III) and the lupane derivative of general formula (IV) can be prepared as described below in the Examples.

In particular, lupane derivatives of general formula (IV) for which $R_1$ is a methyl radical, $R_2$ is a hydroxyl or methyl radical and $R_3$ is a hydrogen atom can be prepared according to the reduction process described above for the preparation of products of general formula (I) for which $R_2$ is a hydroxyl radical.

Lupane derivatives of general formula (IV) for which $R_1$ is a methyl radical and $R_2$ and $R_3$ together form an oxo radical can be prepared according to the method described by A. Vystrcil et al., Collect. Czech. Chem. Comm., 35, 295 (1970).

Lupane derivatives of general formula (IV) for which $R_2$ is a hydroxyl radical and $R_1$ and $R_3$ together form an oxo radical can be prepared by analogy with the method described for the preparation of the corresponding products of general formula (I), by oxidation of the corresponding methyl ketone. It is understood that protection of the acid thus obtained in position 19 is indispensable for use in the following reaction.

Lupane derivatives of general formula (IV) for which $R_2$ is a hydroxymethyl radical can be prepared by reacting silver acetate with the corresponding brominated derivative for which $R_2$ is bromomethyl and for which, if necessary, the radical $R_4$ or $R_5$ is protected beforehand. The reaction is advantageously carried out in an organic solvent such as, for example, toluene, at a temperature between 20° C. and the reflux temperature of the reaction mixture. The starting brominated derivative can be obtained by reacting a brominating agent, such as, for example, tetrabutylammonium tribromide or N-bromosuccinimide, with the corresponding derivative of 20(29)-lupen-28-oic acid. Reaction is carried out in a chlorinated solvent such as methylene chloride, chloroform or carbon tetrachloride at a temperature in the region of 25° C.

Lupane derivatives of general formula (IV) for which $R_2$ is a substituted amino radical and $R_1$ and $R_3$ together form an oxo radical can be prepared by reacting the corresponding amine with the lupane derivative of general formula (IV) for which $R_2$ is a hydroxyl radical and $R_1$ and $R_3$ together form a oxo radical. The reaction is carried out by any known method to obtain an amide from an acid without affecting the rest of the molecule. The preparation is carried out in particular by reacting the amine with the chloride of the acid of general formula (IV) in a chlorinated solvent at a temperature of between −20° and 40° C. It is understood that functional groups which can interfere with the reaction are protected beforehand; in particular, when the substituted amino radical is a carboxyhydroxyalkyl radical, it is necessary to protect the carboxyl radical.

Lupane derivatives of general formula (IV) for which $R_2$ is a substituted amino radical and $R_1$ and $R_3$ together form an oxo radical can be prepared by reacting the corresponding amine with the lupane derivative for which $R_2$ is a bromomethyl radical in the presence of tetra[triphenylphosphine] palladium and a nitrogenous base.

Lupane derivatives of general formula (IV) for which $R_2$ is a radical $-CH_2OR'_2$ or $-CH_2SR'_2$ and $R_1$ and $R_3$ together form a methylene radical can be prepared from the lupane derivative for which $R_2$ is bromomethyl by the action of the corresponding alkoxide or thiolate.

3α-Hydroxy-20(29)-lupen-28-oic acid (3α-betulinic acid) and its derivatives which are substituted in position 20 or 30 can be obtained according to or by analogy with the method described by W. Herz, Phytochemistry, 11, 3061 (1972).

Lupane derivatives of general formula (IV) for which $R_4$ and $R_5$ together form an oxo radical can be prepared by oxidation of the lupane derivative of general formula (IV) for which $R_4$ and $R_5$ respectively represent a hydrogen atom and hydroxyl radical. Oxidation is advantageously carried out with an oxidising agent such as chromic anhydride.

Lupane derivatives of general formula (IV) for which $R_4$ and $R_5$, and $R_6$ and $R_7$, together form oxo radicals can be prepared by oxidation of the lupane derivative of general formula (IV) for which $R_4$ and $R_5$ together form an oxo radical.

Lupane derivatives of general formula (IV) for which $R_4$ and $R_5$ together form a hydroxyimino or optionally substituted (with a carboxyl radical or dialkylamino radical, the alkyl parts of which can form, with the nitrogen atom to which they are joined, a 5- or 6-membered heterocycle optionally containing another hetero atom chosen from oxygen, nitrogen or sulphur and optionally substituted with an alkyl radical) alkyloxyimino radical can be prepared by analogy with the process described above for the preparation of lupane derivatives of general formula (I) for which $R_4$ and $R_5$ together form a radical =N—O—$R_8$.

The acid chloride of the lupane derivative of general formula (IV) can be prepared according to known methods. For example, the preparation is carried out by reaction of oxalyl chloride or thionyl chloride in a chlorinated solvent such as chloroform, dichloroethane or dichloromethane.

Lupane derivatives of general formula (VI) can be prepared by analogy with the method described for the preparation of products of general formula (I), from a product of general formula (IV).

The products of general formula (VIII) can be prepared according to or by analogy with the methods described below in the Examples.

The novel lupane derivatives of general formula (I) can be purified, if appropriate, by physical methods such as crystallisation or chromatography.

The products according to the invention can be converted to metal salts or to addition salts with a nitrogenous base according to methods known per se. These salts can be obtained by reacting a metal base (for example, alkali metal or alkaline-earth metal), aqueous ammonia or an amine with a product according to the invention in a suitable solvent such as water or an alcohol. The salt formed precipitates after optional concentration of the solution; it is separated by filtration.

There can be mentioned, as examples of pharmaceutically acceptable salts, the salts with alkali metals (sodium, potassium or lithium) or with alkaline-earth metals (magnesium or calcium), the ammonium salt, the salts of nitrogenous bases (ethanolamine, diethanolamine, trimethylamine, triethylamine, methylamine, propylamine, diisopropylamine, N,N-dimethylethanolamine, benzylamine, dicyclohexylamine, N-benzylphenethylamine, N,N'-dibenzylethylenediamine, diphenylenediamine, benzhydrylamine, quinine, choline, arginine, lysine, leucine or dibenzylamine).

The novel lupane derivatives according to the present invention are particularly useful for the prophylaxis and the treatment of AIDS (Acquired Immune Deficiency Syndrome) and associated syndromes [ARC (AIDS-related complex)]. Prophylaxis implies the treatment of subjects who have been exposed to the HIV viruses, in particular asymptomatic seropositives who risk developing the disease in the months or years to come after primary infection.

The products according to the invention, which are inhibitors of the cytopathogenic effect of HIV and inhibitors of the production of reverse transcriptase in cell cultures at concentrations which are devoid of cytotoxic or cytostatic effects, are particularly advantageous.

The activities were revealed in the following tests:

Activity with Respect to the Cytopathogenic Effect of the HIV Virus

The products, as powders, were dissolved at a concentration of 2 mg of product per 2 ml (approximately $4 \times 10^{-3}$M) in a mixture of dimethylformamide (DMF) and L-lysine (base) at 1:19 (vol:vol). 1 volume of DMF is first added and the product is solubilised as much as possible and then 9 volumes of a $4 \times 10^{-3}$M solution of L-lysine base in distilled water are added. In this way, a 10% stock solution of product in DMF is obtained which contains a molar ratio (product/ lysine) close to 1. The test is carried out on the CEM clone 13 lymphoblastoid line. 25 µl/well of a solution of product to be tested in isotonic phosphate buffer (IPB), or IPB alone in the case of the controls, are placed in a 96-well microplate. The products were studied at various concentrations (often 8), at the rate of 6 wells per concentration. 125 µl of a suspension of CEM cells ($8 \times 10^4$ cells per ml) in RPMI medium containing 10% of foetal calf serum, 100 IU/ml of penicillin, 100 µg/ml of streptomycin and 2 µmoles/ml of glutamine are then added and the microplates are incubated for one hour at 37° C. under an atmosphere containing 5% carbon dioxide. For each concentration, the testing is divided into two parts: one part (3 wells) on infected cells, for determination of the antiviral activity, and the other part (3 wells) on uninfected cells, to determine the cytotoxicity of the products. The first series is then infected with HIV-1 (100 µl per well of a suspension of LAV-1-BRU virus containing 200–300 $TCID_{50}$) while the other series receives 100 µl of RPMI medium as defined above. After incubating for 7 days, 100 µl of cells are withdrawn in order to measure the cell viability [determined following a modification of the technique described by R. Pauwels et al., J. Virol. Meth., 20, 309–321 (1988)]. 10 µl of a solution containing 7 mg of MTT [3-(4,5-dimethyl-2-thiazolyl)-2,5-diphenyltetrazolium bromide] per ml of isotonic phosphate buffer are added to this withdrawn sample. After incubating for 3 hours at 37° C., the supernatant liquid is removed. The MTT is converted to a salt of formazan (blue) solely inside living cells. 100 µl of isopropanol (containing 0.04 mol/l of hydrochloric acid) are then added and the microplates are agitated until the formazan blue has dissolved. The absorbance at 540 nm is read with an automatic reader for ELISA reactions in microplates. This absorbance is proportional to the quantity of living cells.

The degree of protection (in %) of a given product is determined from the optical densities (OD) by the formula:

$$\frac{OD \text{ (treated and inf. cells)} - OD \text{ (untreated and inf. cells)}}{OD \text{ (treated and uninf. cells)} - OD \text{ (untreated and inf. cells)}}$$

If appropriate, the 50% inhibitory concentration is determined.

The results show that for concentrations of tested product of between 0.5 and 30 µg/ml, a significant reduction in the cytopathogenic effect is obtained.

The degree of protection provided by the products according to the invention is of between 20 and 100%.

The 50% inhibitory concentration of the products according to the invention is of between 0.30 and 100 µg/ml when it can be determined.

Determination of the Viral Multiplication per Measured Charge of the Reverse Transcriptase of the HIV Virus The activity of the reverse transcriptase is measured directly on 50 µl of culture supernatant liquid. According to the method described by O. Schwartz et al., AIDS Research and Human Retrovirus 4(6), 441–448 (1988), 10 µl of buffer containing 0.5M of KCl, 5 mM of dithiothreitol (DTT) and 0.5% of Triton X-100 are added to all the microwells containing 50 µl samples of supernatant liquid to be tested. 40 µl of buffer containing 1.25 mM of ethylene glycol bis(2-aminoethyl ether)tetraacetic acid (EGTA), 0.125 mM of Tris.HCl pH 7.8, 12.5 mM of $MgCl_2$, 3 µCi of ($^3$H)thymidine triphosphate (TTP) and 0.05 OD$_{260}$ of polyadenylic acid - thymidylic acid (poly rA-oligo dT) are then added. The microplate is covered with a plastic film and incubated for 60 minutes at 37° C.

The reaction is stopped by adding 20 µl of an ice-cold solution of 120 mM of Na$_4$P$_2$O$_7$ in 60% trichloroacetic acid and the samples are placed for 15 minutes on the ice bed.

The precipitates are filtered on glass fibres by using a cell washer (Skatron) and the filters are washed with a solution of 12 mM of Na$_4$P$_2$O$_7$ in 5% trichloroacetic acid.

The filters are dried and the radioactivity is counted after addition of a scintillating liquid.

Inhibitions of the reverse transcriptase production associated with the virus are observed of between 20 and 100% at the concentrations tested (0.30 to 100 µg/ml).

Of particular interest are the products of general formula (I) in which:
R represents a radical of general formula:

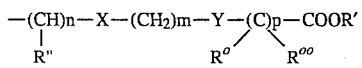

in which R' and R", which are identical or different, are hydrogen atoms or alkyl radicals, X is a bond or represents a carbamoyl, N-methylcarbamoyl or aminocarbonyl radical, Y is a bond or represents a phenylene radical, $R^o$ and $R^{oo}$, which are identical or different, are hydrogen atoms or alkyl radicals (it being understood that $R^o$ and $R^{oo}$ are not necessarily identical on each unit —$CR^oR^{oo}$—), or $R^o$ is hydroxyl, hydroxyalkyl, phenyl, benzyl, carbamoylmethyl or else, when Y is a bond and X is carbamoyl, $R^o$ can form a 5- or 6-membered ring with the nitrogen atom contained in X and, n, m and p are integers from 0 to 16 such that m+n+p is between 4 and 16, R$_1$ is a methyl radical, or forms, with R$_3$, a methylene radical or an oxo radical, R$_2$ is a hydroxyl, methyl or hydroxymethyl radical or a radical —CH$_2$SR'$_2$ or —CH$_2$NHR'$_2$ for which R'$_2$ is alkyl, hydroxyalkyl, acetamidoalkyl or acetyl, or R$_2$ is an amino radical substituted with a hydroxyalkyl or carboxyhydroxyalkyl radical, or a dialkylamino radical, the alkyl parts of which can form, with the nitrogen atom to which they are joined, a 5- or 6-membered heterocycle optionally containing another nitrogen atom and optionally N-methylated, R$_3$ is a hydrogen atom or forms, with R$_1$ or R$_2$, a methylene radical or an oxo radical, R$_4$ and R$_5$ are different and represent a hydrogen atom or a hydroxyl radical, or together form an oxo, or optionally substituted (with a carboxyl or dialkylamino radical, the alkyl parts of which can form, with the nitrogen atom to which they are joined, a 5- or 6-membered heterocycle optionally containing another nitrogen atom optionally substituted with a methyl radical) alkyloxyimino radical and R$_6$ and R$_7$ are hydrogen atoms, or else R$_4$ and R$_5$, and R$_6$ and R$_7$, together form oxo radicals, it being understood that the alkyl radicals are straight or branched and contain 1 to 4 carbon atoms, as well as their salts when they exist.

And among these products, the following are more especially active:

N'-[N-[3β-Hydroxy-20(29)-lupen-28-oyl]-8-aminooctanoyl]-β-alanine;

N'-[N-[3β-Hydroxy-20(29)-lupen-28-oyl]-8-aminooctanoyl]-L-alanine;

N'-[N-[3β-Hydroxy-20(29)-lupen-28-oyl]-8-aminooctanoyl]-L-threonine;

N'-[N-[3β-Hydroxy-20(29)-lupen-28-oyl]-8-aminooctanoyl]-L-statine;

N-[3β-Hydroxy-20(29)-lupen-28-oyl]-7-aminoheptylcarbamoylacetic acid.

The following examples, given as non-limiting, illustrate the present invention.

EXAMPLE 1

650 mg of methyl 5-aminopentanoate hydrochloride and then 1.07 cm$^3$ of triethylamine are added to 50 cm3 of a chloroform solution of 3β-acetoxy-20(29)-lupen-28-oyl chloride (prepared from 1.7 g of 3β-acetoxy-20(29)-lupen-28-oic acid). The solution is then stirred for 20 hours at a temperature in the region of 20° C. After addition of 60 cm$^3$ of distilled water, the organic phase is separated off and the aqueous phase is washed with a total of 40 cm$^3$ of chloroform. The combined organic phases are washed with a total of 40 cm$^3$ of distilled water, dried over anhydrous sodium sulphate and concentrated to dryness under reduced pressure (2.7 kPa) at a temperature in the region of 40° C. 1.9 g of a yellow foam is obtained which is chromatographed on a column with a diameter of 2.2 cm containing 38 g of silica.(0.02–0.045 mm) eluted with diisopropyl ether while collecting 10 cm$^3$ fractions. After discarding the first 23 fractions, the following 17 are combined and concentrated under reduced pressure (2.7 kPa) at a temperature in the region of 40° C. 1.1 g of methyl N-[3β-acetoxy-20(29)-lupen-28-oyl]-5-aminopentanoate is thus obtained in the form of a white foam (R$_f$=0.35; silica thin film chromatography; eluent: diisopropyl ether).

18 cm$^3$ of 4N sodium hydroxide solution are added to a solution of 1.1 g of methyl N-[3β-acetoxy-20(29)-lupen-28-oyl]-5-aminopentanoate in 18 cm$^3$ of methanol and 9 cm$^3$ of tetrahydrofuran and the reaction mixture is stirred for 15 hours at a temperature in the region of 20° C. The mixture is diluted with 40 cm$^3$ of distilled water and stirred again for approximately 15 minutes. The suspension is then acidified to a pH in the region of 2 using 21 cm$^3$ of 4N hydrochloric acid. After stirring for 1 hour, the solid is separated by filtration, washed 5 times with a total of 100 cm$^3$ of distilled water until the chloride ions have been removed (silver nitrate test) and dried under reduced pressure (13.5 Pa) at a temperature in the region of 20° C. 820 mg of N-[3β-hydroxy-20(29)-lupen-28-oyl]-5-aminopentanoic acid are thus obtained in the form of a white foam melting around 160° C.

3β-Acetoxy-20(29)-lupen-28-oyl chloride is prepared according to J. Provita and A. Vystrcil, Collect. Czech. Chem. Commun., 41, 1200 (1976).

EXAMPLE 2

0.53 cm$^3$ of triethylamine and 380 mg of methyl 6-aminohexanoate hydrochloride are added to a solution of 1 g of 3β-acetoxy-20(29)-lupen-28-oyl chloride in solution in 50 cm$^3$ of methylene chloride, stirring is maintained for 20 hours at a temperature in the region of 20° C. and then 100 cm$^3$ of distilled water are added. The organic phase is separated off, the aqueous phase is extracted with a total of 75 cm$^3$ of methylene chloride, the organic extracts are combined, dried over anhydrous magnesium sulphate and concentrated to dryness under reduced pressure (2.7 kPa) at a temperature in the region of 40° C. The residue obtained is purified by HPLC with fractions of 250 mg, on a column with a diameter of 5 cm containing 200 g of $C_{18}$-grafted silica (0.01 mm) eluted with a 75/10/15 (by volume) mixture of acetonitrile, water and tetrahydrofuran while collecting 75 cm³ fractions. The first 3 fractions are discarded; the following 2 are combined and concentrated under reduced pressure (13.5 Pa) at a temperature in the region of 35° C. 838 mg of methyl N-[3β-acetoxy-20(29)-lupen-28-oyl]-6-aminohexanoate are thus obtained in the form of a white foam [$R_f$=0.3; silica thin layer chromatography; eluent: cyclohexane/ethyl acetate (80-20 by volume)].

A solution of 800 mg of methyl N-[3β-acetoxy-20(29)-lupen-28-oyl]-6-aminohexanoate in 13 cm³ of methanol, 6.5 cm³ of tetrahydrofuran and 1.6 cm³ of 4N sodium hydroxide solution is stirred for 15 hours at a temperature in the region of 20° C. After addition of 2 cm³ of 5N hydrochloric acid and 20 cm³ of distilled water, stirring is maintained for 30 minutes. The solid is separated by filtration, washed with a total of 50 cm³ of distilled water and dried in air. 750 mg of N-[3β-hydroxy-20(29)-lupen-28-oyl]-6-aminohexanoic acid are thus obtained in the form of a white solid, melting around 135° C.

EXAMPLE 3

320 mg of methyl 7-aminoheptanoate hydrochloride and then 0.62 cm³ of triethylamine are added to a solution of 1 g of 3β-acetoxy-20(29)-lupen-28-oyl chloride in 30 cm³ of dichloromethane. The solution is stirred for 20 hours at a temperature in the region of 20° C. and the solvent is evaporated to dryness under reduced pressure (2.7 kPa) at a temperature in the region of 40° C. The 1.77 g of beige foam obtained are chromatographed on a column with a diameter of 3 cm containing 80 g of silica (0.02–0.045 mm) eluted with an 80/20 (by volume) mixture of cyclohexane and ethyl acetate while collecting 60 cm³ fractions. The first 23 fractions are discarded; the following 8 are combined and concentrated under reduced pressure (2.7 kPa) at a temperature in the region of 30° C. 930 mg of methyl N-[3β-acetoxy-20(29)-lupen-28-oyl]-7-aminoheptanoate are thus obtained in the form of a white foam. [$R_f$=0.2; silica thin layer chromatography; eluent: cyclohexane/ethyl acetate 80/20 (by volume)].

1.9 cm³ of 7N sodium hydroxide solution is added over approximately 5 minutes to a solution of 930 mg of methyl N-[3β-acetoxy-20(29)-lupen-28-oyl]-7-aminoheptanoate in 7 cm³ of methanol and 10 cm³ of tetrahydrofuran and the reaction mixture is stirred for 15 hours at a temperature in the region of 20° C. and the solvent is evaporated to dryness under reduced pressure (2.7 kPa) at a temperature in the region of 30° C. The residue is diluted in 40 cm³ of distilled water and acidified to a pH in the region of 2 using 5N hydrochloric acid. After stirring for 20 minutes, the solid is separated by filtration, washed with a total of 100 cm³ of distilled water and dried under reduced pressure (13.5 Pa) at a temperature in the region of 20° C. 740 mg of N-[3β-hydroxy-20(29)-lupen-28-oyl]-7-aminoheptanoic acid are thus obtained, melting around 134° C.

Methyl 7-aminoheptanoate is prepared according to C. F. Horn, B. T. Freure, H. Vineyard and H. J. Decker, Angew. Chem., 74, 531 (1962).

EXAMPLE 4

0.53 cm³ of triethylamine and 490 mg of methyl 8-aminooctanoate hydrochloride are added to a solution of 1 g of 3β-acetoxy-20(29)-lupen-28-oyl chloride in solution in 50 cm³ of methylene chloride and stirring is maintained for 20 hours at a temperature in the region of 20° C. After addition of 100 cm³ of distilled water, the organic phase is separated off, the aqueous phase is extracted with a total of 75 cm³ of methylene chloride, the organic extracts are combined, dried over anhydrous magnesium sulphate and concentrated to dryness under reduced pressure (2.7 kPa) at a temperature in the region of 35° C. The residue obtained is purified by HPLC, with fractions of 250 mg, on a column with a diameter of 5 cm containing 300 g of $C_{18}$-grafted silica (0.015–0.020 mm) eluted with a 70/15/15 (by volume) mixture of acetonitrile, water and tetrahydrofuran, under a pressure of 370 psi, while collecting 75 cm³ fractions. The first 3 fractions are discarded; the 2 following are combined and concentrated under reduced pressure (2.7 kPa) at a temperature in the region of 35° C. 750 mg of methyl N-[3β-acetoxy-20(29)-lupen-28-oyl]-8-aminooctanoate are thus obtained in the form of a white foam. [$R_f$=0.3; silica thin layer chromatography; eluent: cyclohexane/ethyl acetate] 80/20 (by volume).

A solution of 750 mg of methyl N-[3β-acetoxy-20(29)-lupen-28-oyl-8-aminooctanoate in 12 cm³ of methanol, 6 cm³ of tetrahydrofuran and 1.5 cm³ of 4N sodium hydroxide solution is stirred for 15 hours at a temperature in the region of 20° C. After addition of 10 cm³ of methanol, 2 cm³ of 5N hydrochloric acid and then 25 cm³ of distilled water, stirring is maintained for 30 minutes at a temperature in the region of 20° C. and the solid is separated by filtration, washed with a total of 50 cm³ of distilled water and dried under reduced pressure (13.5 Pa) at a temperature in the region of 40° C. 710 mg of N-[3β-hydroxy-20(29)-lupen-28-oyl]-8-aminooctanoic acid are thus obtained in the form of a white solid melting around 140° C.

Methyl 8-aminooctanoate hydrochloride can be obtained in the following way:

0.7 cm³ of thionyl chloride is added to a solution of 1 g of 8-aminooctanoic acid in 40 cm³ of methanol at a temperature in the region of −20° C. and stirring is maintained for 12 hours at a temperature in the region of 20° C. The solvent is removed under reduced pressure (2.7 kPa) at a temperature in the region of 35° C. 1.48 g of methyl 8-aminooctanoate hydrochloride is thus obtained in the form of a white solid.

EXAMPLE 5

310 mg of methyl 10-aminodecanoate hydrochloride and then 0.35 cm³ of triethylamine are added to 11 cm³ of a chloroform solution of 3β-acetoxy-20(29)-lupen-28-oyl chloride (prepared from 550 mg of 3β-acetoxy-20(29)-lupen-28-oic acid). The solution is then stirred for 15 hours at a temperature in the region of 20° C. After addition of 15 cm³ of distilled water, the reaction mixture is stirred for 1 hour, the organic phase is separated off and the aqueous phase is extracted with a total of 20 cm³ of chloroform. The combined organic phases are washed with a total of 20 cm³ of distilled water, dried over anhydrous sodium sulphate and concentrated to dryness under reduced pressure (2.7 kPa) at a temperature in the region of 30° C. 730 mg of a yellow foam are obtained which are chromatographed on a column with a diameter of 2.1 cm containing 35 g of silica (0.02–0.045 mm) eluted with a 60/40 (by volume) mixture of cyclohexane and ethyl acetate while collecting 5 cm³ fractions. After discarding the first 21 fractions, the following 17 are combined and concentrated under reduced pressure (2.7 kPa) at a temperature in the region of 30° C. 600 mg of methyl N-[3β-acetoxy-20(29)-lupen-28-oyl]-10-aminodecanoate are thus obtained in the form of a white foam. [$R_f$=0.72; silica thin layer chromatography; eluent: cyclohexane/ethyl acetate 60/40 (by volume)].

8.7 cm$^3$ of 4N sodium hydroxide solution are added to a solution of 600 mg of methyl N-[3β-acetoxy-20(29)-lupen-28-oyl]-10-aminodecanoate in 9 cm$^3$ of methanol and 4.5 cm$^3$ of tetrahydrofuran and the reaction mixture is stirred for 15 hours at a temperature in the region of 20° C. The mixture is diluted with 40 cm$^3$ of distilled water and is acidified using 10 cm$^3$ of 4N hydrochloric acid. After stirring for 1 hour, 15 cm$^3$ of ethyl ether are added and the organic phase is isolated. The aqueous phase is extracted with a total of 30 cm$^3$ of ether. The combined organic phases are washed with a total of 30 cm$^3$ of distilled water, dried over anhydrous sodium sulphate and evaporated to dryness under reduced pressure (2.7 kPa) at a temperature in the region of 30° C. 550 mg of N-[3β-hydroxy-20(29)-lupen-28-oyl]-10-aminodecanoic acid are thus obtained, melting around 100° C.

Methyl 10-aminodecanoate hydrochloride can be prepared as described in German Patent Application 971,392.

EXAMPLE 6

580 mg of methyl 11-aminoundecanoate hydrochloride and then 0.62 cm$^3$ of triethylamine are added to a solution of 1.03 g of 3β-acetoxy-20(29)-lupen-28-oyl chloride in 30 cm$^3$ of dichloromethane. The solution is then stirred for 48 hours at a temperature in the region of 20° C. and the solvent is evaporated to dryness under reduced pressure (2.7 kPa) at a temperature in the region of 20° C. 2 g of a yellow foam are obtained which are chromatographed on a column with a diameter of 2.7 cm containing 80 g of silica (0.02–0.045 mm) eluted with diisopropyl ether while collecting 20 cm$^3$ fractions. After discarding the first 10 fractions, the 6 following are combined and concentrated under reduced pressure (2.7 kPa) at a temperature in the region of 30° C. 1.29 g of methyl N-[3β-acetoxy-20(29)-lupen-28-oyl]-11-aminoundecanoate is thus obtained in the form of a white foam.

4.5 cm$^3$ of 4N sodium hydroxide solution are added to a solution of 1.28 g of methyl N-[3β-acetoxy-20(29)-lupen-28-oyl]-11-aminoundecanoate in 8 cm$^3$ of methanol and 13 cm$^3$ of tetrahydrofuran, the reaction mixture is stirred for 24 hours at a temperature in the region of 20° C. and the solvent is evaporated to dryness under reduced pressure (2.7 kPa) at a temperature in the region of 30° C. The residue is suspended in 60 cm$^3$ of distilled water. Acidification is carried out to a pH in the region of 2 using 3.6 cm$^3$ of 5N hydrochloric acid. After stirring for 20 minutes, the solid is separated by filtration, washed with distilled water to a pH in the region of 7 and dried in air at a temperature in the region of 20° C. 1.2 g of N-[3β-hydroxy-20(29)-lupen-28-oyl]-11-aminoundecanoic acid is thus obtained in the form of a white solid, melting around 115° C.

Methyl 11-aminoundecanoate is prepared according to H. Zahn and J. Kunde, Chem. Ber., 94, 2470 (1961).

EXAMPLE 7

243 mg of methyl 11-aminoundecanoate hydrochloride and then 0.27 cm$^3$ of triethylamine are added to 20 cm$^3$ of a 50/50 (by volume) tetrahydrofuran/chloroform mixture containing 453 mg of 3α-acetoxy-20(29)-lupen-28-oyl chloride. The solution is stirred for 20 hours at a temperature in the region of 20° C. and the solvent is evaporated to dryness under reduced pressure (2.7 kPa) at a temperature in the region of 30° C. The residue is taken up in 60 cm$^3$ of ethyl ether and 25 cm$^3$ of distilled water, the organic phase is separated off and the aqueous phase is extracted with a total of 25 cm$^3$ of ethyl ether. The combined organic phases are washed with a total of 45 cm$^3$ of distilled water, dried over anhydrous magnesium sulphate and concentrated to dryness under reduced pressure (2.7 kPa) at a temperature in the region of 30° C. The 600 mg of light yellow foam obtained are chromatographed on a column with a diameter of 2.5 cm containing 56 g of silica (0.063–0.200 mm) eluted with a 85/15 (by volume) mixture of cyclohexane and ethyl acetate while collecting 7 cm$^3$ fractions. The first 10 fractions are discarded; the following 17 are combined and concentrated under reduced pressure (2.7 kPa) at a temperature in the region of 30° C. 810 mg of methyl N-[3α-acetoxy-20(29)-lupen-28-oyl]-11-aminoundecanoate are thus obtained in the form of a white foam.

5.8 cm$^3$ of 4N sodium hydroxide solution are added over approximately 5 minutes to a solution of 400 g of methyl N-[3α-acetoxy-20(29)-lupen-28-oyl]-11-aminoundecanoate in 7 cm$^3$ of methanol and 3.5 cm$^3$ of tetrahydrofuran and the reaction mixture is stirred for 24 hours at a temperature in the region of 20° C. The mixture is diluted with 35 cm$^3$ of distilled water and the organic solvents are evaporated under reduced pressure (4.05 kPa) at a temperature in the region of 30° C. The aqueous suspension is then acidified to a pH in the region of 1 using 6.8 cm$^3$ of 4N hydrochloric acid. After stirring for 1 hour the aqueous phase is extracted with 50 cm$^3$ of ethyl ether. The organic phase is separated off and washed with a total of 45 cm$^3$ of distilled water, dried over anhydrous magnesium sulphate and concentrated to dryness under reduced pressure (4.05 kPa) at a temperature in the region of 30° C. 384 mg of an off-white foam are thus obtained which is suspended in 12 cm$^3$ of diisopropyl ether, separated by filtration and washed with a total of 8 cm$^3$ of diisopropyl ether. The solid (320 mg) is resuspended in 10 cm$^3$ of diisopropyl ether, 3 cm$^3$ of ethyl ether are added and the mixture is left stirring for 1 hour. The solid is separated by filtration, washed with a total of 10 cm$^3$ of diisopropyl ether and dried at reduced pressure (13.5 Pa) at a temperature in the region of 35° C. 290 mg of N-[3α-hydroxy-20(29)-lupen-28-oyl]-11-aminoundecanoic acid are thus obtained in the form of a white solid, melting around 220° C.

3α-Acetoxy-20(29)-lupen-28-oyl chloride can be prepared in the following way:

A solution of 267 mg of oxalyl chloride and 437 mg of 3α-acetylbetulinic acid in 14 cm$^3$ of chloroform is maintained with stirring at a temperature in the region of 20° C. for 18 hours and the solvent is evaporated under reduced pressure (2.7 kPa) at a temperature in the region of 30° C. The residue is taken up in 20 cm$^3$ of cyclohexane and the solvent is evaporated to dryness under reduced pressure under the same conditions. This operation is repeated 2 times. 453 mg of 3α-acetoxy-20(29)-lupen-28-oyl chloride are thus obtained.

3α-Acetoxy-20(29)-lupen-28-oic acid can be obtained in the following way:

A solution of 490 mg of acetic (3α-acetoxy-20(29)-lupen-28-oic) anhydride in 49 cm$^3$ of ethanol at 70% is heated for 1 hour 30 minutes at reflux in the presence of 4.9 cm$^3$ of 4N aqueous ammonia. The suspension is cooled to around 20° C., the insoluble material is separated by filtration, washed with a total of 20 cm$^3$ of absolute ethanol, and the combined filtrates are concentrated to dryness under reduced pressure (2.7 kPa) at a temperature in the region of 30° C. 452 mg of 3α-acetoxy-20(29)-lupen-28-oic acid are obtained in the form of a cream solid.

Acetic (3α-acetoxy-20(29)-lupen-28-oic) anhydride can be prepared in the following way:

A mixture of 445 mg of 3α-hydroxy-20(29)-lupen-28-oic acid (3α-betulinic acid), 1.14 g of sodium acetate and 4.5 cm³ of acetic anhydride is heated for 1 hour 15 minutes at reflux. The solution is then cooled to around 20° C., 15 cm³ of distilled water are then added dropwise and stirring is maintained for 1 hour. The solid formed is separated by filtration and washed with a total of 25 cm³ of distilled water. The residue is then dissolved in 50 cm³ of ethyl ether, 10 cm³ of distilled water are added, the organic phase is separated off, washed with 10 cm³ of distilled water, dried over anhydrous magnesium sulphate and concentrated to dryness under reduced pressure (2.7 kPa) at a temperature in the region of 30° C. 500 mg of acetic (3α-acetoxy-20(29)-lupen-28-oic) anhydride are thus obtained, in the form of a white foam.

3α-Betulinic acid is obtained according to W. Herz, Phytochemistry, 11, 3061 (1972).

EXAMPLE 8

610 mg of methyl 11-aminoundecanoate hydrochloride and then 0.68 cm³ of triethylamine are added to 20 cm³ of a chloroform solution of 3-oxo-20(29)-lupen-28-oyl chloride (prepared from 1 g of 3-oxo-20(29)-lupen-28-oic acid). The solution is then stirred for 15 hours at a temperature in the region of 20° C. After addition of 40 cm³ of distilled water, the organic phase is separated off and the aqueous phase is extracted with a total of 30 cm³ of chloroform. The combined organic phases are washed with a total of 30 cm³ of distilled water, dried over anhydrous sodium sulphate and concentrated to dryness under reduced pressure (2.7 kPa) at a temperature in the region of 40° C. 1.5 g of a yellow foam is obtained which is chromatographed on a column with a diameter of 3.5 cm containing 150 g of silica (0.02–0.045 mm) eluted with a 98/2 (by volume) mixture of methylene chloride and methanol while collecting 20 cm³ fractions. After discarding the first 45 fractions, the following 30 are combined and concentrated under reduced pressure (2.7 kPa) at a temperature in the region of 50° C. 1.1 g of methyl N-[3-oxo-20(29)-lupen-28-oyl]-11-aminoundecanoate is thus obtained in the form of a white foam. [$R_f$=0.5; silica thin layer chromatography; eluent: dichloromethane/ethanol 98/2 (by volume)].

9 cm³ of 4N sodium hydroxide solution are added to a solution of 600 mg of methyl N-(3-oxo-20(29)-lupen-28-oyl]-11-aminoundecanoate in 9 cm³ of methanol and 4.5 cm³ of tetrahydrofuran and the reaction mixture is stirred for 17 hours at a temperature in the region of 20° C. The mixture is diluted with 20 cm³ of distilled water and acidified using 12 cm³ of 4N hydrochloric acid. After stirring for 15 minutes, the suspension is treated with 25 cm³ of ethyl acetate and the organic phase is separated off. The aqueous phase is extracted with a total of 30 cm³ of ethyl acetate, the combined organic phases are washed with a total of 30 cm³ of distilled water, dried over anhydrous sodium sulphate and concentrated to dryness under reduced pressure (13.5 Pa) at a temperature in the region of 30° C. 340 mg of N-[3-oxo-20(29)-lupen-28-oyl]-11-aminoundecanoic acid are thus obtained in the form of a white powder, melting around 90° C.

3-Oxo-20(29)-lupen-28-oyl chloride can be prepared in the following way:

0.76 cm³ of oxalyl chloride are added with stirring to a solution of 2 g of 3-oxo-20(29)-lupen-28-oic acid in 44 cm³ of chloroform and stirring is maintained at a temperature in the region of 20° C. for 20 hours. The solvent is then evaporated to dryness under reduced pressure (2.7 kPa) at a temperature in the region of 35° C. The traces of oxalyl chloride are removed by suspending the residue in 10 cm³ of cyclohexane and by evaporating the solvent to dryness under reduced pressure (2.7 kPa) at a temperature in the region of 35° C. 2.2 g of 3-oxo-20(29)-lupen-28-oyl chloride are obtained in the form of a yellow foam.

3-Oxo-20(29)-lupen-28-oic acid is prepared according to R. Kawaguchi and K. W. Kim, J. Pharm. Soc. Jpn., 60, 595, 1940.

EXAMPLE 9

380 mg of methyl 11-aminoundecanoate hydrochloride and then 0.56 cm³ of triethylamine are added to a solution of 800 mg of 30-acetoxy-3-oxo-20(29)-lupen-28-oyl chloride in 40 cm³ of dichloromethane. The solution is then stirred for 1 hour and 30 minutes at a temperature in the region of 20° C. and the solvent is evaporated to dryness under reduced pressure (2.7 kPa) at a temperature in the region of 35° C. The residue obtained is chromatographed on a column with a diameter of 4 cm containing 125 g of silica (0.02–0.045 mm) eluted with a 6/4 (by volume) mixture of cyclohexane and ethyl acetate while collecting 25 cm³ fractions. The first 9 fractions obtained are discarded, the following 6 are concentrated to dryness under reduced pressure (2.7 kPa) at a temperature in the region of 45° C. 960 mg of methyl N-[30-acetoxy-3-oxo-20(29)-lupen-28-oyl]-11-aminoundecanoate are thus obtained in the form of a colourless lac.

1.6 cm³ of 4N sodium hydroxide solution are added to a solution of 930 mg of methyl N-[30-acetoxy-3-oxo-20(29)-lupen-28-oyl]-11-aminoundecanoate in 13 cm³ of methanol and 6.5 cm³ of tetrahydrofuran and the reaction mixture is stirred for 15 hours at a temperature in the region of 20° C. The mixture is acidified using 1.3 cm³ of 5N hydrochloric acid and is diluted with 100 cm³ of distilled water. After stirring for 1 hour, the solid is separated by filtration and washed with a total of 30 cm³ of distilled water. 730 mg of N-[30-hydroxy-3-oxo-20(29)-lupen-28-oyl]-11-aminoundecanoic acid are thus obtained, melting at a temperature in the region of 100° C.

30-Acetoxy-3-oxo-20(29)-lupen-28-oyl chloride is prepared in the following way:

0.22 cm³ of oxalyl chloride are added to a solution of 770 mg of 30-acetoxy-3-oxo-20(29)-lupen-28-oic acid in 38.5 cm³ of dichloromethane. After stirring for 15 hours at a temperature in the region of 20° C., the solvent is evaporated under reduced pressure (2.7 kPa) at a temperature in the region of 35° C. 800 mg of 30-acetoxy-3-oxo-20(29)-lupen-28-oyl chloride are obtained in the form of a white foam which is used without any other purification.

30-Acetoxy-3-oxo-20(29)-lupen-28-oic acid is obtained in the following way:

A solution of 1.6 g of chromic anhydride in 1.6 cm³ of distilled water and 16 cm³ of pyridine, cooled to 0° C., is added dropwise over approximately 30 minutes to a solution of 2.34 g of 30-acetoxy-3β-hydroxy-20(29)-lupen-28-oic acid in 28 cm³ of pyridine at 0° C. The reaction mixture is stirred for 1 hour at 0° C. then for 12 hours at a temperature in the region of 20° C., and is diluted with 250 cm³ of distilled water. 100 cm³ of ethyl acetate are added and the organic phase is separated off. The aqueous phase is extracted with 2 times 100 cm³ of ethyl acetate, the organic phases are combined, washed with a total of 200 cm³ of distilled water, dried over anhydrous magnesium sulphate and evaporated to dryness under reduced pressure (2.7 kPa) at a temperature in the region of 40° C. The residue obtained (2.4 g) is chromatographed on a column with a diameter of 5 cm containing 200 g of silica (0.20–0.045 mm), eluted with a 6/4 (by volume) mixture of cyclohexane and ethyl acetate while collecting 80 cm³ fractions. The first 9 fractions are discarded, the following 8 are combined and concentrated to dryness under reduced pressure (2.7 kPa) at a temperature in the region of 40° C. 1.55 g of 30-acetoxy-3-oxo-20(29)-lupen-28-oic acid is thus obtained in the form of a white foam.

30-Acetoxy-3β-hydroxy-20(29)-lupen-28-oic acid can be prepared in the following way:

A mixture of 4.44 g of 30-bromo-3β-hydroxy-20(29)-lupen-28-oic acid and 2.08 g of silver acetate in 250 cm³ of toluene is heated for half an hour at reflux. The insoluble material is filtered while hot and rinsed with a total of 75 cm³ of boiling toluene. The combined filtrates are then evaporated under reduced pressure (2.7 kPa). The residue (4.32 g) is chromatographed on a column with a diameter of 6 cm containing 350 g of silica (0.02–0.045 mm) eluted with a 7/3 (by volume) mixture of cyclohexane and ethyl acetate while collecting 100 cm³ fractions. The first 14 fractions obtained are discarded, the following 11 are combined and concentrated under reduced pressure (13.5 Pa) at a temperature in the region of 45° C. 2.34 g of 30-acetoxy-3β-hydroxy-20(29)-lupen-28-oic acid are thus obtained in the form of a white foam. [$R_f$=0.26; silica thin layer chromatography; eluent: cyclohexane/ethyl acetate 70/30 (by volume)].

30-Bromo-3β-hydroxy-20(29)-lupen-28-oic acid is obtained in the following way:

A solution of 4 g of 3β-hydroxy-20(29)-lupen-28-oic acid and 4.32 g of tetrabutylammonium tribromide in 80 cm³ of chloroform and 80 cm³ of tetrahydrofuran is stirred for 2 days at a temperature in the region of 25° C. The reaction mixture is washed successively 2 times with 50 cm³ of distilled water, 2 times with 25 cm³ of a 0.1N sodium thiosulphate solution and with 2 times 25 cm³ of distilled water and then dried over anhydrous magnesium sulphate. The organic phase is evaporated under reduced pressure (2.7 kPa) and at a temperature in the region of 40° C. A yellow pasty solid is obtained (5.01 g) which is chromatographed on a column with a diameter of 6 cm, containing 350 g of silica (0.02–0.045 mm) and eluted with a 90/10 (by volume) mixture of methylene chloride and ethyl acetate while collecting 50 cm³ fractions. The first 5 fractions obtained are discarded, the following 70 are evaporated under reduced pressure (2.7 kPa) at a temperature in the region of 40° C. 4.44 g of 30-bromo-3β-hydroxy-20(29)-lupen-28-oic acid are thus obtained in the form of a white solid. [$R_f$=0.3; silica thin layer chromatography; eluent: methylene chloride/ethyl acetate 90/10 (by volume)].

EXAMPLE 10

580 mg of methyl 11-aminoundecanoate hydrochloride and then 0.65 cm³ of triethylamine are added to 20 cm³ of a chloroform solution of 2,3-dioxo-20(29)-lupen-28-oyl chloride (prepared from 1 g of 2,3-dioxo-20(29)-lupen-28-oic acid). The solution is stirred for 24 hours at a temperature in the region of 20° C. 40 cm³ of distilled water are added, stirring is maintained for 15 minutes and then the organic phase is separated off and the aqueous phase is extracted with a total of 30 cm³ of chloroform. The combined organic phases are washed with a total of 30 cm³ of distilled water, dried over anhydrous sodium sulphate and concentrated to dryness under reduced pressure (2.7 kPa) at a temperature in the region of 40° C. 1.4 g of a yellow foam is obtained which is chromatographed a first time on a column with a diameter of 2.7 cm containing 70 g of silica (0.02–0.045 mm) by eluting with an 80/20 (by volume) mixture of cyclohexane and ethyl acetate and while collecting 10 cm³ fractions. After discarding the first 33 fractions, the following 12 are combined and concentrated under reduced pressure (2.7 kPa) at a temperature in the region of 40° C. The 700 mg of pale yellow oil obtained are chromatographed a further time on a column with a diameter of 2.8 cm containing 70 g of silica (0.020–0.045 mm). Elution is carried out with a 90/10 (by volume) mixture of methylene chloride and ethyl acetate, while collecting 15 cm³ fractions. The first 14 fractions are discarded; the following 7 are combined and concentrated under reduced pressure (2.7 kPa) at a temperature in the region of 35° C. 470 g of methyl N-(2,3-dioxo-20(29)-lupen-28-oyl)-11-aminodecanoate are obtained in the form of a yellow foam. [$R_f$=0.37; silica thin layer chromatography; eluent: chloroform/methanol 95/5 (by volume)].

7 cm³ of 4N sodium hydroxide solution are added to a solution of 470 mg of methyl N-[2,3-dioxo-20(29)-lupen-28-oyl]-11-aminoundecanoate in 7 cm³ of methanol and 3.5 cm³ of tetrahydrofuran and the reaction mixture is stirred for 15 hours at a temperature in the region of 20° C. The mixture is diluted with 15 cm³ of distilled water, acidified to a pH in the region of 3–4 using 9 cm³ of 4N hydrochloric acid, stirring is maintained for 15 minutes and 30 cm³ of chloroform are added. After separation of the organic phase, the aqueous phase is extracted with a total of 20 cm³ of chloroform. The combined organic phases are washed with a total of 20 cm³ of distilled water, dried over anhydrous sodium sulphate and concentrated under reduced pressure (2.7 kPa) at a temperature in the region of 40° C. The inorganic salts are removed by taking the residue up in 20 cm³ of ethyl acetate and 10 cm³ of 1N hydrochloric acid. The aqueous phase is extracted with a total of 20 cm³ of ethyl acetate. The combined organic phases are washed with a total of 30 cm³ of distilled water, dried over anhydrous sodium sulphate and concentrated to dryness under reduced pressure (2.7 kPa) at a temperature in the region of 35° C. 420 mg of a white foam are thus obtained which is chromatographed on a column with a diameter of 2.2 cm containing 40 g of silica (0.060 mm). Elution is carried out with a 95/5 (by volume) mixture of chloroform and methanol while collecting 5 cm³ fractions. The first 16 fractions are discarded; the following 6 are combined and concentrated under reduced pressure (12.5 Pa) at a temperature in the region of 35° C. 230 mg of N-[2,3-dioxo-20(29)-lupen-28-oyl]-11-aminoundecanoic acid are obtained in the form of a white foam, melting around 90° C. (sticky).

2,3-Dioxo-20(29)-lupen-28-oyl chloride can be prepared in the following way:

0.72 cm³ of oxalyl chloride is added with stirring to a solution of 1 g of 2,3-dioxo-20(29)-lupen-28-oic acid in 21 cm³ of chloroform and stirring is maintained at a temperature in the region of 20° C. for 18 hours. The solvent is then evaporated to dryness under reduced pressure (2.7 kPa) at a temperature in the region of 40° C. The residue is suspended in 10 cm³ of cyclohexane and the solvent is evaporated under reduced pressure (2.7 kPa) at a temperature in the region of 30° C. This operation is repeated 2 times. 940 mg of 2,3-dioxo-20(29)-lupen-28-oyl chloride are obtained in the form of a yellow foam [$R_f$=0.62; thin layer chromatography; eluent: cyclohexane/ethyl acetate 80/20 (by volume)].

2,3-dioxo-20(29)-lupen-28-oic acid is prepared in the following way:

3.48 g of potassium tert-butoxide are added to a solution of 5.27 g of 3-oxo-20(29)-lupen-28-oic acid in 248 cm³ of tert-butanol and then a stream of oxygen is passed in for 23 hours at a temperature in the region of 25° C. 31 cm³ of 1N hydrochloric acid are then added. After stirring for 15 minutes, the insoluble material is removed by filtration and the filtrate is evaporated to dryness under reduced pressure (2.7 kPa) at a temperature in the region of 40° C. The residue is taken up in 50 cm³ of cyclohexane and the solvent is evaporated to dryness under the same conditions; this operation is repeated 3 times. The 7.7 g of foam obtained are chromatographed on a column with a diameter of 4.5 cm containing 385 g of silica (0.020–0.045 mm), eluted with an 80/20 (by volume) mixture of cyclohexane and ethyl acetate, while collecting 50 cm³ fractions. The first 23 fractions are discarded, the following 9 are combined and concentrated to dryness under reduced pressure (2.7 kPa) at a temperature in the region of 40° C. 3.3 g of 2,3-dioxo-20(29)-lupen-28-oic acid are thus obtained in the form of a yellow foam [$R_f$=0.2; silica thin layer chromatography; eluent: cyclohexane/ethyl acetate 80/20 (by volume)].

EXAMPLE 11

280 mg of methyl 11-aminoundecanoate hydrochloride and 0.28 cm³ of triethylamine are added to 25 cm³ of a solution, in dichloromethane, of 3β,30-diacetoxy-20(29)-lupen-28-oyl chloride (prepared from 560 mg of 3β,30-diacetoxy-20(29)-lupen-28-oic acid). The solution is then stirred for 12 hours at a temperature in the region of 20° C. 10 cm³ of distilled water are then added. The organic phase is separated off and then washed with a total of 20 cm³ of distilled water. The combined organic phases are dried over anhydrous magnesium sulphate and concentrated to dryness under reduced pressure (2.7 kPa) at a temperature in the region of 35° C. The colourless oil obtained (750 mg) is chromatographed on a column with a diameter of 1.7 cm containing 15 g of silica (0.02–0,045 mm) eluted with an 80/20 (by volume) mixture of cyclohexane and ethyl acetate while collecting 15 cm³ fractions. The first 2 fractions obtained are discarded, the following 5 are concentrated to dryness under reduced pressure (22 kPa) at a temperature in the region of 40° C. 650 mg of methyl N-[3β,30-diacetoxy-20(29)-lupen-28-oyl]-11-aminoundecanoate are thus obtained in the form of a white lac [$R_f$=0.28; silica thin layer chromatography; eluent: cyclohexane/ethyl acetate] 80/20 (by volume).

10 cm³ of 4N sodium hydroxide solution are added to a solution of 650 mg of methyl N-[3β,30-diacetoxy-20(29)-lupen-28 -oyl]-11-aminoundecanoate in 10 cm³ of methanol and 5 cm³ of tetrahydrofuran and the reaction mixture is stirred for 18 hours at a temperature in the region of 20° C. The mixture is acidified to a pH in the region of 1–2 using 5N hydrochloric acid solution. After stirring for 1 hour, the solid is separated by filtration and washed with a total 30 cm³ of distilled water. The solid obtained is dissolved in a 90/10 (by volume) mixture of dichloromethane and ethanol. The insoluble material is filtered and the filtrates are concentrated under reduced pressure (13.5 Pa) at a temperature in the region of 40° C. An oil is thus obtained which is stirred with 20 cm³ of ethyl ether. After stirring for 12 hours at a temperature in the region of 20° C., the solid formed is filtered, then rinsed with a total of 10 cm³ of ethyl ether and dried under reduced pressure (13.5 Pa). 400 mg of N-[3β, 30-dihydroxy-20(29)-lupen-28-oyl]-11-aminoundecanoic acid are thus obtained, melting at a temperature in the region of 174° C.

3β,30-Diacetoxy-20(29)-lupen-28-oyl chloride is prepared in the following way:

0.22 cm³ of oxalyl chloride is added to a solution of 560 mg of 3β,30-diacetoxy-20(29)-lupen-28-oic acid in 25 cm³ of dichloromethane. After stirring for 15 hours at a temperature in the region of 20° C., the solvent is evaporated under reduced pressure (22 kPa) and at a temperature in the region of 40° C. 600 mg of a white foam are obtained which is used without any other purification.

3β,30-Diacetoxy-20(29)-lupen-28-oic acid is obtained in the following way:

A suspension of 1.8 g of 3β-acetoxy-30-bromo-20(29)-lupen-28-oic acid and 800 mg of silver acetate in 50 cm³ of toluene is stirred for 48 hours at a temperature in the region of 20° C. and then filtered. The solution obtained is then concentrated to dryness under reduced pressure (2 kPa). The residue is dissolved in 50 cm³ of ethyl acetate. The organic phase is separated off and washed with a total of 60 cm³ of distilled water, dried over anhydrous magnesium sulphate and then concentrated under reduced pressure (2.7 kPa) at a temperature in the region of 40° C. The white solid obtained (1.7 g) is chromatographed on a column with a diameter of 1.7 cm containing 35 g of silica (0.02–0.045 mm) eluted with an 80/20 (by volume) mixture of cyclohexane and ethyl acetate, while collecting 15 cm³ fractions. The first 4 fractions obtained are discarded, the following 10 are concentrated to dryness under reduced pressure (13.5 Pa) at a temperature in the region of 40° C. 1.1 g of 3β,30-diacetoxy-20(29)-lupen-28-oic acid is thus obtained in the form of a white foam which is sufficiently pure for subsequent conversions.

3β-Acetoxy-30-bromo-20(29)-lupen-28-oic acid is obtained in the following way:

A solution of 2.5 g of 3β-acetoxy-20(29)-lupen-28-oic acid and 2.41 g of tetrabutylammonium tribromide in 50 cm³ of chloroform is stirred for 5 days at a temperature in the region of 25° C. The reaction mixture is washed successively 2 times with 25 cm³ of distilled water, 2 times with 25 cm³ of a 0.1N sodium thiosulphate solution and with 2 times 25 cm³ of distilled water and then dried over anhydrous magnesium sulphate. The organic phase is concentrated to dryness under reduced pressure (2.7 kPa) and at a temperature in the region of 40° C. A yellow pasty solid (4 g) is obtained which is chromatographed on a column with a diameter of 3.2 cm containing 100 g of silica (0.02–0.045 mm) and eluted with an 85/15 (by volume) mixture of cyclohexane and ethyl acetate while collecting 20 cm³ fractions. The first 5 fractions obtained are discarded, the following 10 are evaporated under reduced pressure (13.5 Pa) at a temperature in the region of 40° C. 2.7 g of 3β-acetoxy-30-bromo-20(29)-lupen-28-oic acid are thus obtained in the form of a white solid melting at a temperature in the region of 190° C.

3β-Acetoxy-20(29)-lupen-28-oic acid can be prepared according to Bruckner, Kovacs and Koczka, J. Chem. Soc., 948 (1948).

EXAMPLE 12

After having heated a mixture of 190 mg of 11-aminoundecanoic acid and 308 mg of chlorotrimethylsilane in 50 cm³ of dichloromethane at reflux for 3 hours, the solution is cooled to around 20° C. and 750 mg of 30-acetoxy-3-oxo-20(29)-lupen-28-oyl chloride and then 0.72 cm³ of triethylamine are added. Stirring is maintained for 48 hours at a temperature in the region of 20° C. and the solvent is evaporated to dryness under reduced pressure (2.7 kPa) at a temperature in the region of 40° C. The residue is chromatographed on a column with a diameter of 4 cm containing 125 g of silica (0.02–0.045 mm), eluted in the presence of the mixture methylene chloride/methanol 80/20 (by volume) while collecting 50 cm³ fractions. The first 20 fractions are discarded, the following 20 are combined and concentrated to dryness under reduced pressure (2.7 kPa) at a temperature in the region of 40° C. 330 mg of N-[30-acetoxy-3-oxo-20(29)-lupen-8-oyl]-11-aminoundecanoic acid are thus obtained in the form of a white foam.

90 mg of sodium cyanoborohydride are added to a solution of 330 mg of N-[30-acetoxy-3-oxo-20(29)-lupen-28-oyl]-11-aminoundecanoic acid in 13 cm³ of methanol and then, over approximately 5 minutes, 1.46 cm³ of a 15% aqueous solution of titanium(III) chloride is added dropwise. The solution is maintained with stirring for 15 hours at a temperature in the region of 20° C. and 75 cm³ of distilled water, 50 cm³ of ethyl acetate and 10 cm³ of 1N hydrochloric acid are added. The organic phase is separated off, the aqueous phase is extracted with a total of 30 cm³ of ethyl acetate, the organic extracts are combined, dried over anhydrous magnesium sulphate and evaporated under reduced pressure (2.7 kPa) at a temperature in the region of 40° C. The residue obtained (370 mg) is chromatographed on a column with a diameter of 4 cm containing 125 g of silica (0.02–0.045 mm) eluted with a 60/40 (by volume) mixture of cyclohexane and ethyl acetate while collecting 50 cm³ fractions. The first 10 fractions are discarded; the following 7 are combined and concentrated under reduced pressure (2.7 kPa) at a temperature in the region of 40° C. The white solid obtained is dissolved in 0.5 cm³ of ethanol and is diluted with 22 cm³ of distilled water. After stirring for 10 minutes, the solid is separated by filtration, washed with a total of 20 cm³ of distilled water and dried in air. 260 mg of methyl N-[3β,30-dihydroxy-20(29)-lupen-28-oyl]-11-aminoundecanoate are obtained in the form of a white solid, melting at around 80° C.

EXAMPLE 13

A solution of 0.03 cm³ of oxalyl chloride in 5 cm³ of chloroform is added to a solution of 150 mg of 20,29,30-trinor-3β-acetoxy-19-[(2-acetoxyethyl)carbamoyl]lupan-28-oic acid in 10 cm³ of chloroform. The reaction mixture is stirred for 12 hours at a temperature in the region of 20° C. and is then concentrated under reduced pressure (15 kPa). The residue is taken up in 5 cm³ of chloroform. 80 mg of methyl 11-aminoundecanoate hydrochloride and 0.09 cm³ of triethylamine are added to the solution obtained. The solution is then stirred for 12 hours at a temperature in the region of 20° C. 10 cm³ of distilled water are added and the reaction mixture is then brought to a pH in the region of 2 by means of a 4N hydrochloric acid solution. The organic phase is separated off and the aqueous phase is extracted with 2 times 15 cm³ of chloroform. The combined organic phases are washed with a total of 60 cm³ of distilled water and are then dried for 3 hours over anhydrous magnesium sulphate and filtered. The organic phase is concentrated to dryness under reduced pressure (10 kPa) at a temperature in the region of 40° C. The 200 mg of pale yellow foam obtained are filtered on a column with a diameter of 2.7 cm, containing 50 g of silica (0.02–0.045 mm), eluted with a 24/6/1 (by volume) mixture of chloroform, methanol and 28% aqueous ammonia. The filtrate is concentrated to dryness under reduced pressure (13.5 Pa). 120 mg of methyl N-{20,29,30-trinor-3β-acetoxy-19-[(2-acetoxyethyl)carbamoyl] lupan-28-oyl}-11-aminoundecanoate are thus obtained in the form of a white lac [$R_f$=0.90; silica thin layer chromatography; eluent: chloroform/methanol/28% aqueous ammonia 24/6/1 (by volume)].

5 cm³ of 4N sodium hydroxide solution are added to a solution of 200 mg of methyl N-{20,29,30-trinor-3β-acetoxy-19-[(2-acetoxyethyl)carbamoyl]lupan-28-oyl}-11-aminoundecanoate in 10 cm³ of methanol and 5 cm³ of tetrahydrofuran and the reaction mixture is stirred for 15 hours at a temperature in the region of 20° C. The reaction mixture is then acidified to a pH in the region of 2 using 4N hydrochloric acid and diluted with 50 cm³ of distilled water. After stirring for 2 hours at a temperature in the region of 20° C., the solid is separated by filtration, washed with a total of 20 cm³ of distilled water end then dissolved in 10 cm³ of ethanol. The solution obtained is filtered and then concentrated to dryness under reduced pressure (13.5 Pa) at a temperature in the region of 20° C. The solid is taken up three times in 15 cm³ of ethanol and the solution is concentrated to dryness under reduced pressure. The solid residue is suspended in 50 cm³ of chloroform. The suspension is brought to a temperature in the region of 40° C. and filtered while hot. The filtrate is concentrated under reduced pressure (20 kPa) at a temperature in the region of 40° C. The residue is triturated with 5 cm³ of diisopropyl ether, filtered and then rinsed with 6 cm³ of diisopropyl ether. The solid is dried under reduced pressure (1 kPa) at a temperature in the region of 40° C. 90 mg of N-{20,29,30-trinor-3β-hydroxy-19-[(2-hydroxyethyl)carbamoyl]lupan-28-oyl}-11-aminoundecanoic acid are thus obtained in the form of a white solid melting at a temperature in the region of 170° C.

20,29,30-Trinor-3β-acetoxy-19-[(2-acetoxyethyl)carbamoyl]lupan-28-oic acid can be obtained in the following way:

30 mg of 4-dimethylaminopyridine, 0.35 cm³ of triethylamine and 0.1 cm³ of acetic anhydride are added to a solution of 450 mg of 20,29,30-trinor-3β-acetoxy-19-[(2-hydroxyethyl)carbamoyl] lupan-28-oic acid in 60 cm³ of chloroform. The reaction mixture is stirred for 72 hours at a temperature in the region of 20° C. and is then brought to a pH in the region of 1–2 using a 4N hydrochloric acid solution. The organic phase is separated off and then washed with a total of 30 cm³ of distilled water, dried for 1 hour over anhydrous magnesium sulphate and concentrated under reduced pressure (40.5 kPa) at a temperature in the region of 40° C. The solid residue is triturated with 5 cm³ of diisopropyl ether, filtered, rinsed with a total of 4 cm³ of diisopropyl ether and then dried under reduced pressure (100 Pa) at a temperature in the region of 40° C. 350 mg of 20,29,30-trinor-3β-acetoxy-19-[(2 -acetoxyethyl)carbamoyl]lupan-28-oic acid are thus obtained in the form of a white solid melting at a temperature in the region of 190° C.

20,29,30-Trinor-3β-acetoxy-19-[(2-hydroxyethyl)carbamoyl]lupan-28-oic acid can be obtained in the following way:

0.11 cm³ of oxalyl chloride is added to a solution of 500 mg of 29,30-dinor-3β-acetoxy-20,28-lupandioic acid in 50 cm³ of chloroform. The mixture is stirred for 12 hours at a temperature in the region of 20° C. and then it is concentrated under reduced pressure (20 kPa) to a temperature in the region of 40° C. The residual solid is dissolved in 15 cm³ of chloroform and a solution of 0.18 cm³ of ethanolamine in 5 cm³ of chloroform is added over 10 minutes. After stirring for 3 days at a temperature in the region of 20° C., 20 cm³ of distilled water are added and then the mixture is brought to a pH in the region of 1–2 using a 4N hydrochloric acid solution. The organic phase is separated off, washed with a total of 80 cm³ of distilled water, dried over anhydrous magnesium sulphate, filtered and then evaporated under reduced pressure (20 kPa) at a temperature in the region of 40° C. The 600 mg of pale yellow foam obtained are chromatographed on a column with a diameter of 1.8 cm, containing 20 g of silica (0.02–0.045 mm), eluted with a 95/5 (by volume) mixture of dichloromethane and methanol. The first 7 fractions are discarded and the following 12 are concentrated to dryness under reduced pressure (13.5 Pa). 230 mg of 20,29,30-trinor-3β-acetoxy-19-[(2-hydroxyethyl) carbamoyl]lupan-28-oic acid are thus obtained in the form of a white foam [$R_f$=0.30; silica thin layer chromatography; eluent: dichloromethane/methanol 95/5 (by volume)].

29,30-Dinor-3β-acetoxy-20,28-lupandioic acid can be obtained according to the method described by J. M. Guider et al., J. Chem. Soc., 3024 (1953).

EXAMPLE 14

A solution of 0.05 cm³ of oxalyl chloride in 5 cm³ of chloroform is added, over 1 minute, to a solution of 300 mg of 20,29,30-trinor-3β-acetoxy-19-(2-acetoxy-1-methoxycarbonylethylcarbamoyl)lupan-28-oic acid in 20 cm³ of chloroform. The reaction mixture is stirred for 12 hours at a temperature in the region of 20° C. and is then concentrated under reduced pressure (25 kPa). The residue is taken up in 15 cm³ of chloroform. 140 mg of methyl 11-aminoundecanoate hydrochloride and 0.15 cm³ of triethylamine are added to the solution obtained. The solution is then stirred for 12 hours at a temperature in the region of 20° C. 10 cm³ of distilled water are added and then the reaction mixture is brought to a pH in the region of 1 using a 4N hydrochloric acid solution. The organic phase is separated off and the aqueous phase is extracted with 2 times 10 cm³ of chloroform. The combined organic phases are washed with a total of 30 cm³ of distilled water, are then dried for 3 hours over magnesium sulphate and filtered. The organic phase is concentrated to dryness under reduced pressure (25 kPa) at a temperature in the region of 40° C. The 450 mg of pale yellow lac obtained are chromatographed on a column with a diameter of 1.7 cm, containing 20 g of silica (0.02–0.045 mm), eluted by means of a 97.5/2.5 (by volume) mixture of dichloromethane and methanol. 10 cm³ fractions are collected. The first 10 fractions are discarded and the following 15 are concentrated to dryness under reduced pressure (13.5 Pa). The 300 mg of solid obtained are chromatographed on a column with a diameter of 2.8 cm, containing 50 g of silica (0.02–0.045 mm), eluted by means of a 24/12/1 (by volume) mixture of chloroform, ethanol and 28% aqueous ammonia. 10 cm³ fractions are collected. The first 7 fractions are discarded and the following 10 are concentrated to dryness under reduced pressure (13.5 Pa). 200 mg of methyl N-[20, 29,30-trinor-3β-acetoxy-19-(2-acetoxy-1-methoxycarbonyl-ethylcarbamoyl)lupan-28-oyl]-11-aminoundecanoate are thus obtained in the form of a white lac [$R_f$=0.80; silica thin layer chromatography; eluent: chloroform/methanol/ 28% aqueous ammonia 24/6/1 (by volume)].

5 cm³ of 4N sodium hydroxide solution are added to a solution of 200 mg of methyl N-[20,29,30-trinor-3β-acetoxy-19-(2-acetoxy-1-methoxycarbonyl-ethylcarbamoyl)lupan-28-oyl]-11-aminoundecanoate in 10 cm³ of methanol and 5 cm³ of tetrahydrofuran and the reaction mixture is stirred for 15 hours at a temperature in the region of 20° C. The reaction mixture is then acidified to a pH in the region of 2 using 4N hydrochloric acid. The mixture is diluted with 50 cm³ of distilled water. The mixture is stirred for 2 hours at a temperature in the region of 20° C. The solid is separated by filtration, washed with a total of 25 cm³ of distilled water and then dried in air. The 160 mg of solid are chromatographed on a column with a diameter of 1.2 cm, containing 5 g of silica (0.02–0.045 mm), by means of a 12/6/1 (by volume) mixture of chloroform, methanol and 28% aqueous ammonia, while collecting 10 cm³ fractions. The first 9 fractions are discarded and the following 13 are concentrated to dryness under reduced pressure (13.5 Pa) at a temperature in the region of 40° C. The residue is triturated with 5 cm³ of diethyl ether, filtered, rinsed with a total of 6 cm³ of diethyl ether and then dried under reduced pressure (10 kPa). The 80 mg of solid obtained are dissolved in 2 cm³ of dioxane and then 0.5 cm³ of a 4N aqueous hydrochloric acid solution and 15 cm³ of distilled water are added. The solid is filtered, washed 4 times with 2 cm³ of distilled water and then dissolved in 10 cm³ of ethanol. The solution obtained is filtered and then evaporated under reduced pressure (8 kPa) at a temperature in the region of 35° C. The addition of ethanol and the evaporation are repeated 3 times. The residue is dissolved in a mixture of 30 cm³ of chloroform and 3 cm³ of tetrahydrofuran. The solution is filtered and then concentrated under reduced pressure (8 kPa) at a temperature in the region of 40° C. The residue is triturated with 5 cm³ of diisopropyl ether, filtered, rinsed 3 times with 2 cm³ of diisopropyl ether and then dried under reduced pressure (13.5 Pa). 50 mg of N-[20,29,30-trinor-3β-hydroxy-19-(1-carboxy-2-hydroxyethylcarbamoyl)lupan-28-oyl]-11-aminoundecanoic acid are thus obtained in the form of a white solid melting at a temperature in the region of 208° C.

20,29,30-Trinor-3β-acetoxy-1-(2-acetoxy-19-methoxycarbonylethylcarbamoyl)lupan-28-oic acid can be obtained in the following way:

30 mg of 4-dimethylaminopyridine, 0.35 cm³ of triethylamine and 0.21 cm³ of acetic anhydride are added to a solution of 300 mg of 20,29,30-trinor-3β-acetoxy-19-(2-hydroxy-1-methoxycarbonylethylcarbamoyl)lupan-28-oic acid in 25 cm³ of chloroform. The reaction mixture is stirred for 12 hours at a temperature in the region of 20° C. 20 cm³ of distilled water are added and then the mixture is brought to a pH in the region of 2–3 using a 4N hydrochloric acid solution. The organic phase is separated off, then washed with a total of 60 cm³ of distilled water, dried for 1 hour over anhydrous magnesium sulphate and concentrated under reduced pressure (15 kPa) at a temperature in the region of 40° C. 2 cm³ of dioxane and 20 cm³ of water are added to the colourless oil obtained. After trituration and cooling to a temperature in the region of 0° C., the solid is filtered, washed by means of 3 times 5 cm³ of distilled water and then dried under reduced pressure (100 Pa) at a temperature in the region of 40° C. 300 mg of 20,29,30-trinor-3β-acetoxy-19-(2-acetoxy-1-methoxycarbonylethylcarbamoyl)lupan-28-oic acid are thus obtained in the form of a white solid melting at a temperature in the region of 180° C.

20,29,30-Trinor-3β-acetoxy-19-(2-hydroxy-1-methoxycarbonylethylcarbamoyl)lupan-28-oic acid can be obtained in the following way:

0.38 cm³ of oxalyl chloride is added to a solution of 1.8 g of 29,30-dinor-3β-acetoxy-20,28-lupandioic acid in 150 cm³ of chloroform. The mixture is stirred for 12 hours at a temperature in the region of 20° C. and then concentrated under reduced pressure (20 kPa) at a temperature in the region of 40° C. The residual solid is dissolved in 40 cm³ of chloroform and a solution of 700 mg of methyl L-serinate hydrochloride and 1.5 cm³ of triethylamine is added over 10 minutes. After stirring for 12 hours at a temperature in the region of 20° C., 50 cm³ of distilled water are added and then the mixture is brought to a pH in the region of 1–2 using a 4N hydrochloric acid solution. The organic phase is separated off, washed with 30 cm³ of distilled water, dried over anhydrous magnesium sulphate and concentrated to dryness under reduced pressure (20 kPa) at a temperature in the region of 40° C. The 600 mg of pale yellow foam obtained are chromatographed on a column with a diameter of 2.4 cm, containing 50 of silica (0.02–0.045 mm), eluted by means of a 1/1 (by volume) ethyl acetate/dichloromethane mixture. The first 14 fractions are discarded and the following 9 are concentrated to dryness under reduced pressure (13.5 Pa). 800 mg are thus obtained of a solid which is triturated with 10 cm³ of acetonitrile, filtered, washed with 2 times 2 cm³ of acetonitrile and dried under reduced pressure (13.5 Pa). 800 mg of 20,29,30-trinor-3β-acetoxy-19-[2-hydroxy-1-(methoxycarbonyl)ethylcarbamoyl]lupan-28-oic acid are thus obtained in the form of a white foam, melting at a temperature in the region of 230° C.

EXAMPLE 15

2.2 cm³ of triethylamine and 1.94 g of methyl 11-aminoundecanoate hydrochloride are added to 195 cm³ of a methylene chloride solution of 30-nor-3β-acetoxy-20-oxo-28-lupanoyl chloride. The solution is then stirred for 72 hours at a temperature in the region of 20° C. The reaction mixture is diluted with 100 cm³ of dichloromethane and the organic phase is washed with 3 times 150 cm³ of distilled water. The combined organic phases are dried for 3 hours over magnesium sulphate and filtered. The organic phases are concentrated to dryness under reduced pressure (2.7 kPa) at a temperature in the region of 50° C. The pale yellow oil obtained (5.7 g) is chromatographed on a column with a diameter of 4 cm and a height of 60 cm containing silica (0.02–0.045 nun) and eluted successively with a 70/30 (by volume) mixture of cyclohexane and ethyl acetate for the fractions 1 to 50 and a 50/50 (by volume) mixture of cyclohexane and ethyl acetate for the following fractions. 100 cm³ fractions are collected. The first 30 fractions are discarded; the following 32 are combined and concentrated under reduced pressure (2.7 kPa) at a temperature in the region of 35° C. 5 g are thus obtained of a white foam which is triturated with 2 times 100 cm³ of diisopropyl ether and then dried under reduced pressure (2.7 kPa) at a temperature in the region of 40° C. 4.75 g of methyl N-(30-nor-3β-acetoxy-20-oxo-28-lupanoyl)-11-aminoundecanoate are thus obtained in the form of a white foam [$R_f$=0.23; silica thin layer chromatography; eluent cyclohexane/ethyl acetate 8/2 (by volume)].

10 cm³ of 5N sodium hydroxide solution are added to a solution of 700 mg of methyl N-(30-nor-3β-acetoxy-20-oxo-28-lupanoyl)-11-aminoundecanoate in 15 cm³ of methanol and 15 cm³ of tetrahydrofuran and the reaction mixture is stirred for 48 hours at a temperature in the region of 20° C. A mixture of 10 cm³ of methanol and 10 cm³ of tetrahydrofuran is added successively on 3 occasions and at 24-hour intervals while leaving the reaction mixture to stir at a temperature in the region of 20° C. The reaction mixture is then acidified to a pH in the region of 2 using 4N hydrochloric acid. 150 cm³ of distilled water are added. After stirring for 2 hours at a temperature in the region of 20° C., the solid is separated by filtration, washed with a total of 180 cm³ of distilled water and dried under reduced (13.5 Pa) at a temperature in the region of 20° C. 500 mg of a white solid are thus obtained. The aqueous phase is extracted with a total of 200 cm³ of dichloromethane. The combined organic phases are dried over anhydrous magnesium sulphate and then evaporated under reduced pressure (13.5 Pa) at a temperature in the region of 20° C. 150 mg of a pale yellow oil are thus obtained. The solid and the oil are combined and chromatographed on a column with a diameter of 2 cm and a height of 40 cm, containing silica (0.02–0.045 mm) eluted with a 50/50 (by volume) mixture of cyclohexane and ethyl acetate, while collecting 10 cm³ fractions. The first 15 fractions are discarded; the following 10 are combined and concentrated under reduced pressure (2.7 kPa) at a temperature in the region of 35° C. 400 mg of a pale yellow oil are thus obtained. This oil is dissolved in 1.5 cm³ of tetrahydrofuran. After stirring for 20 minutes at a temperature in the region of 20° C., 1.5 cm³ and 10 cm³ of diisopropyl ether are added at a 20-minute interval. The solid is separated by filtration and dried under reduced pressure (13.5 Pa) at a temperature in the region of 40° C. 200 mg of N-(30-nor-3β-acetoxy-20-oxo-28-lupanoyl)-11-aminoundecanoic acid are thus obtained in the form of a white solid melting around 150° C.

30-Nor-3β-acetoxy-20-oxo-28-lupanoyl chloride is obtained in the following way:

1.5 cm³ of oxalyl chloride is added over 5 minutes to 150 cm³ of a solution of 30-nor-3β-acetoxy-20-oxolupanoic acid in dichloromethane. The solution is then stirred for 20 hours at a temperature in the region of 20° C. The reaction mixture is concentrated to dryness under reduced pressure (2.7 kPa) at a temperature in the region of 40° C. The white foam obtained is triturated with 2 times 200 cm³ of cyclohexane. The solid is filtered and dried under reduced pressure (2.7 kPa) at a temperature in the region of 40° C. 3.7 g of 30-nor-3β-acetoxy-20-oxo-28-lupanoyl chloride are thus obtained in the form of a white foam.

30-Nor-3β-acetoxy-20-oxo-28-lupanoic acid is prepared according to A. Vystrcil and M. Budesinsy, Collect. Czech. Chem. Commun., 35, 295 (1970).

EXAMPLE 16

370 mg of methyl 12-aminododecanoate hydrochloride and then 0.4 cm³ of triethylamine are added to a solution of 660 mg of 3β-acetoxy-20(29)-lupen-28-oyl chloride in 13.2 cm³ of chloroform and 13 cm³ of tetrahydrofuran. The solution is stirred for 20 hours at a temperature in the region of 20° C. and the solvent is evaporated under reduced pressure (2.7 kPa) at a temperature in the region of 35° C. The residue is treated with 60 cm³ of ethyl ether and 25 cm³ of distilled water. The organic phase is separated off and the aqueous phase is extracted with a total of 40 cm³ of ethyl ether. The combined organic phases are washed with a total of 60 cm³ of distilled water, dried over anhydrous sodium sulphate and concentrated to dryness under reduced pressure (2.7 kPa) at a temperature in the region of 30° C. The 860 mg of cream-coloured foam obtained are chromatographed on a column with a diameter of 2 cm containing 52 g of silica (0.02–0.045 mm) eluted with an 80/20 (by volume) mixture of cyclohexane and ethyl acetate while collecting 7 cm³ fractions. The first 7 fractions are discarded; the following 7 are combined and concentrated under reduced pressure (2.7 kPa) at a temperature in the region of 35° C. 650 mg of methyl N-[3β-acetoxy-20(29)-lupen-28-oyl]-12-aminododecanoate are thus obtained in the form of a white foam.

8.1 cm$^3$ of 4N sodium hydroxide solution are added over approximately 5 minutes to a solution of 570 mg of methyl N-[3β-acetoxy-20(29)-lupen-28-oyl]-12-aminododecanoate in 9 cm$^3$ of methanol and 4.5 cm$^3$ of tetrahydrofuran. The reaction mixture is stirred for 20 hours at a temperature in the region of 20° C. and the solvent is evaporated under reduced pressure (2.7 kPa) at a temperature in the region of 35° C. The mixture is diluted with 40 cm$^3$ of distilled water and acidified to a pH in the region of 1 using 9.5 cm$^3$ of 4N hydrochloric acid. After stirring for 15 hours at a temperature in the region of 20° C., 120 cm$^3$ of ethyl ether are added and the organic phase is separated off. The aqueous phase is extracted again with 50 cm$^3$ of ethyl ether, the combined organic phases are washed with a total of 75 cm$^3$ of distilled water, dried over anhydrous magnesium sulphate and evaporated to dryness under reduced pressure (2.7 kPa) at a temperature in the region of 30° C. The residue is suspended in 9 cm$^3$ of diisopropyl ether, the solid is separated by filtration, washed with a total of 4 cm$^3$ of diisopropyl ether and dried under reduced pressure (13.5 Pa) at a temperature in the region of 30° C. 470 mg of N-[3β-hydroxy-20(29)-lupen-28-oyl]-12-aminododecanoic acid are thus obtained, melting around 182° C.

Methyl 12-aminododecanoate is prepared according to H. Zahn and H. D. Stoper, Chem. Ber., 98(10), 3251 (1965).

EXAMPLE 17

0.24 cm$^3$ of triethylamine and 500 mg of methyl 16-aminohexadecanoate hydrochloride are added to a solution of 820 mg of 3β-acetoxy-20(29)-lupen-28-oyl chloride in solution in a mixture composed of 20 cm$^3$ of chloroform and 20 cm$^3$ of tetrahydrofuran. After stirring for 20 hours at a temperature in the region of 20° C., 40 cm$^3$ of distilled water are added and the organic phase is separated off. The aqueous phase is extracted with a total of 75 cm$^3$ of chloroform, the organic extracts are combined, dried over anhydrous magnesium sulphate and evaporated under reduced pressure (2.7 kPa) at a temperature in the region of 35° C. The residue obtained is chromatographed a first time on a column with a diameter of 4 cm containing 150 g of silica (0.02–0.045 mm) eluted with an 80/20 (by volume) mixture of cyclohexane and ethyl acetate and while collecting 10 cm$^3$ fractions. The first 80 fractions are discarded; the following 23 are combined and concentrated under reduced pressure (2.7 kPa) at a temperature in the region of 35° C. 568 mg of a beige foam are thus obtained, which is chromatographed a second time (column with a diameter of 4 cm; 150 g of silica (0.02–0.045 mm), 30 cm$^3$ fractions). The eluent system is composed of a 99/1 (by volume) mixture of methylene chloride and methanol. The first 30 fractions are discarded, the following 6 are combined and evaporated to dryness under reduced pressure (2.7 kPa) at a temperature in the region of 30° C. The 363 mg obtained are chromatographed a third time on a column with a diameter of 1.7 cm, containing 20 g of silica (0.02–0.045 mm) by eluting with an 80/20 (by volume) mixture of cyclohexane and ethyl acetate. 3 cm$^3$ fractions are collected. The first 13 fractions are discarded; the following 17 are combined and concentrated to dryness under reduced pressure (2.7 kPa) at a temperature in the region of 30° C. 380 mg of methyl N-[3β-acetoxy-20(29)-lupen-28-oyl]-16-aminohexadecanoate are thus obtained in the form of a white foam [R$_f$=0.3; silica thin layer chromatography; eluent: methylene chloride/ethyl acetate 97/3 (by volume)].

A solution of 380 mg of N-[3β-acetoxy-20(29)-lupen-28-oyl]-16-aminohexadecanoate in a mixture of 5 cm$^3$ of methanol, 2.5 cm$^3$ of tetrahydrofuran and 0.62 cm$^3$ of 4N sodium hydroxide solution is stirred for 15 hours at a temperature in the region of 20° C. The solvent is then evaporated to dryness under reduced pressure (2.7 kPa) at a temperature in the region of 30° C. The white residue is suspended in 25 cm$^3$ of distilled water. 1 cm$^3$ of 5N hydrochloric acid is added and stirring is maintained for 20 minutes. The solid is separated by filtration, washed with a total of 50 cm$^3$ of distilled water and dried under reduced pressure (13.5 Pa) at a temperature in the region of 20° C. The solid obtained is suspended in 20 cm$^3$ of distilled water and filtered. 292 mg are thus obtained of acid which is purified by chromatography on a column with a diameter of 1.7 cm containing 20 g of silica (0.02–0.045 mm) eluted with a 50/40/10 (by volume) mixture of cyclohexane, ethyl acetate and methylene chloride while collecting 2 cm$^3$ fractions. The first 10 fractions are discarded, the following 9 are combined and concentrated to dryness under reduced pressure (2.7 kPa) at a temperature in the region of 30° C. 280 mg of N-[3β-hydroxy-20(29)-lupen-28-oyl]-16-aminohexadecanoic acid are thus obtained in the form of a white solid melting around 85° C.

Methyl 16-aminohexadecanoate can be prepared in the following way:

A solution of 1.3 g of methyl 16-phthalimidohexadecanoate in 50 cm$^3$ of methanol is stirred for 3 hours, at a temperature in the region of 80° C., in the presence of 170 mg of hydrazine hydrate. The solution is cooled to around 20° C. and 2 cm$^3$ of 5N ethereal hydrochloric acid are added. The solvent is evaporated under reduced pressure (2.7 kPa) at a temperature in the region of 35° C. The residue is taken up in 50 cm$^3$ of distilled water. The solid is separated by filtration. The filtrates are concentrated to dryness under reduced pressure at a temperature in the region of 35° C. 320 mg of a white solid are obtained. The solid, separated by filtration, is washed with a total of 25 cm$^3$ of distilled water, suspended in 20 cm$^3$ of distilled water, and 1 cm$^3$ of 5N hydrochloric acid is added. After stirring for 15 minutes, the crystals are separated by filtration, washed with 20 cm$^3$ of 1N hydrochloric acid and 20 cm$^3$ of distilled water. This batch (1.2 g), combined with the 320 mg obtained after evaporation of the filtrates, is chromatographed on a column with a diameter of 2 cm containing 30 g of silica (0.02–0.045 mm), eluted with a 90/10 (by volume) mixture of chloroform and methanol while collecting 20 cm$^3$ fractions. The first 3 fractions are discarded, the following 6 are combined and evaporated under reduced pressure (2.7 kPa) at a temperature in the region of 35° C. The residue is suspended in 20 cm$^3$ of a saturated sodium bicarbonate solution and stirred for 15 minutes. The solid is separated by filtration, washed with a total of 50 cm$^3$ of distilled water and dried under reduced pressure (13.5 Pa) at a temperature in the region of 20° C. 500 mg of methyl 16-aminohexadecanoate are thus obtained in the form of a white solid.

Methyl 16-phthalimidohexadecanoate can be prepared in the following way:

A solution of 0.89 cm$^3$ of ethyl azidodicarboxylate in 2.6 cm$^3$ of tetrahydrofuran is added dropwise to a mixture of 1.36 g of methyl 16-hydroxyhexadecanoate, 847 mg of phthalimide and 1.49 g of triphenylphosphine in 2.6 cm$^3$ of tetrahydrofuran. Stirring is maintained for 15 hours at a temperature in the region of 20° C. and the solvent is evaporated under reduced pressure (2.7 kPa) at a temperature in the region of 30° C. The 5.4 g of residue obtained are chromatographed on a column with a diameter of 3 cm containing 100 g of silica (0.020–0.045 mm) eluted with methylene chloride. The first 18 fractions are discarded, the following 36 are combined and evaporated to dryness under reduced pressure (2.7 kPa) at a temperature in the region of 30° C. 1.5 g of methyl 16-phthalimidohexadecanoate are thus obtained in the form of a white solid.

EXAMPLE 18

0.31 cm$^3$ of triethylamine and 660 mg of methyl 17-aminoheptadecanoate hydrochloride are added to a solution of 1 g of 3β-acetoxy-20(29)-lupen-28-oyl chloride in a mixture of 20 cm$^3$ of chloroform and 20 cm$^3$ of tetrahydrofuran. After stirring for 20 hours at a temperature in the region of 20° C., 40 cm$^3$ of distilled water are added. The organic phase is separated off and the aqueous phase is extracted with a total of 100 cm$^3$ of chloroform. The organic extracts are combined, dried over anhydrous magnesium sulphate and the solvent is removed under reduced pressure (2.7 kPa) at a temperature in the region of 30° C. The residue obtained is chromatographed a first time on a column with a diameter of 4 cm containing 100 g of silica (0.02–0.045 mm). The eluting mixture is composed of 95/5 (by volume) methylene chloride and ethyl acetate and the fractions are 30 cm$^3$. After discarding the first 5 fractions, the following 19 are combined and concentrated under reduced pressure (2.7 kPa) at a temperature in the region of 35° C. 750 mg of a white foam are thus obtained which is chromatographed a second time: column with a diameter of 2.2 cm, 40 g of silica (0.02–0.045 mm), eluting with a 98/2 (by volume) mixture of methylene chloride and ethyl acetate and collecting 10 cm$^3$ fractions. The first 16 fractions are discarded, the following 17 are combined and concentrated to dryness under reduced pressure (2.7 kPa) at a temperature in the region of 30° C. The 540 mg obtained are chromatographed a third time on a column with a diameter of 2 cm containing 40 g of silica (0.02–0.045 mm) eluted with an 80/20 (by volume) mixture of cyclohexane and ethyl acetate while collecting 5 cm$^3$ fractions. After discarding the first 4 fractions, the following 10 are combined and concentrated to dryness under reduced pressure at a temperature in the region of 30° C. (2.7 kPa). The 443 mg obtained are chromatographed a last time on a column with a diameter of 1.4 cm containing 20 g of silica (0.020–0.045 mm) eluted with an 80/20 (by volume) mixture of cyclohexane and ethyl acetate, while collecting 5 cm$^3$ fractions. After discarding the first 2 fractions, the following 7 are combined and concentrated to dryness under reduced pressure (2.7 kPa) at a temperature in the region of 30° C. 210 mg of methyl N-[3β-acetoxy-20(29)-lupen-28-oyl-17-aminoheptadecanoate are obtained in the form of a white foam [$R_f$=0.4; silica thin layer chromatography; eluent: cyclohexane/ethyl acetate 80/20 (by volume)].

A solution of 210 mg of methyl N-[3β-acetoxy-20(29)-lupen-28-oyl-17-aminoheptadecanoate in 2.7 cm$^3$ of methanol, 1.3 cm$^3$ of tetrahydrofuran and 0.34 cm$^3$ of 4N sodium hydroxide solution is stirred for 15 hours at a temperature in the region of 20° C. The solvent is then removed under reduced pressure (2.7 kPa) at a temperature in the region of 30° C. The residue is dissolved in 12.5 cm$^3$ of distilled water and 0.5 cm$^3$ of 5N hydrochloric acid is added. After stirring for 20 minutes, the solid is separated by filtration, washed with a total of 50 cm$^3$ distilled water and dried under reduced pressure (13.5 Pa) at a temperature in the region of 20° C. 194 mg are thus obtained of acid which is chromatographed on a column with a diameter of 1.7 cm containing 20 g of silica (0.020–0.045 mm), eluted with a 50/40/10 (by volume) mixture of cyclohexane, ethyl acetate and methylene chloride while collecting 5 cm$^3$ fractions. The first 10 fractions are discarded, the following 9 are combined and concentrated to dryness under reduced pressure (2.7 kPa) at a temperature in the region of 35° C. The solid obtained is suspended in 20 cm$^3$ of distilled water and separated by filtration. 220 mg of N-[3β-hydroxy-20(29)-lupen-28-oyl-17-aminoheptadecanoic acid are thus obtained in the form of a white solid, melting around 82° C.

Methyl 17-aminoheptadecanoate is prepared in the following way:

0.37 cm$^3$ of thionyl chloride are added to 23 cm$^3$ of methanol cooled to –20° C. and 980 mg of 17-aminoheptadecanoic acid are added. The solution is stirred for 12 hours at a temperature in the region of 20° C. and the solvent is removed under reduced pressure (2.7 kPa) at a temperature in the region of 40° C. 1.08 g of methyl 17-aminoheptadecanoate hydrochloride are thus obtained in the form of a white solid.

17-Aminoheptadecanoic acid can be prepared in the following way:

A solution of 3.4 g of 17-phthalimidoheptadecanoic acid in 60 cm$^3$ of methanol is stirred for 1 hour, at a temperature in the region of 80° C., in the presence of 1.67 g of hydrazine hydrate. The solution is cooled to around 20° C. and the solid is separated by filtration and dried in air. The residue (1.92 g) is taken up in 180 cm$^3$ of distilled water. The solid is separated by filtration, washed with a total of 45 cm$^3$ of distilled water and dried under reduced pressure (13.5 Pa) at a temperature in the region of 40° C. 980 mg of 17-aminoheptadecanoic acid are obtained in the form of a white solid.

17-Phthalimidoheptadecanoic acid can be prepared in the following way:

2 g of 17-bromoheptadecanoic acid are added to 2.14 g of potassium phthalimide in 40 cm$^3$ of N,N-dimethylformamide and the mixture is heated for 6 hours at a temperature in the region of 80° C. The solution is cooled to about 20° C., it is poured into 100 cm$^3$ of distilled water and 10 cm$^3$ of 2N hydrochloric acid are added dropwise. The solid formed is separated by filtration. 5.13 g are obtained of a residue which is chromatographed on a column with a diameter of 4 cm containing 250 g of silica (0.020–0.045 mm) eluted with a 95/5 (by volume) mixture of methylene chloride and methanol. The first 4 fractions are discarded, the following 3 are combined and concentrated to dryness under reduced pressure (2.7 kPa) at a temperature in the region of 40° C. 3.39 g of 17-phthalimidoheptadecanoic acid are thus obtained in the form of a white solid.

EXAMPLE 19

A solution of 1.1 g of 3β-acetoxy-20(29)-lupen-28-oyl chloride (prepared from μl g of 3β-acetoxy-20(29)-lupen-28-oic acid) in 50 cm$^3$ of dichloromethane is added to a solution of 0.54 g of methyl 11-amino-2,2-dimethylundecanoate and 0.28 cm$^3$ of triethylamine in 50 cm$^3$ of dichloromethane. The solution is stirred for 15 hours at a temperature in the region of 20° C. 100 cm$^3$ of dichloromethane are added. The organic phase is washed with a total of 300 cm$^3$ of distilled water, dried over magnesium sulphate and concentrated to dryness under reduced pressure (2.7 kPa) at a temperature in the region of 40° C. The 2 g of oil obtained are chromatographed on a column with a diameter of 3 cm and a height of 50 cm containing silica (0.02–0.045 mm) eluted with a 95/5 (by volume) mixture of dichloromethane and ethyl acetate, while collecting 50 cm$^3$ fractions. The first 12 fractions are discarded, the following 4 are combined and concentrated under reduced pressure (2.7 kPa) at a temperature in the region of 60° C. The yellow oil obtained is dissolved in 100 cm³ of dichloromethane. The organic phase is washed with a total of 150 cm³ of distilled water, dried over magnesium sulphate and then concentrated under reduced pressure (2.7 kPa) at a temperature in the region of 40° C. The 1.1 g of yellow oil obtained is chromatographed on a column with a diameter of 2 cm and a height of 40 cm containing silica (0.02–0.045 mm), eluted with dichloromethane, while collecting 50 cm³ fractions. The first 25 fractions are discarded. The following 21 are combined and concentrated under reduced pressure (13.5 Pa) at a temperature in the region of 40° C. 0.80 g of methyl N-[3β-acetoxy-20(29)-lupen-28-oyl]-11 -amino-2,2-dimethylundecanoate are obtained in the form of a white lac [$R_f$=0.12; silica thin layer chromatography; eluent: dichloromethane].

19 cm³ of 4N sodium hydroxide solution are added over approximately 5 minutes to a solution of 1.4 g of methyl N-[3β-acetoxy-20(29)-lupen-28-oyl]-11-amino-2,2-dimethylndecanoate in 40 cm³ of methanol and 40 cm³ of tetrahydrofuran and the reaction mixture is stirred for 48 hours at a temperature in the region of 20° C. The reaction mixture is acidified to a pH in the region of 2 using 4N hydrochloric acid and then 200 cm³ of distilled water are added. After stirring for 30 minutes, the aqueous phase is separated off, the solid is separated by filtration and rinsed with a total of 90 cm³ of distilled water. The filtrate is taken up in 100 cm³ of ethyl acetate. The organic phase is dried for 2 hours over magnesium sulphate and evaporated to dryness under reduced pressure (2.7 kPa) at a temperature in the region of 40° C. The 1.4 g of white foam obtained is chromatographed on a column with a diameter of 2.7 cm and a height of 36 cm containing silica (0.02–0.045 mm) eluted successively with dichloromethane (fractions 1 to 25), a 95/5 (by volume) mixture of dichloromethane and ethyl acetate (fractions 26 to 80) and a 9/1 (by volume) mixture of dichloromethane and ethyl acetate (fractions 81 to 120) while collecting 50 cm³ fractions. The first 95 fractions are discarded, the following 20 are combined and concentrated under reduced pressure (2.7 kPa) at a temperature in the region of 40° C. 1 g is thus obtained of a white foam which is triturated with 15 cm³ of n-heptane, filtered, washed with a total of 20 cm³ of n-heptane and then dried under reduced pressure (13.5 Pa) at a temperature in the region of 40° C. 750 mg of N-[3β-hydroxy-20(29)-lupen-28-oyl]-11-amino-2,2-dimethylundecanoic acid are thus obtained, melting at a temperature in the region of 120° C.

Methyl 11-amino-2,2-dimethylundecanoate is prepared in the following way:

A solution of 15.4 g of methyl 11-phthalimido-2,2-dimethylundecanoate and 2.33 cm³ of 98% hydrazine hydrate in 500 cm³ of methanol is stirred for 12 hours at a temperature in the region of 20° C. 32 cm³ of 5N methanolic hydrochloric acid are added. The solvent is evaporated under reduced pressure (2.7 kPa) at a temperature in the region of 40° C. The residue is taken up in 150 cm³ of distilled water. After stirring for 20 minutes, the solid is separated by filtration and washed with a total of 90 cm³ of distilled water. The aqueous phase is brought to a pH in the region of 9–10 by means of a 10% sodium carbonate solution, extracted with a total of 500 cm³ of diisopropyl ether, dried over magnesium sulphate and then concentrated under reduced pressure (2.7 kPa) at a³ temperature in the region of 40° C. The residue is taken up in a mixture of 15 cm³ of methanol and 50 cm³ of diethyl ether. 10 cm³ of 5N methanolic hydrochloric acid are added and the mixture is evaporated to dryness under reduced pressure (2.7 kPa) at a temperature in the region of 40° C. The yellow oil obtained is taken up in 100 cm³ of distilled water. 2 cm³ of 4N hydrochloric acid are added and the mixture is then brought to a pH in the region of 9–10 by means of a 10% sodium carbonate solution. Extraction is carried out with a total of 450 cm³ of ethyl acetate. The organic phase is dried over magnesium sulphate and then concentrated to dryness under reduced pressure (13.5 Pa) at a temperature in the region of 40° C. 6.8 g of methyl 11-amino-2,2-dimethylundecanoate are thus obtained in the form of a viscous yellow oil [$R_f$=0.54; silica thin layer chromatography; eluent: chloroform/methanol/ 28% aqueous ammonia 24/6/1 (by volume)].

Methyl 11-phthalimido-2,2-dimethylundecanoate is obtained in the following way:

12.3 g of methyl 11-bromo-2,2-dimethylundecanoate in solution in 70 cm³ of N,N-dimethylformamide are added to 8.2 g of potassium phthalimide in 70 cm³ of N,N-dimethylformamide and the mixture is heated for 3 hours at a temperature in the region of 80° C. The solution is cooled to a temperature in the region of 20° C. and then poured into 1400 cm³ of distilled water. Acidification is carried out to a pH in the region of 2 using 4N hydrochloric acid and extraction is then carried out with a total of 1000 cm³ of ethyl acetate. The organic phase is washed with a total of 450 cm³ of distilled water, dried over magnesium sulphate, and then concentrated under reduced pressure (13.5 Pa) at a temperature in the region of 60° C. 15.4 g of methyl 11-phthalimido-2,2-dimethylundecanoate are thus obtained in the form of a pale yellow viscous oil [$R_f$=0.38; silica thin layer chromatography; eluent: cyclohexane/ethyl acetate 8/2 (by volume)].

Methyl 11-bromo-2,2-dimethylundecanoate was obtained in the following way:

110 cm³ of a 1.6M solution of n-butyllithium in hexane are added over 25 minutes to a solution of 25 cm³ of diisopropylamine in 90 cm³ of tetrahydrofuran cooled to a temperature in the region of –78° C. The mixture is left for 1 hour at a temperature in the region of –78° C. 18.5 cm³ of methyl isobutyrate are added over 25 minutes. The mixture is stirred for 1 hour at a temperature in the region of –70° C. before adding a solution of 70.4 g of 1,9-dibromononane in 45 cm³ of tetrahydrofuran over 15 minutes. The mixture is left to stir at a temperature in the region of –70° C. and then for 12 hours at a temperature in the region of 20° C. The mixture is concentrated under reduced pressure (2.7 kPa) at a temperature in the region of 40° C. 200 cm³ of 1N hydrochloric acid are added and then extraction is carried out by means of 250 cm³ of dichloromethane. The organic phase is washed successively with a total of 160 cm³ of 1N hydrochloric acid, a total of 160 cm³ of distilled water, 30 cm³ of a saturated aqueous sodium bicarbonate solution and finally a total of 80 cm³ of distilled water. The organic phase is dried over magnesium sulphate and then concentrated under reduced pressure (2.7 kPa) at a temperature in the region of 50° C. The 74 g of an orange oil obtained are distilled under reduced pressure (20 Pa) while collecting the fraction which distils between 120° and 130° C. 33.2 g are thus obtained of an oil which is redistilled under reduced pressure (10 Pa). The fraction is collected which distils between 114° and 122° C. 25 g of methyl 11-bromo-2,2-dimethylundecanoate are thus obtained.

EXAMPLE 20

A solution of 1 g of methyl N-[3-oxo-20(29)-lupen-28-oyl]-11-aminoundecanoate and 440 mg of methyl aminooxyacetate hydrochloride in 20 cm³ of pyridine is heated at reflux for 3 hours and then the solution is cooled to a temperature in the region of 20° C. and treated with 100 cm³ of distilled water and 50 cm³ of ethyl acetate. The organic phase is separated off, the aqueous phase is extracted with a total of 100 cm³ of ethyl acetate, the organic extracts are combined, washed with a total of 50 cm³ of distilled water, dried over anhydrous magnesium sulphate and evaporated under reduced pressure (2.7 kPa) at a temperature in the region of 35° C. The residue obtained is chromatographed on a column with a diameter of 5 cm containing 200 g of silica (0.02–0.045 mm) eluted with an 80/20 (by volume) mixture of cyclohexane and ethyl acetate, while collecting 30 cm³ fractions. The first 11 fractions are discarded; the following 16 are combined and concentrated under reduced pressure (2.7 kPa) at a temperature in the region of 35° C. 940 mg are thus obtained of an oil which is purified by 2-step HPLC, on a column with a diameter of 5 cm containing 300 g of $C_{18}$-grafted silica (0.015–0.025 mm), eluted with a 50/30/15 and then 65/20/15 (by volume) mixture of acetonitrile, water and tetrahydrofuran. The first 18 fractions are discarded, the following 2 are combined and concentrated to dryness under reduced pressure (13.5 Pa) at a temperature in the region of 35° C. 450 mg of methyl N-[3-(methoxycarbonylmethoxyimino)-20(29)-lupen-28-oyl]-11-aminoundecanoate are thus obtained in the form of a colourless lac [$R_f$=0.4; ethyl acetate (75/25 by volume)].

A solution of 454 mg of methyl N-[3-(methoxycarbonylmethoxyimino)-20(29)-lupen-28-oyl]-11-aminoundecanoate in 6 cm³ of methanol, 3 cm³ of tetrahydrofuran and 0.77 cm³ of 4N sodium hydroxide solution is stirred for 15 hours at a temperature in the region of 20° C. and acidified with 1 cm³ of 5N hydrochloric acid. After stirring for 2 hours, the solid is separated by filtration, washed with a total of 30 cm³ of distilled water and dried under reduced pressure (13.5 kPa) at a temperature in the region of 40° C. 320 mg of N-[3-(carboxymethoxyimino)-20(29)-lupen-28-oyl]-11-aminoundecanoic acid (mixture of Z and E isomers) are thus obtained in the form of a white solid melting around 100° C.

EXAMPLE 21

A solution of 1.35 g of methyl N-[3-oxo-20(29)-lupen-28-oyl]-11-aminoundecanoate and 210 mg of 2-(4-methyl-1-piperazinyl)ethoxyamine in 25 cm³ of pyridine is heated at reflux for 1 hour and the solution is then cooled to a temperature in the region of 20° C. 200 cm³ of distilled water are added, then 11 cm³ of 1N sodium hydroxide solution and 100 cm³ of ethyl acetate. The organic phase is separated off, the aqueous phase is extracted with a total of 200 cm³ of ethyl acetate, the organic extracts are combined, washed with a total of 60 cm³ of distilled water, dried over anhydrous magnesium sulphate and evaporated under reduced pressure (13.5 kPa) at a temperature in the region of 35° C. The residue obtained (1.65 g) is chromatographed on a column with a diameter of 5 cm containing 200 g of silica (0.02–0.045 mm) eluted with a 50/50 (by volume) mixture of ethyl acetate and methanol, while collecting 30 cm³ fractions. The first 17 fractions are discarded; the following 18 are combined and concentrated under reduced pressure (2.7 kPa) at a temperature in the region of 35° C. 1.34 g of methyl N-{3-[2-(4-methyl-1 -piperazinyl)ethoxyimino]-20(29)-lupen-28-oyl}-11-aminoundecanoate is thus obtained in the form of a white foam [$R_f$=0.3; silica thin layer chromatography; eluent: ethyl acetate/methanol 50/50 (by volume)].

A solution of 1.34 g of methyl N-{3-[2-(4-methyl-1-piperazinyl)ethoxyimino]-20(29)-lupen-28-oyl}-11-aminoundecanoate in 20 cm³ of methanol, 10 cm³ of tetrahydrofuran and 1.05 cm³ of 4N sodium hydroxide solution is stirred for 15 hours at a temperature in the region of 20° C. and the solvent is removed under reduced pressure (2.7 kPa) at a temperature in the region of 40° C. 25 cm³ of ethyl acetate are then added, the solid is separated by filtration and washed with a total of 15 cm³ of ethyl acetate. 760 mg of N-{3-[2-(4-methyl-1-piperazinyl)ethoxyimino]-20 (29)-lupen-28-oyl}-11-aminoundecanoic acid (mixture of Z and E isomers) are thus obtained in the form of a beige solid melting around 97° C.

EXAMPLE 22

A solution of 1 g of methyl N-[3β-acetoxy-20(29)-lupen-28-oyl]-11-aminoundecanoate in 50 cm³ of ethanol is hydrogenated, under atmospheric pressure and at a temperature in the region of 20° C., in the presence of 0.1 g of 5% (by weight) palladium-on-charcoal, for 4 hours. The catalyst is filtered, washed with a total of 30 cm³ of absolute ethanol and the filtrates are evaporated to dryness under reduced pressure (2.7 kPa) at a temperature in the region of 40° C. 810 mg are obtained of a colourless oil which is chromatographed on a column with a diameter of 4 cm containing 100 g of silica (0.02–0.045 mm) eluted with an 80/10/10 (by volume) mixture of cyclohexane, methylene chloride and ethyl acetate, while collecting 30 cm³ fractions. After discarding the first 17 fractions, the following 6 are combined and concentrated under reduced pressure (2.7 kPa) at a temperature in the region of 40° C. 600 mg of a 50/50 mixture of methyl and ethyl N-[3β-acetoxy-28-lupanoyl]-11-aminoundecanoate are obtained in the form of a colourless oil [$R_f$=0.5; silica thin layer chromatography; eluent: cyclohexane/ethyl acetate 80/20 (by volume)].

A solution of 600 mg of methyl N-[3β-acetoxy-28-lupanoyl]-11-aminoundecanoate in 4.3 cm³ of methanol and 8.5 cm³ of tetrahydrofuran is treated with 1 cm³ of 4N sodium hydroxide solution, stirred for 15 hours at a temperature in the region of 20° C., acidified to a pH in the region of 3–4 using 0.9 cm³ of 4N hydrochloric acid and diluted with 25 cm³ of distilled water. After stirring for 15 hours, the solid is separated by filtration, washed with a total of 50 cm³ of distilled water and dried under atmospheric pressure at a temperature in the region of 20° C. 410 mg of N-[3β-hydroxy-28-lupanoyl]-11-aminoundecanoic acid are thus obtained, melting around 110°–115° C.

EXAMPLE 23

A solution of 1.4 g of methyl N-(30-nor-3β-acetoxy-20-oxo-28-lupanoyl)-11-aminoundecanoate, 100 mg of sodium borohydride and 700 mg of tetrabutylammonium chloride in 120 cm³ of toluene is heated at a temperature in the region of reflux. After 9 hours, 100 mg of sodium borohydride and 700 mg of tetrabutylammoniumchloride are added and the temperature is maintained for 9 hours at a temperature in the region of reflux. After having once more added 100 mg of sodium borohydride and 700 mg of tetrabutylammonium chloride, the reaction mixture is heated for 24 hours at a temperature in the region of reflux. 1 cm³ of distilled water is added and the temperature is maintained. After 8 hours, 100 mg of sodium borohydride and 700 mg of tetrabutylammonium chloride are added 3 times successively at intervals of 8 hours. The solution is then stirred for 48 hours at a temperature in the region of 20° C. 50 cm³ of distilled water are then added over 1 hour. The organic phase is separated off, the aqueous phase is extracted with a total of 80 cm³ of ethyl acetate, the combined organic phases are washed with a total of 90 cm³ of distilled water, dried for 2 hours over anhydrous magnesium sulphate and evaporated to dryness under reduced pressure (2.7 kPa) at a temperature in the region of 45° C. The residue obtained is chromatographed on a column with a diameter of 3 cm containing 80 g of silica (0.02–0.045 mm) eluted with a 6/4 (by volume) mixture of cyclohexane and ethyl acetate while collecting 50 cm³ fractions. The first 12 fractions are combined and concentrated under reduced pressure (2.7 kPa) at a temperature in the region of 35° C. 800 mg are thus obtained of a solid which is dissolved in 20 cm³ of diethyl ether. The ethereal solution is washed successively with 10 cm³ of a 2N hydrochloric acid solution and then with 4 times 10 cm³ of distilled water. The organic phase is dried over anhydrous magnesium sulphate and concentrated to dryness under reduced pressure (2.7 kPa) at a temperature in the region of 40° C. 500 mg of methyl N-(30-nor-3β-acetoxy-20-hydroxy-28-lupanoyl)-11-aminoundecanoate are thus obtained in the form of a white foam.

A solution of 500 mg of methyl N-(30-nor-3β-acetoxy-20-hydroxy-28-lupanoyl)-11-aminoundecanoate in 10 cm³ of methanol, 5 cm³ of tetrahydrofuran and 5 cm³ of 4N sodium hydroxide solution is stirred for 12 hours at a temperature in the region of 20° C. The suspension is then acidified to a pH in the region of 1–2 using 4N hydrochloric acid and is then diluted by means of 20 cm³ of distilled water. After stirring for 30 minutes, the solid is separated by filtration, washed successively with 5 times 10 cm³ of distilled water and 3 times 5 cm³ of diethyl ether and then dried under reduced pressure (13.5 Pa) at a temperature in the region of 40° C. 400 mg are thus obtained of a solid which is dissolved in 5 cm³ of dioxane. 15 cm³ of distilled water are added to the solution obtained. The white solid obtained is filtered, washed with 2 times 3 cm³ of a 1/3 (by volume) dioxane/distilled water mixture and then dried under reduced pressure (13.5 Pa) at a temperature in the region of 40° C. 250 mg of N-(30-nor-3β-dihydroxy-28-lupanoyl)-11-aminoundecanoic acid are thus obtained, melting around 170° C.

EXAMPLE 24

0.7 cm³ of bromine is added to a solution of 2.6 g of sodium hydroxide in 18 cm³ of distilled water, cooled to −5° C. The reaction mixture is stirred for 15 minutes at −5° C. and then 12 cm³ of dioxane are added. The solution obtained is added, over approximately 10 minutes, to a solution of 2.3 g of methyl N-(30-nor-3β-acetoxy-20-oxo-28 -lupanoyl)-11-aminoundecanoate in 50 cm³ of dioxane. The solution is stirred at a temperature in the region of 10° C. for 15 hours and then a solution of 0.5 g of sodium sulphite in 5 cm³ of distilled water is added and the mixture is acidified to a pH in the region of 1 using 4N hydrochloric acid. After 30 minutes, the mixture is diluted with 50 cm³ of distilled water and the solid is separated by filtration, washed with a total of 50 cm³ of distilled water and dried in air under atmospheric pressure at a temperature in the region of 20° C. 2 g are thus obtained of a white solid which is dissolved in a mixture of 10 cm³ of dioxane and 5 cm³ of distilled water. The mixture is left for 48 hours at a temperature in the region of 20° C. The solid is filtered, rinsed successively with 2 cm³ of dioxane and 2 times 5 cm³ of diethyl ether and then dried under reduced pressure (13.5 Pa) at a temperature in the region of 40° C. 800 mg of N-(30-nor-3β-hydroxy-20-oxo-28-lupanoyl)-11-aminoundecanoic acid are thus obtained, melting around 160° C.

Methyl N-[30-nor-3β-acetoxy-20-oxo-28-lupanoyl]-11-aminoundecanoate can be prepared in the following way:

2.2 cm³ of triethylamine and 1.94 g of methyl 11-aminoundecanoate hydrochloride are added to 195 cm³ of a solution, in dichloromethane, of 30-nor-3β-acetoxy-20-oxo-28-lupanoyl chloride. The solution is then stirred for 72 hours at a temperature in the region of 20° C. The reaction mixture is diluted with 100 cm³ of distilled water. The organic phase is extracted with 3 times 150 cm³ of dichloromethane. The combined organic phases are dried for 3 hours over magnesium sulphate, the desiccating agent is filtered and rinsed with a total of 90 cm³ of dichloromethane. The combined organic phases are concentrated to dryness under reduced pressure (2.7 kPa) at a temperature in the region of 50° C. The 5.7 g of pale yellow oil obtained are chromatographed on a column with a diameter of 4 cm and a height of 60 cm, containing silica (0.02–0.045 mm) eluted successively with a 70/30 (by volume) mixture of cyclohexane and ethyl acetate for the fractions 1 to 50 and a 50/50 (by volume) mixture of cyclohexane and ethyl acetate for the following fractions. 100 cm³ fractions are collected. The first 30 fractions are discarded; the following 32 are combined and concentrated under reduced pressure (2.7 kPa) at a temperature in the region of 35° C. 5 g are thus obtained of a white foe which is triturated with 2 times 100 cm³ of diisopropyl ether and then dried under reduced pressure (2.7 kPa) at a temperature in the region of 40° C. 4.75 g of methyl N-(30-nor-3β-acetoxy-20-oxo-28 -lupanoyl)-11-aminoundecanoate are thus obtained in the form of a white foam [$R_f$=0.23; silica thin layer chromatography; eluent: cyclohexane/ethyl acetate 8/2 (by volume)].

30-Nor-3β-acetoxy-20-oxo-28-lupanoyl chloride is obtained in the following way:

1.5 cm³ of oxalyl chloride is added over 5 minutes to 150 cm³ of a solution in dichloromethane of 30-nor-3β-acetoxy-20-oxo-28-lupanoic acid. The solution is then stirred for 20 hours at a temperature in the region of 20° C. The reaction mixture is concentrated to dryness under reduced pressure (2.7 kPa) at a temperature in the region of 40° C. The white foam obtained is triturated with 2 times 200 cm³ of cyclohexane and the solvent is then evaporated to dryness under reduced pressure (2.7 kPa) at a temperature in the region of 40° C. 3.7 g of 30-nor-3β-acetoxy-20-oxo-28-lupanoyl chloride are thus obtained in the form of a white foam.

30-Nor-3β-acetoxy-20-oxo-28-lupanoic acid is prepared according to A. Vystrcil and M. Budesinsy, Collect. Czech. Chem. Commun., 35, 295 (1970).

EXAMPLE 25

420 mg of methyl 8-aminooctanoate hydrochloride, 240 mg of 1-hydroxybenzotriazole hydrate, 760 mg of 1-ethyl-3-(3-dimethylaminopropyl)carbodiimide hydrochloride and 1 cm³ of triethylamine are added to a solution of 1 g of N-[3β-acetoxy-20(29)-lupen-28-oyl]-β-alanine in 100 cm³ of dichloromethane. The solution is stirred for 12 hours at a temperature in the region of 20° C. and then 100 cm³ of distilled water are added. The organic phase is separated off and the aqueous phase is extracted with a total of 150 cm³ of methylene chloride. The organic extracts are combined, dried over anhydrous magnesium sulphate and concentrated to dryness under reduced pressure (2.7 kPa) at a temperature in the region of 35° C. The residue obtained (1.4 g) is chromatographed on a column with a diameter of 4 cm containing 125 g of silica (0.02–0.045 mm), eluted with a 60/40 (by volume) mixture of cyclohexane and ethyl acetate, while collecting 50 cm³ fractions. The first 36 fractions are discarded; the following 15 are combined and concentrated under reduced pressure (2.7 kPa) at a temperature in the region of 35° C. 1.1 g of methyl N-[N-(3β-acetoxy-20(29)-lupen-28-oyl)-3-aminopropionyl]-8-aminooctanoate is thus obtained in the form of a white foam [$R_f$=0.5; silica thin layer chromatography; eluent: methylene chloride/methanol 90/10 (by volume)].

A solution of 1.1 g of methyl N-[N-(3β-acetoxy-20(29)-lupen-28-oyl)-3-aminopropionyl]-8-aminooctanoate in 15 cm³ of methanol, 7.5 cm³ of tetrahydrofuran and 1.9 cm³ of 4N sodium hydroxide solution is stirred for 15 hours at a temperature in the region of 20° C. and then 20 cm³ of methanol, 3 cm³ of 5N hydrochloric acid and 50 cm³ of distilled water are added. After stirring for 30 minutes, the solid formed is separated by filtration, washed with a total of 50 cm³ of distilled water and dried under reduced pressure (13.5 Pa) at a temperature in the region of 40° C. 845 mg of N-[N-(3β-hydroxy-20(29)-lupen-28-oyl)-3-aminopropionyl]-8-aminooctanoic acid are thus obtained in the form of a white solid melting around 115° C.

N-[3β-Acetoxy-20(29)-lupen-28-oyl]-3-aminopropionic acid can be prepared in the following way:

After having heated a mixture of 190 mg of 3-aminopropionic acid and 410 mg of chlorotrimethylsilane in 50 cm³ of dichloromethane at reflux for 3 hours, the solution is cooled to around 20° C. and 1 g of 3-acetoxy-20(29)-lupen-28-oyl chloride in solution in 30 cm³ of dichloromethane is added and then 0.81 cm³ of triethylamine in solution in 15 cm³ of dichloromethane is added. Stirring is maintained for 15 hours at a temperature in the region of 20° C. and the solvent is evaporated to dryness under reduced pressure (2.7 kPa) at a temperature in the region of 35° C. The residue is chromatographed on a column with a diameter of 5 cm containing 250 g of silica (0.02–0.045 mm), eluted in the presence of a 90/10 (by volume) methylene chloride/methanol mixture, while collecting 50 cm³ fractions. The first 9 fractions are discarded, the following 15 are combined and concentrated to dryness under reduced pressure (2.7 kPa) at a temperature in the region of 35° C. 1.04 g of N-(3β-acetoxy-20(29)-lupen-28-oyl)-3-aminopropionic acid is thus obtained in the form of a white foam [$R_f$=0.3; silica thin layer chromatography; eluent: methylene chloride/methanol 90/10 (by volume)].

EXAMPLE 26

410 mg of methyl 8-aminooctanoate hydrochloride, 243 mg of 1-hydroxybenzotriazole hydrate, 690 mg of 1-ethyl-3-(3-dimethylaminopropyl)carbodiimide hydrochloride and 0.5 cm³ of triethylamine are added to a solution of 1 g of N-(3β-acetoxy-20(29)-lupen-28-oyl)glycine in 100 cm³ dichloromethane. The solution is stirred for 12 hours at a temperature in the region of 20° C. and then 100 cm³ of distilled water are added. The organic phase is separated off and the aqueous phase is extracted with a total of 150 cm³ of methylene chloride. The organic extracts are combined, dried over anhydrous magnesium sulphate and concentrated to dryness under reduced pressure (2.7 kPa) at a temperature in the region of 35° C. The residue obtained (1.26 g) is chromatographed on a column with a diameter of 5 cm containing 200 g of silica (0.02–0.045 mm), eluted with a 50/50 (by volume) mixture of cyclohexane and ethyl acetate while collecting 50 cm³ fractions. The first 17 fractions are discarded; the following 27 are combined and concentrated under reduced pressure (2.7 kPa) at a temperature in the region of 35° C. 1.2 g of methyl N-[N-(3β-acetoxy-20(29)-lupen-28-oyl)glycyl]-8-aminooctanoate is obtained in the form of a white foam [$R_f$=0.2; silica thin layer chromatography; eluent: cyclohexane/ethyl acetate 50/50 (by volume)].

A solution of 1.2 g of methyl N-[N-(3β-acetoxy-20(29)-lupen-28-oyl)glycyl]-8-aminooctanoate in 17 cm³ of methanol, 8.5 cm³ of tetrahydrofuran and 2.1 cm³ of 4N sodium hydroxide solution is stirred for 15 hours at a temperature in the region of 20° C. and then 20 cm³ of methanol, 4 cm³ of 5N hydrochloric acid, 50 cm³ of distilled water and 50 cm³ of ethyl acetate are added. The organic phase is separated off and the aqueous phase is extracted with a total of 200 cm³ of ethyl acetate. The organic extracts are combined, dried over anhydrous magnesium sulphate and evaporated to dryness under reduced pressure (2.7 kPa) at a temperature in the region of 35° C. The residue is dissolved in 4 cm³ of ethanol and 40 cm³ of distilled water are added. After stirring for 30 minutes, the solid is separated by filtration, washed with a total of 50 cm³ of distilled water and dried under reduced pressure (13.5 Pa) at a temperature in the region of 40° C. 883 mg of N-[N-(3β-hydroxy-20(29)-lupen-28-oyl)glycyl]-8-aminooctanoic acid are thus obtained in the form of a white solid, melting around 130° C.

N-(3β-Acetoxy-20(29)-lupen-28-oyl)glycine can be prepared in the following way:

After having heated a mixture of 830 mg of glycine and 2.28 g of chlorotrimethylsilane in 300 cm³ of dichloromethane at reflux for 6 hours 30 minutes, the solution is cooled to around 20° C. and 5.17 g of 3-acetoxy-20(29)-lupen-28-oyl chloride and then 3.54 cm³ of triethylamine are added. Stirring is maintained for 48 hours at a temperature in the region of 20° C. and the solvent is evaporated to dryness under reduced pressure (2.7 kPa) at a temperature in the region of 35° C. The residue is chromatographed on a column with a diameter of 5 cm containing 250 g of silica (0.02–0.045 mm), eluted with a 90/10 (by volume) methylene chloride/methanol mixture, while collecting 50 cm³ fractions. The first 10 fractions are discarded, the following 15 are combined and concentrated to dryness under reduced pressure (2.7 kPa) at a temperature in the region of 35° C. 1.04 g of N-(3β-acetoxy-20(29)-lupen-28-oyl)glycine is thus obtained in the form of a white foam [$R_f$=0.3; silica thin layer chromatography; eluent: methylene chloride/methanol 90/10 (by volume)].

EXAMPLE 27

250 mg of methyl glycinate hydrochloride, 240 mg of 1-hydroxybenzotriazole hydrate, 690 mg of 1-(3-dimethylaminopropyl)-3-ethylcarbodiimide hydrochloride and 0.5 cm³ of triethylamine are added to a solution of 1.13 g of N-(3β-acetoxy-20(29)-lupen-28-oyl)-8-aminooctanoic acid in 100 cm³ of dichloromethane. The solution is stirred for 12 hours at a temperature in the region of 20° C. and then 100 cm³ of distilled water are added. The organic phase is separated off and the aqueous phase is extracted with a total of 150 cm³ of methylene chloride. The organic extracts are combined, dried over anhydrous magnesium sulphate and evaporated to dryness under reduced pressure (2.7 kPa) at a temperature in the region of 35° C. The residue obtained (1.3 g) is chromatographed on a column with a diameter of 4 cm containing 125 g of silica (0.02–0.045 mm), eluted with a 30/70 (by volume) mixture of cyclohexane and ethyl acetate, while collecting 50 cm³ fractions. The first 15 fractions are discarded; the following 17 are combined and concentrated under reduced pressure (2.7 kPa) at a temperature in the region of 35° C. 1.2 g of methyl N-(3β-acetoxy-20(29)-lupen-28-oyl)-8-aminooctanoylglycinate is thus obtained in the form of a white foam [$R_f$=0.3; silica thin layer chromatography; eluent: cyclohexane/ethyl acetate 50/50 (by volume)].

A solution of 1.2 g of methyl N-[N-(3β-acetoxy-20(29)-lupen-28-oyl)-8-aminooctanoyl]glycinate in 17 cm³ of methanol, 8.5 cm³ of tetrahydrofuran and 2.1 cm³ of 4N sodium hydroxide solution is stirred for 15 hours at a temperature in the region of 20° C. and then 10 cm³ of methanol, 2.5 cm³ of 5N hydrochloric acid and 40 cm³ of distilled water are added. After stirring for 30 minutes, the solid is separated by filtration, washed with a total of 50 cm³ of distilled water and dried in air at a temperature in the region of 20° C. 1.03 g of N-[N-(3β-hydroxy-20(29)-lupen-28-oyl)-8-aminooctanoyl]glycine acid is thus obtained in the form of a white solid, melting around 132° C.

N-(3β-Acetoxy-20(29)-lupen-28-oyl)-8-aminooctanoic acid can be prepared in the following way:

After having heated a mixture of 330 mg of 8-aminooctanoic acid and 410 mg of chlorotrimethylsilane in 50 cm³ of dichloromethane at reflux for 3 hours, the solution is cooled to around 20° C. and 1 g of 3β-acetoxy-20(29)-lupen-28-oyl chloride and then 0.81 cm³ of triethylamine are added. Stirring is maintained for 15 hours at a temperature in the region of 20° C. and the solvent is evaporated to dryness under reduced pressure (2.7 kPa) at a temperature in the region of 35° C. The residue is chromatographed on a column with a diameter of 5 cm containing 200 g of silica (0.02–0.045 mm), eluted in the presence of the 60/40 (by volume) cyclohexane/ethyl acetate mixture, while collecting 50 cm³ fractions. The first 18 fractions are discarded, the following 31 are combined and concentrated to dryness under reduced pressure (2.7 kPa) at a temperature in the region of 35° C. 1.1 g of N-(3β-acetoxy-20(29)-lupen-28-oyl)-8-aminooctanoic acid is thus obtained in the form of a white foam [$R_f$=0.4; silica thin layer chromatography; eluent: cyclohexane/ethyl acetate 60/40 (by volume)].

EXAMPLE 28

0.4 g of methyl 4-aminophenylacetate and then 0.31 g of 1-hydroxybenzotriazole are added to a solution of 1.05 g of N-(3β-acetoxy-20(29)-lupen-28-oyl)-4-aminobutanoic acid in 60 cm³ of tetrahydrofuran. After stirring for 15 minutes at a temperature in the region of 20° C., 0.84 g of 1-(3-dimethylaminopropyl)-3-ethylcarbodiimide and then 1 cm³ of triethylamine are added. The solution is stirred for 240 hours at a temperature in the region of 20° C. The reaction mixture is evaporated under reduced pressure (2.7 kPa) at a temperature in the region of 40° C. 100 cm³ of dichloromethane are added to the residual pasty solid. The organic phase is washed with a total of 150 cm³ of distilled water, dried over magnesium sulphate and evaporated to dryness under reduced pressure (2.7 kPa) at a temperature in the region of 40° C. The cream solid obtained (1.4 g) is chromatographed on a column with a diameter of 2 cm and a height of 40 cm containing silica (0.02–0.045 mm) eluted with a 1/1 (by volume) mixture of cyclohexane and ethyl acetate, while collecting 70 cm³ fractions. The first 8 fractions are discarded, the following 2 are combined and concentrated under reduced pressure (2.7 kPa) at a temperature in the region of 40° C. 750 mg of methyl N-[N-(3β-acetoxy-20(29)-lupen-28-oyl)-4-aminobutanoyl]-4-aminophenylacetate are obtained in the form of a pale yellow viscous oil [$R_f$=0.69; silica thin layer chromatography; eluent: cyclohexane/ethyl acetate 1/1 (by volume)].

10 cm³ of 4N sodium hydroxide solution are added over approximately 5 minutes to a solution of 1.1 g of methyl N-[N-(3β-acetoxy-20(29)-lupen-28-oyl)-4-aminobutanoyl]-4-aminophenylacetate in 20 cm³ of methanol and 20 cm³ of tetrahydrofuran and the reaction mixture is stirred for 72 hours at a temperature in the region of 20° C. The reaction mixture is acidified to a pH in the region of 2 using 5N hydrochloric acid and then 100 cm³ of distilled water are added. After stirring for 3 hours, the solid is separated by filtration and rinsed with a total of 100 cm³ of distilled water. The solid is triturated with 30 cm³ of diisopropyl ether, filtered, rinsed with a total of 30 cm³ of diisopropyl ether and then dried under reduced pressure (13.5 Pa) at a temperature in the region of 40° C. 500 mg of N-[N-(3β-hydroxy-20(29)-lupen-28-oyl)-4-aminobutanoyl]-4-aminophenylacetic acid are thus obtained, melting at a temperature in the region of 190° C. (pasty).

N-(3β-Acetoxy-20(29)-lupen-28-oyl)-4-aminobutanoic acid can be obtained in the following way:

After having heated a mixture of 0.7 g of 4-aminobutyric acid and 1.68 cm³ of chlorotrimethylsilane in 180 cm³ of chloroform for 4 hours at reflux, the solution is cooled to around 20° C. and a solution of 3.3 g of 3-acetoxy-20(29)-lupen-28-oyl chloride in 90 cm³ of chloroform and then 3 cm³ of triethylamine are added. Stirring is maintained for 30 hours at a temperature in the region of 20° C. The reaction mixture is washed with a total of 450 cm³ of distilled water. The organic phase is dried over anhydrous magnesium sulphate and then evaporated to dryness under reduced pressure (2.7 kPa) at a temperature in the region of 35° C. The residue obtained (4.3 g) is chromatographed on a column with a diameter of 3 cm and a height of 40 cm containing silica (0.02–0.045 mm), eluted with a 95/5 (by volume) mixture of dichloromethane and methanol, while collecting 50 cm³ fractions. The first 6 fractions are discarded; the following 44 are combined and concentrated under reduced pressure (2.7 kPa) at a temperature in the region of 35° C. 2.3 g of N-[3β-acetoxy-20(29)-lupen-28-oyl]-4-aminobutanoic acid are thus obtained in the form of a white foam [$R_f$=0.51; silica thin layer chromatography; eluent: dichloromethane/methanol 9/1 (by volume)].

Methyl 4-aminophenylacetate can be obtained according to H. Salkowski, Chem. Ber., 28, 1917, (1895).

EXAMPLE 29

0.4 g of methyl 4-aminomethylbenzoate and then 0.31 g of 1-hydroxybenzotriazole are added to a solution of 1.05 g of N-(3β-acetoxy-20(29)-lupen-28-oyl)-4-aminobutanoic acid in 100 cm³ of tetrahydrofuran. After stirring for 15 minutes at a temperature in the region of 20° C., 0.84 g of 1-ethyl-3-(3-dimethylaminopropyl)carbodiimide hydrochloride and then 1 cm³ of triethylamine are added. The solution is stirred for 72 hours at a temperature in the region of 20° C. The reaction mixture is concentrated to dryness under reduced pressure (2.7 kPa) at a temperature in the region of 40° C. 100 cm³ of dichloromethane are added to the residual pasty solid. The organic phase is washed with a total of 150 cm³ of distilled water, dried over magnesium sulphate and concentrated to dryness under reduced pressure (2.7 kPa) at a temperature in the region of 40° C. The cream solid obtained (1.4 g) is chromatographed on a column with a diameter of 2 cm and a height of 40 cm containing silica (0.02–0.045 mm) eluted with a 1/1 (by volume) mixture of cyclohexane and ethyl acetate, while collecting 70 cm³ fractions. The first 15 fractions are discarded, the following 24 are combined and concentrated under reduced pressure (2.7 kPa) at a temperature in the region of 40° C. 1.15 g of methyl N-[N-(3β-acetoxy-20(29)-lupen-28-oyl)-4-aminobutanoyl]-4-aminomethylbenzoate is obtained in the form of a white foam [$R_f$=0.15; silica thin layer chromatography; eluent: cyclohexane/ethyl acetate 1/1 (by volume)].

15 cm³ of 4N sodium hydroxide solution are added over approximately 5 minutes to a solution of 1.1 g of methyl N-[N-(3β-acetoxy-20(29)-lupen-28-oyl)-4-aminobutanoyl]-4-aminomethylbenzoate in 30 cm³ of methanol and 30 cm³ of tetrahydrofuran and the reaction mixture is stirred for 24 hours at a temperature in the region of 20° C. The reaction mixture is acidified to a pH in the region of 2 using 5N hydrochloric acid and then 150 cm³ of distilled water are added. After stirring for 3 hours, the solid is separated by filtration and rinsed with a total of 150 cm³ of distilled water. The solid is triturated with 30 cm³ of diisopropyl ether, filtered, rinsed with a total of 75 cm³ of diisopropyl ether and then dried under reduced pressure (13.5 Pa) at a temperature in the region of 40° C. 900 mg of N-[N-(3β-hydroxy-20(29)-lupen-28-oyl)-4-aminobutanoyl]-4-aminomethylbenzoic acid are thus obtained, melting at a temperature in the region of 180°–190° C. (pasty).

Methyl 4-aminomethylbenzoate can be obtained in the following way:

3.3 cm³ of thionyl chloride are added over 10 minutes to 30 cm³ of methanol cooled to a temperature in the region of –30° C. Stirring is maintained for 30 minutes at a temperature in the region of –23° C. and then 4.7 g of 4-aminomethylbenzoic acid are added. The mixture is left to return to a temperature in the region of 20° C. over 1 hour. The mixture is treated with 15 cm³ of methanol and stirring is maintained for 15 hours at a temperature in the region of 20° C. The solid is separated by filtration, rinsed with a total of 90 cm³ of methanol and then with a total of 150 cm³ of diethyl ether. The solid is dried under reduced pressure (13.5 Pa) at a temperature in the region of 20° C. 3.2 g of methyl 4-aminomethylbenzoate hydrochloride are thus obtained in the form of a white solid melting at a temperature in the region of 270° C.

EXAMPLES 30 TO 49

The following derivatives were prepared by analogy with Example 27:

30) N'-[N-[3β-Hydroxy-20(29)-lupen-28-oyl]-8-aminooctanoyl]-β-alanine was prepared from N-[3β-acetoxy-20(29)-lupen-28-oyl]-8-aminooctanoic acid and methyl β-alaninate, M.p.=138° C., (Y=51%).

31) N'-[N-[3β-Hydroxy-20(29)-lupen-28-oyl]-8-aminooctanoyl]-L-aspartic acid was prepared from N-[3β-acetoxy-20(29)-lupen-28-oyl]-8-aminooctanoic acid and dibenzyl L-aspartate, M.p.=140° C., (Y=47%).

32) N'-[N-[3β-Hydroxy-20(29)-lupen-28-oyl]-8-aminooctanoyl]-L-phenylglycine was prepared from N-[3β-acetoxy-20(29)-lupen-28-oyl]-8-aminooctanoic acid and methyl L-phenylglycinate, M.p.=135° C., (Y=45%).

33) N'-[N-[3β-Hydroxy-20(29)-lupen-28-oyl]-8-aminooctanoyl]-L-alanine was prepared from N-[3β-acetoxy-20(29)-lupen-28-oyl]-8-aminooctanoic acid and benzyl L-alaninate, M.p.=120° C., (Y=34%).

34) N'-[N-[3β-Hydroxy-20(29)-lupen-28-oyl]-8-aminooctanoyl]-D-serine was prepared from N-[3β-acetoxy-20(29)-lupen-28-oyl]-8-aminooctanoic acid and methyl D-serinate, M.p.=252° C., (Y=8%).

35) Sodium N'-[N-[3β-hydroxy-20(29)-lupen-28-oyl]-8-aminooctanoyl]-L-homoserinate was prepared from N-[3β-acetoxy-20(29)-lupen-28-oyl]-8-aminooctanoic acid and α-amino-γ-butyrolactone, M.p.=130° C., (Y=45%).

36) N'-[N-[3β-Hydroxy-20(29)-lupen-28-oyl]-8-aminooctanoyl]-D,L-isoserine was prepared from N-[3β-acetoxy-20(29)-lupen-28-oyl]-8-aminooctanoic acid and methyl D,L-isoserinate, M.p.=140° C., (Y=56%).

37) N'-[N-[3β-Hydroxy-20(29)-lupen-28-oyl]-8-aminooctanoyl]-L-lysine was prepared from N-[3β-acetoxy-20(29)-lupen-28-oyl]-8-aminooctanoic acid and methyl N-trifluoroacetyl-L-lysinate, (Y=16%).

38) N'-[N-[3β-Hydroxy-20(29)-lupen-28-oyl]-8-aminooctanoyl]-L-asparagine was prepared from N-[3β-acetoxy-20(29)-lupen-28-oyl]-8-aminooctanoic acid and p-nitrobenzyl L-asparaginate, M.p.=120° C., (Y=34%).

39) N'-[N-[3β-Hydroxy-20(29)-lupen-28-oyl]-8-aminooctanoyl]sarcosine was prepared from N-[3β-acetoxy-20(29)-lupen-28-oyl]-8-aminooctanoic acid and ethyl sarcosinate, M.p.=120° C., (Y=85%).

40) N'-[N-[3β-Hydroxy-20(29)-lupen-28-oyl]-8-aminooctanoyl]-L-proline was prepared from N-[3β-acetoxy-20(29)-lupen-28-oyl]-8-aminooctanoic acid and methyl L-prolinate, M.p.=142° C., (Y=72%).

41) N'-[N-[3β-Hydroxy-20(29)-lupen-28-oyl]-8-aminooctanoyl]-L-phenylalanine was prepared from N-[3β-acetoxy-20(29)-lupen-28-oyl]-8-aminooctanoic acid and methyl L-phenylalaninate, M.p.=116° C., (Y=58%).

42) N'-[N-[3β-Hydroxy-20(29)-lupen-28-oyl]-8-aminooctanoyl]-L-valine was prepared from N-[3β-acetoxy-20(29)-lupen-28-oyl]-8-aminooctanoic acid and methyl L-valinate, M.p.=145° C., (Y=80%).

43) (2S,3S)-N'-[N-[3β-Hydroxy-20(29)-lupen-28-oyl]-8-aminooctanoyl]-3-amino-2-hydroxy-3-phenylpropionic acid was prepared from N-[3β-acetoxy-20(29)-lupen-28-oyl]-8-aminooctanoic acid and methyl (2S,3S)-3-amino-2-hydroxy-3-phenylpropionate, M.p.=120° C., (Y=58%).

44) N'-[N-[3β-Hydroxy-20(29)-lupen-28-oyl]-4-aminobutyryl]-6-aminohexanoic acid was prepared from N-[3β-acetoxy-20(29)-lupen-28-oyl]-4-aminobutyric acid and methyl 6-aminohexanoate, M.p.=140° C., (Y=100%). N-[3β-Acetoxy-20(29)-lupen-28-oyl]-4-aminobutyric acid was prepared from 3β-acetoxy-20(29)-lupen-28-oyl chloride and 4-aminobutyric acid [$R_f$=0.43; silica thin layer chromatography; eluent: methylene chloride/methanol 90/10 (by volume)].

45) N'-[N-[3β-Hydroxy-20(29)-lupen-28-oyl]-5-aminopentanoyl]-5-aminopentanoic acid was prepared from N-[3β-acetoxy-20(29)-lupen-28-oyl]-5-aminopentanoic acid and methyl 5-aminopentanoate, M.p.=132° C., (Y=85%). N-[3β-Acetoxy-20(29)-lupen-28-oyl]-5-aminopentanoic acid was prepared from 3β-acetoxy-20(29)-lupen-28-oyl chloride and 5-aminopentanoic acid [$R_f$=0.51; silica thin layer chromatography; eluent: methylene chloride/methanol 90/10 (by volume)].

46) N'-[N-[3β-Hydroxy-20(29)-lupen-28-oyl]-7-aminoheptanoyl]-3-aminoproponic acid was prepared from N-[3β-acetoxy-20(29)-lupen-28-oyl]-7-aminoheptanoic acid and methyl 3-aminopropionate, M.p.=194° C., (Y=36%). N-[3β-Acetoxy-20(29)-lupen-28-oyl]-7-aminoheptanoic acid was prepared from 3β-acetoxy-20(29)-lupen-28-oyl chloride and 7-aminoheptanoic acid [$R_f$=0.26; silica thin layer chromatography; eluent: cyclohexane/ethyl acetate 60/40 (by volume)].

47) N'-[N-[3β-Hydroxy-20(29)-lupen-28-oyl]-6-aminohexanoyl]-4-aminobutyric acid was prepared from N-[3β-acetoxy-20(29)-lupen-28-oyl]-6-aminohexanoic acid and methyl 4-aminobutyrate, M.p.=206° C., (Y=10%). N-[3β-Acetoxy-20(29)-lupen-28-oyl]-6-aminohexanoic acid was prepared from 3β-acetoxy-20(29)-lupen-28-oyl chloride and 6-aminohexanoic acid [$R_f$=0.2; silica thin layer chromatography; eluent: cyclohexane/ethyl acetate 60/40 (by volume)].

48) N'-[N-[3β-Hydroxy-20(29)-lupen-28-oyl]-8-aminooctanoyl]-3-aminopropionic acid was prepared from N-[3β-acetoxy-20(29)-lupen-28-oyl]-8-aminooctanoic acid and methyl 3-aminopropionate, M.p.=138° C., (Y=51%).

49) N'-[N-[3β-Hydroxy-20(29)-lupen-28-oyl]-8aminooctanoyl]-4-aminobutyric acid was prepared from N-[3β-acetoxy-20(29)-lupen-28-oyl]-8-aminooctanoic acid and methyl 4-aminobutyrate, M.p.=168° C., (Y=23%).

EXAMPLE 50

N'-N-[3β-Hydroxy-20(29)-lupen-28-oyl]-8-aminooctanoyl]-L-threonine can be obtained in the following way:

470 mg of benzyl L-threoninate hemioxalate, 240 mg of 1-hydroxybenzotriazole hydrate, 600 mg of 1-(3-dimethylaminopropyl)-3-ethylcarbodiimide hydrochloride and 0.88 cm³ of triethylamine are added, under a stream of argon, to a solution of 1 g of N-[3β-acetoxy-20(29)-lupen-28-oyl]-8-aminooctanoic acid in 50 cm³ of dichloromethane. The solution is stirred for 12 hours at a temperature in the region of 20° C. and then 60 cm³ of distilled water are added. The organic phase is separated off, dried over anhydrous magnesium sulphate and concentrated to dryness under reduced pressure (2.7 kPa) at a temperature in the region of 45° C. The residue obtained (1.36 g) is chromatographed on a column with a diameter of 4 cm containing 100 g of silica (0.02–0.045 mm), eluted with a 30/70 (by volume) mixture of cyclohexane and ethyl acetate while collecting 40 cm³ fractions. The first 10 fractions are discarded; the following 10 are combined and concentrated under reduced pressure (2.7 kPa) at a temperature in the region of 45° C. 1.12 g of a white foam is thus obtained which is dissolved in a mixture of 13.5 cm³ of methanol, 6.7 cm³ of tetrahydrofuran and 1.4 cm³ of 5N sodium hydroxide solution. After stirring for 15 hours at a temperature in the region of 20° C., 1.4 cm³ of 5N hydrochloric acid and 15 cm³ of distilled water are added. The methanol is removed under reduced pressure (2.7 kPa) at a temperature in the region of 45° C. After stirring for 30 minutes, the solid obtained is separated by filtration, washed with a total of 35 cm³ of distilled water and dried in air at a temperature in the region of 20° C. 880 mg of N'-[N-[3β-hydroxy-20(29)-lupen-28-oyl]-8-aminooctanoyl]-L-threonine is thus obtained in the form of a white solid, melting around 130° C.

EXAMPLE 51

N'-N-[3β-Hydroxy-20(29)-lupen-28-oyl]-8-aminooctanoyl]-L-statine can be obtained in the following way:

211 mg of methyl L-statinate hydrochloride, 105 mg of 1-hydroxybenzotriazole hydrate, 298 mg of 1-(3-dimethylaminopropyl)-3-ethylcarbodiimide hydrochloride and 0.38 cm³ of triethylamine are added to a solution of 500 mg of N-[3β-acetoxy-20(29)-lupen-28-oyl]-8-aminooctanoic acid in 30 cm³ of dichloromethane. The solution is stirred for 18 hours at a temperature in the region of 20° C. and then 50 cm³ of distilled water are added. The organic phase is separated off, dried over anhydrous magnesium sulphate and evaporated to dryness under reduced pressure (2.7 kPa) at a temperature in the region of 40° C. The residue obtained (570 mg) is dissolved in a mixture of 15 cm³ of methanol, 10 cm³ of tetrahydrofuran and 10 cm³ of 5N sodium hydroxide solution. After stirring for 15 hours at a temperature in the region of 20° C., 5 cm³ of methanol and then 10 cm³ of 5N hydrochloric acid and 5 cm³ of distilled water are added. The mixture is extracted with 60 cm³ of diethyl ether. The organic phase is separated off and washed with a total of 30 cm³ of distilled water, dried over anhydrous magnesium sulphate and concentrated to dryness under reduced pressure (4.0 kPa) at a temperature in the region of 40° C. The residue (520 mg) is suspended in 10 cm³ of diethyl ether. After stirring for 1 hour, the solid obtained is separated by filtration, washed with 5 cm³ of diethyl ether and dried under reduced pressure (13.5 Pa) at a temperature in the region of 20° C. 340 mg of N'-[N-[3β-hydroxy-20(29)-lupen-28-oyl]-8-aminooctanoyl]-L-statine are thus obtained in the form of a white solid, melting around 158° C.

Methyl L-statinate can be prepared according to the method described by Y. Takemoto et al., Tetrahedron Lett., 31 (2), 217, 1990.

EXAMPLE 52

The preparation is carried out by analogy with Example 11.

N-[3β,30-Dihydroxy-20(29)-lupen-28-oyl]-10-aminodecanoic acid was prepared from 3β,30-diacetoxy-20(29)-lupen-28-oyl chloride and methyl 10-aminodecanoate, M.p.=13°–140° C., (Y=14%).

EXAMPLE 53

The preparation is carried out by analogy with Example 11 and Example 27 and N'-[N-[3β,30-dihydroxy-20(29)-lupen-28-oyl]-8-aminooctanoyl]glycine is prepared, M.p.= 154° C., (Y=83%).

EXAMPLE 54

Methyl N-[3β,30-dihydroxy-20(29)-lupen-28-oyl]-10-aminodecanoate can be obtained in the following way:

A solution of 760 mg of N-[3β,30-dihydroxy-20(29)-lupen-28-oyl]-10-aminodecanoic acid, 0.48 cm³ of methyl iodide and 0.45 cm³ of 1,8-diazabicyclo[5.4.0]undec-7-ene in 6 cm³ of N,N-dimethylformamide is stirred for 4 hours at a temperature in the region of 20° C. After addition of 60 cm³ of distilled water and 25 cm³ of chloroform, the organic phase is separated off. The aqueous phase is extracted with a total of 25 cm³ of chloroform. The combined organic phases are dried over anhydrous sodium sulphate and concentrated to dryness under reduced pressure (2.7 kPa) at a temperature in the region of 40° C. The yellow oil obtained (1.34 g) is chromatographed on a column with a diameter of 3.2 cm containing 90 g of silica (0.02–0.04 mm) eluted with a 50/50 (by volume) mixture of dichloromethane and ethyl acetate while collecting 10 cm³ fractions. After discarding the first 52 fractions, the following 14 are combined and concentrated to dryness under reduced pressure (2.7 kPa) at a temperature in the region of 35° C. The 800 mg of foam obtained are dissolved in 8 cm³ of methanol and 8 cm³ of distilled water are added dropwise. After stirring for 30 minutes, the crystals obtained are separated by filtration, washed with a total of 10 cm³ of distilled water and dried under reduced pressure (13.5 Pa) at a temperature in the region of 30° C. 800 mg of methyl N-[3β,30-dihydroxy-20(29)-lupen-28-oyl]-10-aminodecanoate are thus obtained in the form of a white solid melting around 100° C.

EXAMPLES 55 AND 56

By carrying out the preparations by analogy with Example 54, the following products are prepared:
55) Methyl N'-[N-[3β,30-dihydroxy-20(29)-lupen-28-oyl]-8-aminooctanoyl]glycinate was prepared from N'-[N-[3β,30-dihydroxy-20(29)-lupen-28-oyl]-8-aminooctanoyl]glycine acid, M.p.=115° C., (Y=77%).
56) Methyl N'-[N-[3β-hydroxy-20(29)-lupen-28-oyl]-8-aminooctanoyl]glycinate was prepared from N'-[N-[3β-hydroxy-20(29)-lupen-28-oyl]-8-aminooctanoyl]glycine acid, M.p.=100° C. (Y=90%).

EXAMPLE 57

By carrying out the preparation by analogy with Example 19, the following product is prepared:
N-[3β,30-Dihydroxy-20(29)-lupen-28-oyl]-11-amino-2,2-dimethylundecanoic acid is prepared from methyl 11-amino-2,2-dimethylundecanoate and 3β,30-diacetoxy-20(29)-lupen-28-oic acid, M.p.=190° C.

EXAMPLE 58

N-[3β-Hydroxy-20(29)-lupen-28-oyl]-7-aminoheptylcarbamoylacetic acid can be obtained in the following way:

1.3 g of ethyl 7-aminoheptylcarbamoylacetate and then 1.1 cm³ of triethylamine are added, with stirring, to a solution of 3.5 g of 3β-acetoxy-20(29)-lupen-28-oyl chloride in 60 cm³ of chloroform. After stirring for 12 hours at a temperature in the region of 25° C., 50 cm³ of distilled water are added, the organic phase is separated off and the aqueous phase is extracted with a total of 25 cm³ of chloroform. The organic extracts are combined, washed with a total of 40 cm³ of distilled water, dried over anhydrous magnesium sulphate and the solvent is evaporated under reduced pressure (2.7 kPa) at a temperature in the region of 35° C. The beige foam obtained (1.8 g) is chromatographed on a column with a diameter of 3 cm containing 90 g of silica (0.02–0.045 mm), eluted with a 75/25 (by volume) mixture of ethyl acetate and cyclohexane, while collecting 10 cm³ fractions. The first 42 fractions are discarded, the following 15 are combined and concentrated under reduced pressure (2.7 kPa) at a temperature in the region of 35° C. The residue obtained (830 mg) is dissolved in a mixture of 8 cm³ of methanol, 4 cm³ of tetrahydrofuran and 2.75 cm³ of 4N sodium hydroxide solution. After stirring for 12 hours at a temperature in the region of 25° C., the solvent is evaporated to dryness under reduced pressure (2.7 kPa) at a temperature in the region of 35° C. The residue is taken up in 40 cm³ of distilled water and acidified using 3 cm³ of 4N hydrochloric acid. The crystals obtained are separated by filtration, washed with a total of 90 cm³ of distilled water and dried under reduced pressure (13.5 Pa) at a temperature in the region of 35° C. 670 mg of N-[3β-hydroxy-20(29)-lupen-28-oyl]-7-aminoheptylcarbamoylacetic acid are thus obtained in the form of a white solid, melting around 140° C.

Ethyl 7-aminoheptylcarbamoylacetate can be prepared in the following way:

1.3 cm³ of ethyl malonate chloride is added dropwise to a mixture of 3.4 g of mono-N-benzyloxycarbonyl-1,7-heptyldiamine and 1.68 cm³ of triethylamine in 120 cm³ of tetrahydrofuran and the solution is stirred for 48 hours at a temperature in the region of 25° C. After addition of 400 cm³ of distilled water and 200 cm³ of chloroform, the organic phase is separated off and the aqueous phase is extracted with a total of 400 cm³ of chloroform. The organic extracts are combined, washed with a total of 400 cm³ of distilled water, dried over anhydrous sodium sulphate and evaporated under reduced pressure (12.7 kPa) at a temperature in the region of 35° C. The orange-coloured oil obtained (4.0 g) is chromatographed on a column with a diameter of 3.5 cm containing 200 g of silica (0.02–0.045 mm), eluted with ethyl acetate, while collecting 15 cm³ fractions. The first 47 fractions are discarded, the following 17 are combined and concentrated under reduced pressure (2.7 kPa) at a temperature in the region of 35° C. The yellow oil obtained (1.62 g) is dissolved in a mixture of 5 cm³ of acetic acid and 5 cm³ of 30% hydrobromic acid (in solution in acetic acid) and is stirred for 15 minutes at a temperature in the region of 25° C. The solvent is removed under reduced pressure (2.7 kPa) at a temperature in the region of 45° C. 1.23 g of ethyl 7-aminoheptylcarbamoylacetate is thus obtained in the form of a thick honey-like residue used as it is.

Mono-(N-benzyloxycarbonyl)-1,7-heptyldiamine can be prepared in the following way:

2 g of ammonium chloride, 5.2 g of 1-hydroxybenzotriazole hydrate, 13 g of 1-(3-dimethylaminopropyl)-3-ethylcarbodiimide hydrochloride and 9.6 cm³ of triethylamine are added to a solution of 10 g of N-benzyloxycarbonyl-8-aminocaprylic acid in 500 cm³ of methylene chloride. The solution is stirred for 18 hours at a temperature in the region of 20° C. and then 1 liter of distilled water and 12 cm³ of 4N hydrochloric acid are added. The organic phase is separated off and the aqueous phase is extracted with a total of 200 cm³ of chloroform. The organic extracts are combined, washed with a total of 200 cm³ of distilled water, dried over anhydrous magnesium sulphate and evaporated to dryness under reduced pressure (2.7 kPa) at a temperature in the region of 35° C. The white powder obtained (7.1 g) is dissolved in a mixture of 92 cm³ of acetonitrile and 30 cm³ of distilled water and 3.6 g of [bis(trifluoroacetoxy)iodo]benzene are added. After stirring for 24 hours at a temperature in the region of 20° C., 400 cm³ of distilled water, 120 cm³ of 4N aqueous ammonia and 100 cm³ of chloroform are added. The organic phase is separated off and the aqueous phase is extracted with a total of 200 cm³ of chloroform. The organic extracts are combined, washed with 100 cm³ of distilled water, dried over anhydrous magnesium sulphate and concentrated to dryness under reduced pressure (2.7 kPa) at a temperature in the region of 35° C. 3.47 g of mono-(N-benzyloxycarbonyl)-1,7-heptyldiamine are thus obtained in the form of an orange-coloured oil [$R_f$=0.5; silica thin layer chromatography; eluent: chloroform/methanol/20% aqueous ammonia, 12/3/0.5 (by volume)].

N-Benzyloxycarbonyl-8-aminocaprylic acid can be prepared according to: A. Kapoor and L. W. Gerencser, J. Pharmac. Sci., 1969, 58(8), 976.

EXAMPLE 59

N-[3β-Hydroxy-30-(2'-hydroxyethyl)-thio-20(29)-lupen-28-oyl]-11-aminoundecanoic acid is prepared in the following way:

By carrying out the preparation by analogy with Example 7, methyl N-[3β-acetoxy-30-(2'-acetoxyethyl)thio-20(29)-lupen-28-oyl]-11-aminoundecanoate is prepared from 3β-acetoxy-30-(2'-acetoxyethyl)thio-20(29)-lupen-28-oyl chloride. 3.1 cm³ of 4N sodium hydroxide solution are added to a solution of 250 mg of methyl N-[3β-acetoxy-30-(2'-acetoxyethyl)thio-20 (29)-lupen-28-oyl]-11-aminoundecanoate in 20 cm³ of tetrahydrofuran and 10 cm³ of methanol. The reaction mixture is stirred for 12 hours at a temperature in the region of 20° C. and then acidified to a pH in the region of 3 by means of 4N hydrochloric acid and then diluted using 200 cm³ of distilled water. After stirring for 2 hours, the solid is separated by filtration, washed with a total of 90 cm³ of distilled water and then dried under reduced pressure (10 kPa) at a temperature in the region of 40° C. 150 mg of N-[3β-hydroxy-30-(2'-hydroxyethyl)thio-20-(29)-lupen-28 -oyl]-11-aminoundecanoic acid are thus obtained in the form of a white solid melting at a temperature in the region of 170° C.

The chloride of 3β-acetoxy-30-(2'-acetoxyethyl)thio-20(29)-lupen-28-oic acid is prepared in a way analogous to that described in Example 11: there are thus obtained, from 300 mg of 3β-acetoxy-30-(2'-acetoxyethyl)thio-20(29)-lupen-28-oic acid, 350 mg of a colourless lac which is used without any other purification.

3β-Acetoxy-30-(2'-acetoxyethyl)thio-20(29)-lupen-28-oic acid can be obtained in the following way:

A mixture of 400 mg of 3β-hydroxy-30-(2'-hydroxyethyl)thio-20(29)-lupen-28-oic acid, 930 mg of sodium acetate and 4.3 cm³ of acetic anhydride is heated for 15 minutes at reflux. 4.3 cm³ of acetic anhydride are added and the mixture is heated at reflux for 15 minutes. The mixture is cooled to a temperature in the region of 5° C. and 50 cm³ of distilled water are added dropwise over approximately 3 hours. After stirring for 12 hours at a temperature in the region of 25° C., the solid formed is separated by filtration, washed with a total of 50 cm³ of distilled water and dried under vacuum (20 kPa) at a temperature in the region of 25° C. The 500 mg of cream-white solid obtained are suspended in 30 cm³ of ethanol. 3 cm³ of aqueous ammonia (density 0.8) are added. The mixture is stirred for 12 hours at a temperature in the region of 25° C. The solvent is evaporated under reduced pressure (2.7 kPa). The residue is chromatographed on a column with a diameter of 2 cm containing 200 g of silica (0.02–0.045 mm, eluted with a 7/3 (by volume) mixture of cyclohexane and ethyl acetate while collecting 10 cm³ fractions. The first 18 fractions are discarded, the following 7 are combined and evaporated to dryness under reduced pressure (2.7 kPa) at a temperature in the region of 35° C. 300 mg of 3β-acetoxy-30-(2'-acetoxyethyl)thio-20 (29)-lupen-28-oic acid are thus obtained in the form of a white solid [$R_f$=0.49; silica thin layer chromatography; eluent: cyclohexane/ethyl acetate 7/3 (by volume)].

3β-Hydroxy-30-(2'-hydroxyethyl)thio-20(29)-lupen-28-oic acid can be prepared in the following way:

After having stirred a solution of 215 mg of 2-hydroxyethanethiol and 200 mg of sodium ethoxide in 15 cm³ of ethanol for 3 hours at a temperature in the region of 25° C., the mixture is concentrated to dryness under reduced pressure (2.7 kPa) at a temperature in the region of 40° C. 20 cm³ of tetrahydrofuran and 480 mg of 3β-hydroxy-30-bromo-20(29)-lupen-28-oic acid are added successively to the residual solid. The suspension obtained is stirred for 48 hours at a temperature in the region of 25° C. and then 10 cm³ of distilled water are added. The mixture is acidified to a pH in the region of 2 using a 2N aqueous hydrochloric acid solution and then diluted by means of 300 cm³ of distilled water. The white solid formed is separated by filtration, washed successively with a total of 300 cm³ of distilled water and 25 cm³ of diethyl ether. The white solid obtained is dried under reduced pressure (20 kPa) at a temperature in the region of 35° C. 400 mg of 3β-hydroxy-30-(2'-hydroxyethyl)thio-20(29)-lupen-28-oic acid are thus obtained in the form of a white solid melting at a temperature in the region of 220° C.

EXAMPLES 60 AND 61

By carrying out the preparations in a way analogous to Example 59, the following derivatives were prepared:

60) N-[3β-Hydroxy-30-methylthio-20(29)-lupen-28-oyl]-11-aminoundecanoic acid from 3β-hydroxy-30-bromo-20(29)-lupen-28-oic acid and methanethiol, M.p.=148° C.
61) N-[3β-Hydroxy-30-(2'-acetylaminoethyl)thio-20(29)-lupen-28-oyl]-11-aminoundecanoic acid from 3β-hydroxy-30-bromo-20(29)-lupen-28-oic acid and N-acetylaminoethanethiol, M.p.=150° C.

EXAMPLE 62

N-[3β-Hydroxy-30-diethylamino-20(29)-lupen-28-oyl]-11-aminoundecanoic acid is prepared in the following way:

Methyl N-[3β-acetyl-30-diethylamino-20(29)-lupen-28-oyl]-11-aminoundecanoate is prepared in a way analogous to that described in Example 11 from methyl 11-aminoundecanoate hydrochloride and 3β-acetyl-30-diethylamino-20(29)-lupen-28-oic acid.

2.4 cm³ of 1N sodium hydroxide solution are added to a solution of 450 mg of methyl N-[3β-acetyl-30-diethylamino-20(29)-lupen-28-oyl]-11 -aminoundecanoate in 10 cm³ of methanol and 5 cm³ of tetrahydrofuran. The reaction mixture is stirred for 12 hours at a temperature in the region of 20° C., then acidified to a pH in the region of 4–5 by means of solid citric acid and then diluted with 100 cm³ of distilled water. The aqueous phase is extracted with a total of 100 cm³ of chloroform. The combined organic phases are washed with a total of 75 cm³ of distilled water and then dried over magnesium sulphate. The solvent is evaporated under reduced pressure (2.7 kPa) at a temperature in the region of 50° C. The residue (400 mg) is chromatographed on a column with a diameter of 2.8 cm, containing 40 g of silica (0.02–0.045 mm), eluted with a 24/6/1 (by volume) mixture of chloroform, methanol and aqueous ammonia, while collecting 20 cm³ fractions. The first 4 fractions are discarded, the following 6 are combined and evaporated to dryness under reduced pressure (2.7 kPa) at a temperature in the region of 35° C. The residue obtained is taken up in 8 cm³ of acetonitrile. The solid obtained is separated by filtration, washed with a total of 4 cm³ of acetonitrile and dried under reduced pressure (2.7 kPa) at a temperature in the region of 40° C. 140 mg of N-[3β-hydroxy-30-diethylamino-20(29)-lupen-28-oyl]-11-aminoundecanoic acid are thus obtained in the form of a white solid, M.p.=130° C.

3β-Acetyl-30-diethylamino-20(29)-lupen-28-oic acid can be prepared in the following way:

A solution of 200 mg of methyl 3β-acetyl-30-diethylamino-20(29)-lupen-28-oate and 800 mg of lithium iodide in 60 cm³ of collidine is heated for 8 hours at a temperature in the region of reflux. The solvent is evaporated under reduced pressure (15 Pa) at a temperature in the region of 70° C. The residue is taken up in 50 cm³ of dichloromethane. The organic phase is washed with a total of 100 cm³ of distilled water. The organic phase is dried over magnesium sulphate and concentrated to dryness under reduced pressure (2.7 kPa) at a temperature in the region of 35° C. 152 mg of 3β-acetyl-30-diethylamino-20(29)-lupen-28-oic acid are thus obtained which is used without any other purification.

Methyl 3β-acetyl-30-diethylamino-20(29)-lupen-28-oate can be obtained in the following way:

30 mg of palladium acetate, 140 mg of triphenylphosphine and 0.02 cm³ of triethylamine are added to 30 cm³ of tetrahydrofuran. The mixture is left to stir for 30 minutes at a temperature in the region of 25° C. The yellow solid obtained is added to a solution of 770 mg of methyl 3β-acetyl-30-bromo-20(29)-lupen-28-oate, 70 cm³ of tetrahydrofuran and 0.4 cm³ of diethylamine. The reaction mixture is heated for 30 hours at a temperature in the region of reflux. After evaporation of the solvent under reduced pressure (2.7 kPa) at a temperature in the region of 40° C., the residual solid is taken up in 50 cm³ of dichloromethane. The organic phase is washed with a total of 45 cm³ of distilled water, dried over anhydrous magnesium sulphate and then evaporated under reduced pressure (2.7 kPa) at a temperature in the region of 40° C. The residue is chromatographed on a column with a diameter of 2.3 cm containing 60 g of silica (0.02–0.045 mm) eluted with a 9/1 (by volume) mixture of chloroform and methanol while collecting 15 cm³ fractions. The first 8 fractions are discarded, the following 50 are combined and concentrated to dryness under reduced pressure (2.7 kPa) at a temperature in the region of 35° C. 400 mg of methyl 3β-acetyl-30-diethylamino-20(29)-lupen-28-oate are thus obtained.

Methyl 3β-acetyl-30-bromo-20(29)-lupen-28-oate was synthesised according to B. Pradham, Indian J. Chem., 22B, 1983, 12–16.

EXAMPLES 63 TO 65

The following derivatives were prepared in a way analogous to the method described in Example 62.
63) N-[3β-Hydroxy-30-pyrrolidino-20(29)-lupen-28-oyl]-11-aminoundecanoic acid is prepared from methyl 3β-acetyl-30-bromo-20(29)-lupen-28-oate and pyrrolidine, M.p.=146° C.
64) N-[3β-Hydroxy-30-(2'-hydroxyethylamino)-20(29)-lupen-28-oyl]-11-aminoundecanoic acid is prepared from methyl 3β-acetyl-30-bromo-20(29)-lupen-28-oate and 2-acetyloxyethanamine, M.p.=214° C.
65) N-[3β-Hydroxy-30-(4'-methylpiperazino)-20(29)-lupen-28-oyl]-11-aminoundecanoic acid is prepared from methyl 3β-acetyl-30-bromo-20(29)-lupen-28-oate and N-methylpiperazine, M.p.=160° C.

EXAMPLE 66

N-[30-Acetoxy-3β-hydroxy-20(29)-lupen-28-oyl]-11-aminoundecanoic acid;
N'-[N-[3β-Hydroxy-20(29)-lupen-28-oyl]-8-aminooctanoyl]-2-aminoisobutyric acid;
N'-[N-[3β-Hydroxy-20(29)-lupen-28-oyl]-8-aminooctanoyl]-4-amino-3 (R,S)-hydroxybutyric acid;
(3S,4S)-N'-[N-[3β-Hydroxy-20(29)-lupen-28-oyl]-8-aminooctanoyl]-4-amino-4-benzyl-3-hydroxybutyric acid;
(3R,4S)-N'-[N-[3β-Hydroxy-20(29)-lupen-28-oyl]-8-aminooctanoyl]-4-amino-4-cyclohexylmethyl-3-hydroxybutyric acid;
(2S,5R)-N'-[N-[3β-Hydroxy-20(29)-lupen-28-oyl]-8-aminooctanoyl]-5-hydroxy-2-piperidinecarboxylic acid;
3-[[N-[3β-Hydroxy-20(29)-lupen-28-oyl]-7-aminoheptylcarbamoyl]propionic acid;
3-[[N-[3β-Hydroxy-20(29)-lupen-28-oyl]-7-aminoheptylcarbamoyl]-2(R)-hydroxypropionic acid;
3-[[N-[3β-Hydroxy-20(29)-lupen-28-oyl]-7-aminoheptylcarbamoyl]-2(S)-hydroxypropionic acid;
3-[[N-[3β-Hydroxy-20(29)-lupen-28-oyl]-7-aminoheptylcarbamoyl]-2 (R,S)-hydroxypropionic acid;
3-[[N-[3β-Hydroxy-20(29)-lupen-28-oyl]-7-aminoheptylcarbamoyl]-3(R)-hydroxypropionic acid;
3-[[N-[3β-Hydroxy-20(29)-lupen-28-oyl]-7-aminoheptylcarbamoyl]-3(S)-hydroxypropionic acid;
3-[N-[3β-Hydroxy-20(29)-lupen-28-oyl]-7-aminoheptylcarbamoyl-3(R,S)-hydroxypropionic acid;
3-[[N-[3β-Hydroxy-20(29)-lupen-28-oyl]-7-aminoheptylcarbamoyl]-2(R),3 (R)-dihydroxypropionic acid;
3-[[N-[3β-Hydroxy-20(29)-lupen-28-oyl]-7-aminoheptylcarbamoyl]-2(S),3 (S)-dihydroxypropionic acid;
3-[[N-[3β-Hydroxy-20(29)-lupen-28-oyl]-7-aminoheptylcarbamoyl]-2(R),3 (S)-dihydroxypropionic acid;
3-[[N-[3β-Hydroxy-20(29)-lupen-28-oyl]-7-aminoheptylcarbamoyl]-2(S),3 (R)-dihydroxypropionic acid;
4-[N-[3β-Hydroxy-20(29)-lupen-28-oyl]-7-aminoheptylcarbamoyl]butyric acid;
4-[N-[3β-Hydroxy-20(29)-lupen-28-oyl]-7-aminoheptylcarbamoyl]-4(R)-hydroxybutyric acid;
4-[N-[3β-Hydroxy-20(29)-lupen-28-oyl]-7-aminoheptylcarbamoyl]-4(S)-hydroxybutyric acid;
4-[N-[3β-Hydroxy-20(29)-lupen-28-oyl]-7-aminoheptylcarbamoyl]-4(R,S)-hydroxybutyric acid;
4-[N-[3β-Hydroxy-20(29)-lupen-28-oyl]-7-aminoheptylcarbamoyl]-2(R)-hydroxybutyric acid;
4-[N-[3β-Hydroxy-20(29)-lupen-28-oyl]-7-aminoheptylcarbamoyl]-2(S)-hydroxybutyric acid;
4-[N-[3β-Hydroxy-20(29)-lupen-28-oyl]-7-aminoheptylcarbamoyl]-2(R,S)-hydroxybutyric acid;
4-[N-[3β-Hydroxy-20(29)-lupen-28-oyl]-7-aminoheptylcarbamoyl]-2(R,S)-phenylbutyric acid;
4-[N-[3β-Hydroxy-20(29)-lupen-28-oyl]-7-aminoheptylcarbamoyl]-3(R,S)-phenylbutyric acid;
4-[N-[3β-Hydroxy-20(29)-lupen-28-oyl]-7-aminoheptylcarbamoyl]-4(R,S)-phenylbutyric acid;
4-[N-[3β-Hydroxy-20(29)-lupen-28-oyl]-7-aminoheptylcarbamoyl]-3(R,S)-methylbutyric acid;
4-[N-[3β-Hydroxy-20(29)-lupen-28-oyl]-7-aminoheptylcarbamoyl]-3(R,S)-hydroxybutyric acid;
4-[N-[3β-Hydroxy-20(29)-lupen-28-oyl]-7-aminoheptylcarbamoyl]-3,3-dimethylbutyric acid;
4-[N-[3β-Hydroxy-20(29)-lupen-28-oyl]-7-aminoheptylcarbamoyl]-2,2-dimethylbutyric acid;
4-[N-[3β-Hydroxy-20(29)-lupen-28-oyl]-7-aminoheptylcarbamoyl]-4,4-dimethylbutyric acid;
3(R,S)-4-[N-[3β-Hydroxy-20(29)-lupen-28-oyl]-7-aminoheptylcarbamoyl]-3-hydroxy-3-methylbutyric acid;
3(R,S),4(R,S)-4-[N-[3β-Hydroxy-20(29)-lupen-28-oyl]-7-aminoheptylcarbamoyl]-3,4-dihydroxybutyric acid;
2(R,S),3(R,S)-4-[N-[3β-Hydroxy-20(29)-lupen-28-oyl]-7-aminoheptylcarbamoyl]-2,3-dihydroxybutyric acid;
3(R,S),4(R,S)-4-[N-[3β-Hydroxy-20(29)-lupen-28-oyl]-7-aminoheptylcarbamoyl]-4-isobutyl-3-hydroxybutyric acid;
[N-[3β,30-Dihydroxy-20(29)-lupen-28-oyl]-7-aminoheptylcarbamoyl]acetic acid;
N-[3β-Hydroxy-20(29)-lupen-28-oyl]-11-amino-2(R,S)-methylundecanoic acid;
N'-[N-[3β,30-Dihydroxy-20(29)-lupen-28-oyl]-8-aminooctanoyl]-L-statine;
N'-[N-[3β,30-Dihydroxy-20(29)-lupen-28-oyl]-8-aminooctanoyl]-L-serine;
N'-[N-[3β,30-Dihydroxy-20(29)-lupen-28-oyl]-8-aminooctanoyl]-L-threonine;

N'-[N-[3β-Hydroxy-20(29)-lupen-28-oyl]-7-aminoheptanoyl]-L-statine;
N'-[N-[3β-Hydroxy-20(29)-lupen-28-oyl]-7-aminoheptanoyl]-L-threonine;
N'-[N-[3β-Hydroxy-20(29)-lupen-28-oyl]-7-aminoheptanoyl]-L-serine;
N'-[N-[3β-Hydroxy-20(29)-lupen-28-oyl]-11-aminoundecanoyl]glycine;
N'-[N-[3β-Hydroxy-20(29)-lupen-28-oyl]-11-aminoundecanoyl]-L-statine;
N'-[N-[3β-Hydroxy-20(29)-lupen-28-oyl]-11-aminoundecanoyl]-L-threonine;
N'-[N-[3β-Hydroxy-20(29)-lupen-28-oyl]-11-antinoundecanoyl]-L-serine;
N'-[N-[3β-Hydroxy-20(29)-lupen-28-oyl]-11-aminoundecanoyl]-D-statine;
N'-[N-[3β-Hydroxy-20(29)-lupen-28-oyl]-8-aminooctanoyl]-D-statine;
N'-[N-[3β-Hydroxy-30-(2'-hydroxyethyl)thio-20(29)-lupen-28-oyl]-8-aminooctanoyl] glycine;
N'-[N-[3β-Hydroxy-30-(2'-hydroxyethyl)thio-20(29)-lupen-28-oyl]-8-aminooctanoyl] -L-statine;
N'-[N-[3β-Hydroxy-30-(2'-hydroxyethyl)thio-20(29)-lupen-28-oyl]-8 -aminooctanoyl]-L-threonine;
N'-[N-[3β-Hydroxy-30-(2'-hydroxyethyl)thio-20(29)-lupen-28-oyl]-8 -aminooctanoyl]-L-serine;
N-[3β-Hydroxy-30-methoxy-20(29)-lupen-28-oyl]-11-aminoundecanoic acid;
N-[30-(tert-Butyloxy)-3β-hydroxy-20(29)-lupen-28-oyl]-11-aminoundecanoic acid;
N-[3β-Hydroxy-30-(2',3'-dihydroxypropyl)oxy-20(29)-lupen-28-oyl]-11-aminoundecanoic acid;
N-[3β-Hydroxy-30-(2'-hydroxyethyl)oxy-20(29)-lupen-28-oyl]-11-aminoundecanoic acid;
N-[3β-Hydroxy-30-(2',3'-dihydroxypropyl)thio-20(29)-lupen-28-oyl]-11 -aminoundecanoic acid;
N-[3β-Hydroxy-20(29)-lupen-28-oyl]-3-(8-aminooctamido)phenylacetic acid;
N-[3β-Hydroxy-20(29)-lupen-28-oyl]-4-(8-aminooctamido)phenylacetic acid;
N-[3β-Hydroxy-20(29)-lupen-28-oyl]-2-(8-aminooctamido)phenylacetic acid;
N-[3β-Hydroxy-20(29)-lupen-28-oyl]-3-(11-aminoundecanamido)phenylacetic acid;
N-[3β-Hydroxy-20(29)-lupen-28-oyl]-4-(11-aminoundecanamido)phenylacetic acid;
N-[3β-Hydroxy-20(29)-lupen-28-oyl]-2-(11-aminoundecanamido)phenylacetic acid;
N-[3β-Hydroxy-20(29)-lupen-28-oyl]-3-(8-aminooctamido)methylbenzoic acid;
N-[3β-Hydroxy-20(29)-lupen-28-oyl]-2-(8-aminooctamido)methylbenzoic acid;
N-[3β-Hydroxy-20(29)-lupen-28-oyl]-4-(8-aminooctamido)methylbenzoic acid;
N-[3β-Hydroxy-20(29)-lupen-28-oyl]-3-(11-aminoundecanamido)methylbenzoic acid;
N-[3β-Hydroxy-20(29)-lupen-28-oyl]-2-(11-aminoundecanamido)methylbenzoic acid;
N-[3β-Hydroxy-20(29)-lupen-28-oyl]-4-(11-aminoundecanamido)methylbenzoic acid;
N'-[N-(3β-Hydroxy-20(29)-lupen-28-oyl)-8-aminooctanoyl]-2-aminoisobutyric acid;
(2-R,S)-N'-[N-(3β-Hydroxy-20(29)-lupen-28-oyl)-8-aminooctanoyl]-5-hydroxy-2 -piperidinecarboxylic acid;
N'-[N-(3β-Hydroxy-20(29)-lupen-28-oyl)-8-aminooctanoyl]-3-aminobenzoic acid;
N'-[N-[3β-Hydroxy-20(29)-lupen-28-oyl]-8-aminooctanoyl]-2-aminobenzoic acid;
N'-[N-[3β-Hydroxy-20(29)-lupen-28-oyl]-8aminooctanoyl] -4-aminobenzoic acid;
N'-[N-(3β-Hydroxy-20(29)-lupen-28-oyl)-8aminooctanoyl] -3-(R,S)-amino-3-phenylpropionic acid;
(2-R,S)-N'-[N-(3β-Hydroxy-20(29)-lupen-28-oyl)-8-aminooctanoyl]-3-aminoisobutyric acid;
(3-R,S)-N'-[N-(3β-Hydroxy-20(29)-lupen-28-oyl)-8-aminooctanoyl]-3-aminobutyric acid;
N'-[N-(3β-Hydroxy-20(29)-lupen-28-oyl)-8aminooctanoyl] -N'-hydroxycarbonylethylpropionic acid;
N'-[N-[3β-Hydroxy-20(29)-lupen-28-oyl]-8aminooctanoyl] -trans-4-hydroxy-L-proline;
N'-[N-[3β-Hydroxy-20(29)-lupen-28-oyl]-9aminononanoyl]glycine;
N'-[N-[3β-Hydroxy-20(29)-lupen-28-oyl]-8aminooctanoyl] nipecotic acid;
(4S)-N'-[N-[3β-Hydroxy-20(29)-lupen-28-oyl]-8-aminooctanoyl]-4-amino-6 -methylheptanoic acid;
(3S,4S)-N'-[N-[3β-Hydroxy-20(29)-lupen-28-oyl]-8aminooctanoyl]-4 -amino-5-phenyl-3-hydroxypentanoic acid;
2-[N-[3β-Hydroxy-20(29)-lupen-28-oyl]-7-aminoheptylcarbamoyl]-2(R)-propionic acid;
2-[N-[3β-Hydroxy-20(29)-lupen-28-oyl]-7-aminoheptylcarbamoyl]-2(S)-propionic acid;
2-[N-[3β-Hydroxy-20(29)-lupen-28-oyl]-7-aminoheptylcarbamoyl]-2(R,S)-propionic acid;
2-[N-[3β-Hydroxy-20(29)-lupen-28-oyl]-7-aminoheptylcarbamoyl]-2,2-dimethylacetic acid;
2-[N-[3β-Hydroxy-20(29)-lupen-28-oyl]-7-aminoheptylcarbamoyl]-2(R)-benzylacetic acid;
2-[N-[3β-Hydroxy-20(29)-lupen-28-oyl]-7-aminoheptylcarbamoyl]-2(S)-benzylacetic acid;
2-[N-[3β-Hydroxy-20(29)-lupen-28-oyl]-7-aminoheptylcarbamoyl]-2(R,S)-benzylacetic acid;
[N-[3β-Hydroxy-30-(2'-hydroxyethyl)thio-20(29)-lupen-28-oyl]-7 -aminoheptylcarbamoyl]acetic acid;
2-[N-[3β-Hydroxy-20(29)-lupen-28-oyl]-7-aminoheptylcarbamoyl]benzoic acid;
3-[N-[3β-Hydroxy-20(29)-lupen-28-oyl]-7-aminoheptylcarbamoyl]benzoic acid;
N'-[N-[3β-Hydroxy-20(29)-lupen-28-oyl]-7-aminoheptylcarbamoyl]benzoic acid;
2-[N-[3β-Hydroxy-20(29)-lupen-28-oyl]-8-aminooctylcarbamoyl]-2(R)-propionic acid;
2-[N-[3β-Hydroxy-20(29)-lupen-28-oyl]-8-aminooctylcarbamoyl]-2(S)-propionic acid;
2-[N-[3β-Hydroxy-20(29)-lupen-28-oyl]-8-aminooctylcarbamoyl]-2,2-dimethylacetic acid;
2-[N-[3β-Hydroxy-20(29)-lupen-28-oyl]-8-aminooctylcarbamoyl]-2(R)-benzylacetic acid;
2-[N-[3β-Hydroxy-20(29)-lupen-28-oyl]-8-aminooctylcarbamoyl]-2(S)-benzylacetic acid;
2-[N-[3β-Hydroxy-20(29)-lupen-28-oyl]-8-aminooctylcarbamoyl]-2(R,S)-benzylacetic acid;
[N-[3b-Hydroxy-30-(2'-hydroxyethyl)thio-20(29)-lupen-28-oyl]-8-aminooctylcarbamoyl] acetic acid;
2-[N-[3b-Hydroxy-20(29)-lupen-28-oyl]-8-aminooctylcarbamoyl]benzoic acid;
3-[N-[3b-Hydroxy-20(29)-lupen-28-oyl]-8-aminooctylcarbamoyl]benzoic acid;
4-[N-[3b-Hydroxy-20(29)-lupen-28-oyl]-8-aminooctylcarbamoyl]benzoic acid.

EXAMPLE 67

4-{N-[3β-Hydroxy-20(29)-lupen-28-oyl]-7-aminoheptylcarbamoyl}-3,3-dimethylbutyric acid is prepared in the following way:

4-{N-[3β-Acetoxy-20(29)-lupen-28-oyl]-7-aminoheptylcarbamoyl}-3,3-dimethylbutyric acid can be obtained by analogy with Example 58 from methyl 4-chloroformyl-3,3-dimethylbutanoate, itself obtained from methyl glutarate (C. Galli et al., J. Org. Chem., 44, 1254–1261 (1979)).

4-{N-[3β-Hydroxy-20(29)-lupen-28-oyl]-7-aminoheptylcarbamoyl}-3,3-dimethylbutyric acid exists in the form of a whitish solid melting at around 140° C.

Infrared spectrum (cm$^{-1}$): 1725, 1635 and 1610.

Proton N.M.R. spectrum (400 MHz, CDCl$_3$, δ in ppm): 0.68(d, 1H, —CH at 5), 0.77(s, 3H, —CH$_3$), 0.82 (s, 3H, —CH$_3$), 0.92 (s, 3H, —CH$_3$), 0.98(s, 6H, twice —CH$_3$), 1.12(s, 6H, twice —CH$_3$), 1.55(t, 1H, —CH at 18), 1.68 (s, 3H, —CH$_3$ at 29), 2,32 and 2.42(s, each 2H, C—C H$_2$CONH— and —CH$_2$COOH), 2.42 (td, 1H, —CH at 13), 3.11 (td, 1H, CH at 19), 3.20 (t, 1H, —CH at 3), 3.20 and 3.30 (m, each 1H, CH$_2$—CH$_2$NHCO—), 3.31 (q, 2H, CH$_2$—CH$_2$NHCO—), 4.60 and 4.73 (s, each 1H, =CH$_2$), 5.68 (t, 1H, —CH$_2$NHCO—), 6.58 (t, 1H, —CH$_2$N HCO—).

EXAMPLE 68

1.23 g of 4-dimethylaminopyridine are added to a solution of 705 mg of 2,2-dimethylglutaric anhydride and 2.97 g of N-(3β-acetoxy-20(29)-lupen-28-oyl)-1,7-diaminoheptane in 70 cm$^3$ of dichloromethane. The solution is stirred at a temperature in the region of 20° C. for 69 hours. After evaporating to dryness under reduced pressure (2.7 kPa) at a temperature in the region of 40° C., the residue is taken up in 150 cm$^3$ of distilled water, acidified to a pH in the region of 2 with N-hydrochloric acid and then extracted by means of 250 cm$^3$ of ethyl acetate. The combined organic phases are dried over magnesium sulphate and concentrated to dryness under reduced pressure (2.7 kPa) at a temperature in the region of 40° C. The residue obtained (4.1 g) is chromatographed on a silica column (0.02–0.045 mm) eluted with a 92/8(by volume) mixture of dichloromethane and methanol. The fractions containing the product are combined and concentrated under reduced pressure (2.7 kPa) at a temperature in the region of 40° C. There are thus obtained 760 mg of methyl 4-[N-[3β-acetoxy-20(29)-lupen-28-oyl]-7-aminoheptylcarbamoyl]-2,2-dimethylbutanoate in the form of a white foam (R$_f$=0.37; silica thin layer chromatography; eluent: 24/6/1 by volume chloroform/methanol/aqueous ammonia).

1.6 cm$^3$ of 1N sodium hydroxide solution are added over approximately 10 minutes to a solution of 470 mg of methyl 4-[N-[3β-acetoxy-20(29)-lupen-28-oyl]-7-aminoheptylcarbamoyl]-2,2-dimethylbutanoate in 17 cm$^3$ of methanol and 17 cm$^3$ of tetrahydrofuran and the reaction mixture is stirred for 142 hours at a temperature in the region of 20° C. The reaction mixture is acidified to a pH in the region of 2 using concentrated hydrochloric acid. After stirring for 90 minutes, 68 cm$^3$ of distilled water and 40 cm$^3$ of ethyl acetate are added. The organic phase is separated by settling. The aqueous phase is extracted twice with 40 cm$^3$ of ethyl acetate. The combined organic phases are washed, dried over magnesium sulphate and then concentrated under reduced pressure (2.7 kPa) at a temperature in the region of 40° C. The residue obtained (400 mg) is chromatographed on a silica column (0.02–0.045 mm) eluted with a 48/6/1 by volume mixture of chloroform/methanol/aqueous ammonia. The fractions containing the product are combined and concentrated under reduced pressure (2.7 kPa) at a temperature in the region of 40° C. There are thus obtained 212 mg (48%) of 4-[N-[3β-hydroxy-20 (29)-lupen-28-oyl]-7-aminoheptylcarbamoyl]-2,2-dimethylbutyric acid in the form of a white foam melting at a temperature in the region of 139° C.

N-(3β-acetoxy-20(29)-lupen-28-oyl)-1,7-diaminoheptane can be obtained as in Example 67.

EXAMPLE 69

By carrying out the reaction by analogy with Example 67, 4-[N-[3β-hydroxy-20(29)-lupen-28-oyl]-6-aminohexylcarbamoyl]-3,3-dimethylbutyric acid was prepared from N-(3β-acetoxy-20(29)-lupen-28-oyl)-1,6-diaminohexane and 3,3-dimethylglutaric acid monomethyl ester, M.p.=136° C., (46.6%).

N-(3β-Acetoxy-20(29)-lupen-28-oyl)-1,6-diaminohexane can be obtained by analogy with N-(3β-acetoxy-20(29)-lupen-28 -oyl)-1,7-diaminoheptane, starting from 3β-acetoxy-20(29)-lupen-28-oic acid and 1,6-diaminohexane (see Example 67).

EXAMPLE 70

By carrying out the reaction by analogy with Example 67, 4-[N-methyl-7-(3β-hydroxy-20(29)-lupen-28 -oylamino)heptylcarbamoyl]-3,3-dimethylbutyric acid was prepared from N-methyl-N'-(3β-acetoxy-20(29)-lupen-28-oyl)-1,7-diaminoheptane and 3,3-dimethylglutaric acid monomethyl ester, M.p.=117° C., (40.5%).

N-Methyl-N'-(3β-acetoxy-20(29)-lupen-28-oyl)-1,7-diaminoheptane can be obtained in the following way:

A solution of 28.7 g of N-(3β-acetoxy-20(29)-lupen-28-oyl)-1,7-diaminoheptane in 50 cm$^3$ of dichloromethane and then, over approximately 15 minutes, 6.6 cm$^3$ of triethylamine are added to a solution of 15.2 g of N-methyl-2-methylthiobenzothiazolium iodide in 300 cm$^3$ of dichloromethane. The solution is stirred at a temperature in the region of 20° C. for 2 hours and then the reaction mixture is concentrated at atmospheric pressure at a temperature in the region of 60° C. 150 cm$^3$ of methyl iodide are added to the oil obtained (35.6 g) and the reaction mixture is brought for 30 hours to a temperature in the region of reflux. The reaction mixture is concentrated under reduced pressure (2.7 kPa) at a temperature in the region of 50° C. The oily residue is taken up in 300 cm$^3$ of diethyl ether and triturated. There are thus obtained 39.8 g of an orange-coloured solid which is dissolved in 100 cm$^3$ of dichloromethane. 4.3 cm$^3$ of n-butylamine are added to the solution obtained. The reaction mixture is stirred for 4 hours at a temperature in the region of 25° C., then diluted with 300 cm$^3$ of dichloromethane and washed with 450 cm$^3$ of distilled water. The organic phase is then dried over magnesium sulphate and concentrated to dryness under reduced pressure (2.7 kPa) at a temperature in the region of 40° C. The residue obtained is chromatographed on a silica column (0.02–0.045 mm) eluted with a 19/1 (by volume) mixture of dichloromethane and methanol. The fractions containing the product are combined and concentrated under reduced pressure (2.7 kPa) at a temperature in the region of 40° C. There are thus obtained 7.1 g (26%) of N-methyl-N'-(3β-acetoxy-20(29)-lupen-28-oyl)-1,7-diaminoheptane in the form of a white foam, M.p.=158° C.

EXAMPLE 71

1 cm$^3$ of triethylamine and then a solution of 0.3 cm$^3$ of oxalyl chloride in 10 cm$^3$ of dichloromethane are added to a solution of 560 mg of (2R, 2S, 4R, 4S)-2,4-dimethylglutaric acid in 80 cm³ of dichloromethane. After stirring for 12 hours at a temperature in the region of 25° C., a solution of 1.8 g of N-(3β-acetoxy-20(29)-lupen-28 -oyl)-1,7-diaminoheptane in solution in 15 cm³ of dichloromethane is added over 15 min. The solution is stirred at a temperature in the region of 20° C. for 15 hours and then the reaction mixture is washed with 300 cm³ of distilled water. The organic phase is then dried over magnesium sulphate and concentrated to dryness under reduced pressure (2.7 kPa) at a temperature in the region of 40° C. There is thus obtained 1.00 g of (2R, 2S, 4R, 4S)-4-[N-[3β-acetoxy-20(29)-lupen-28 -oyl]-7-aminoheptylcarbamoyl]-2,4-dimethylbutyric acid (45%) in the form of a white foam ($R_f$=0.63; silica thin layer chromatography; eluent: 9/1 by volume dichloromethane/methanol).

12.2 cm³ of 5N sodium hydroxide solution are added over approximately 10 minutes to a solution of 920 mg of (2R, 2S, 4R, 4S)-4-[N-[3β-acetoxy-20(29)-lupen-28-oyl]-7 -aminoheptylcarbamoyl]-2,4-dimethylbutyric acid in 100 cm³ of methanol and the reaction mixture is stirred for 144 hours at a temperature in the region of 20° C. The reaction mixture is acidified to a pH in the region of 2 using concentrated hydrochloric acid. After stirring for half an hour, 100 cm³ of distilled water and 250 cm³ of dichloromethane are added. The organic phase is separated by settling. The aqueous phase is extracted twice with 250 cm³ of dichloromethane. The combined organic phases are washed with 400 cm³ in total of distilled water, dried over magnesium sulphate and then concentrated under reduced pressure (2.7 kPa) at a temperature in the region of 40° C. The solid obtained (950 mg) is taken up in 5 cm³ of acetonitrile, then filtered and dried under reduced pressure (2 kPa) at a temperature in the region of 40° C. There are thus obtained 480 mg of (2R, 2S, 4R, 4S)-4-[N-[3β-hydroxy-20(29)-lupen-28 -oyl]-7-aminoheptylcarbamoyl]-2,4-dimethylbutyric acid (50%) in the form of a white solid melting at a temperature in the region of 117° C.

N-(3β-Acetoxy-20(29)-lupen-28-oyl)-1,7-diaminoheptane can be obtained as described above in Example 67.

EXAMPLE 72

By carrying out the reaction by analogy with Example 67, 4-[N-[3β-hydroxy-20(29)-lupen-28-oyl]-8 -aminooctanylcarbamoyl]-3,3-dimethylbutyric acid was prepared from N-(3β-acetoxy-20(29)-lupen-28-oyl)-1,8-diaminooctane and 3,3-dimethylglutaric acid monomethyl ester, M.p.=135° C. (41.3%).

N-(3β-Acetoxy-20(29)-lupen-28-oyl)-1,8-diaminooctane can be obtained by analogy with N-(3β-acetoxy-20(29)-lupen-28-oyl)-1,7-diaminoheptane (Example 67), starting from 3β-acetoxy-20(29)-lupen-28-oic acid and 1,8-diaminooctane.

EXAMPLE 73

By carrying out the reaction by analogy with Example 67, 4'-{N-[3β-hydroxy-20(29)-lupen-28-oyl]-7-aminoheptylcarbamoyl}-2,2 -dimethylphenylacetic acid was prepared from 3β-acetoxy-20(29)-lupen-28-oyl)-1,7-diaminoheptane and 2,2-dimethyl-4'-(methoxycarbonyl)phenylacetic acid, M.p.=123° C. (35.6%).

2,2-Dimethyl -4'-(methoxycarbonyl)phenylacetic acid can be prepared in the following way.

1.88 cm³ of an 86% aqueous potassium hydroxide solution are added to a solution of 4.2 g of methyl 2,2-dimethyl-4'-(methoxycarbonyl)phenylacetate in 37 cm³ of methanol and the reaction mixture is heated for 12 hours at a temperature in the region of reflux. The reaction mixture is evaporated to dryness under reduced pressure (2.7 kPa) at a temperature in the region of 40° C. 50 cm³ of distilled water and 50 cm³ of dichloromethane are added to the solid residue obtained. The organic phase is separated by settling. The aqueous phase is extracted twice with 50 cm³ of dichloromethane. The combined organic phases are washed with 50 cm³ in total of distilled water, dried over magnesium sulphate and then concentrated under reduced pressure (2.7 kPa) at a temperature in the region of 40° C. The residue obtained (1.24 g) is chromatographed on a silica column (0.02–0.045 mm) eluted with a 99/1 (by volume) mixture of ethyl acetate and ethanol. The fractions containing the product are combined and concentrated under reduced pressure (2.7 kPa) at a temperature in the region of 40° C. There are thus obtained 490 mg of 2,2-dimethyl-4'-(methoxycarbonyl)phenylacetic acid (12.5%) in the form of a brown solid ($R_f$=0.76; silica thin layer chromatography; eluent: 19/1 by volume ethyl acetate/ethanol).

Methyl 2,2-dimethyl-4'-(methoxycarbonyl)phenylacetate can be obtained in the following way. 2 cm³ of methyl iodide are added to a suspension of 3 g of 2,2-dimethyl-4'-carboxyphenylacetic acid and 4.34 g of potassium carbonate in 30 cm³ of dimethylformamide. The reaction medium is stirred at a temperature in the region of 20° C. for 15 hours, the reaction mixture is then poured into 50 cm³ of distilled water and then extracted with 150 cm³ of diethyl ether. The organic phase is then dried over magnesium sulphate and concentrated to dryness under reduced pressure (2.7 kPa) at a temperature in the region of 40° C. The yellow oil obtained (3.30 g) is used without additional purification. ($R_f$=0.87; silica thin layer chromatography; eluent: ethyl acetate).

2,2-Dimethyl-4'-carboxyphenylacetic acid can be obtained according to J. Colonge and L. Pichat, Bull. Soc. Chim. France, (1949) 177–85.

EXAMPLE 74

(4R)-N-{N-[3β-Hydroxy-20(29)-lupen-28-oyl]-8 -aminooctanoyl}-4-amino-6-methylheptanoic acid can be obtained by analogy with Example 27 from methyl (4R)-4-amino-6-methylheptanoate hydrochloride. (4R)-N-{N[3β-Hydroxy-20 (29)-lupen-28-oyl]-8-aminooctanoyl}-4-amino-6-methylheptanoic acid exists in the form of a white solid melting at around 120° C. (Y=83%).

Methyl (4R)-4-amino-6-methylheptanoate hydrochloride can be obtained in the following way:

0.22 cm³ of thionyl chloride is added, at a temperature in the region of –70° C., to a solution of 490 mg of (4R)-4-amino-6-methylheptanoic acid (which can be prepared according to A. P. Craven, H. J. Dyke and E. J. Thomas, Tetrahedron, 45(8), 2417(1989)) in 8 cm³ of methanol. Stirring is maintained for 5 hours at a temperature in the region of 20° C. The solvent is removed under reduced pressure (2.7 kPa) at a temperature in the region of 35° C. There are thus obtained 520 mg of methyl (4R)-4-amino-6-methylheptanoate hydrochloride, in the form of a white solid melting at around 134° C.

EXAMPLE 75

(RS)-4-[N-[3β-hydroxy-20(29)-lupen-28-oyl]-7 -aminoheptylcarbamoyl]-3-ethyl-3-methylbutyric acid.

By carrying out the reaction by analogy with Example 67, (RS)-4-[N-[3β-hydroxy-20(29)-lupen-28-oyl]-7 -aminoheptylcarbamoyl]-3-ethyl-3-methylbutyric acid was prepared from N-(3β-acetoxy-20(29)-lupen-28-oyl)-1,7-diaminoheptane and 3-methyl-3-ethylglutaric acid monomethyl ester, M.p.=178° C., (Y=84%).

3-Methyl-3-ethylglutaric acid monomethyl ester can be prepared according to N. Rabjohn and H. H. Farmer, J. Org. Chem., 24, 359–62(1959).

EXAMPLE 76

4-[N-[3-Oxo-20(29)-lupen-28-oyl]-7-aminoheptylcarbamoyl]-3,3-dimethylbutyric acid:

By carrying out the reaction by analogy with Example 67, 4-[N-[3-oxo-20(29)-lupen-28-oyl]-7-aminoheptylcarbamoyl]-3,3-dimethylbutyric acid was prepared from N-(3-oxo-20(29)-lupen-28-oyl)-1,7-diaminoheptane and 3,3-dimethylglutaric acid monomethyl ester, M.p.=135°–140° C., (Y=21%).

N-(3-Oxo-20(29)-lupen-28-oyl)-1,7-diaminoheptane was prepared by analogy with N-(3β-acetoxy-20(29)-lupen-28-oyl)-1,7-diaminoheptane (Example 67) from 3-oxo-20(29)-lupen-28-oyl chloride (described in Example 8) and 1,7-diaminoheptane, (Y=75%; $R_f$=0.65; silica thin layer chromatography; eluent: 12/3/0.5 (by volume) chloroform/methanol/20% aqueous ammonia).

EXAMPLE 77

(RS)-4-[N-[3β-Hydroxy-20(29)-lupen-28-oyl]-7-aminoheptylcarbamoyl]-3-phenylbutyric acid:

By carrying out the reaction by analogy with Example 71, (RS)-4-[N-[3β-hydroxy-20(29)-lupen-28-oyl]-7-aminoheptylcarbamoyl]-3-phenylbutyric acid was prepared from N-(3β-hydroxy-20(29)-lupen-28-oyl)-1,7-diaminoheptane and (RS)-3-phenylglutaric acid, M.p.=160° C., (Y=86%).

The present invention also relates to the pharmaceutical compositions containing at least one product of general formula (I), optionally in the salt form, in the pure state or in the form of a combination with one or more compatible and pharmaceutically acceptable diluents or adjuvants, or with another agent intended for the treatment of AIDS, an antiviral, immunomodulating or antimicrobial agent.

The composition according to the invention is capable of keeping alive cells infected with an HIV virus and thus of reducing the progression towards AIDS or reducing its seriousness in subjects who are already infected by reducing the mortality of infected cells. The compositions can be used orally, parenterally or rectally.

The compositions can be used as curative or preventive compositions in subjects who are immunodeficient and/or who are infected with an HIV virus. Of course, the constitution of these compositions will be suited to the particular case of the digestive tract of the immunodepressed subjects.

It is possible to use, as solid compositions for oral administration, tablets, pills, gelatin capsules, powders or granules. In these compositions, the active product according to the invention is mixed with one or more inert diluents or adjuvants, such as sucrose, lactose or starch.

These compositions can comprise substances other than the diluents, for example a lubricating agent such as magnesium stearate or a coating intended for a controlled release.

It is possible to use, as liquid compositions for oral administration, pharmaceutically acceptable solutions, suspensions, emulsions, syrups and elixirs containing inert diluents such as water or paraffin oil. These compositions can also comprise substances other than the diluents, for example wetting, sweetening or flavouring products.

The compositions for parenteral administration can be sterile solutions or emulsions. It is possible to use, as solvent or vehicle, propylene glycol, a polyethylene glycol, vegetable oils, in particular olive oil, or injectable organic esters, for example ethyl oleate.

These compositions can also contain adjuvants, in particular wetting, isotonicity, emulsifying, dispersing and stabilising agents.

Sterilisation can be carried out in several ways, for example by using a bacteriological filter, by irradiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

In human therapy, the doctor will determine the dose which he considers the most appropriate as a function of a preventive or curative treatment, as a function of age, weight, degree of the infection and other factors inherent to the subject to be treated. Generally, the doses are of between 10 and 100 mg/kg intravenously for an adult.

The present invention also relates to the combinations consisting of one or more lupane derivatives of general formula (I), and/or, if appropriate, their salts, and another active principle known for its anti-retrovirus activity, optionally in the presence of pharmaceutically acceptable excipients.

The anti-retrovirus agents which can be combined are chosen from agents which are compatible and inert with respect to the lupane derivative of general formula (I). In a non-limiting fashion, these agents are chosen from reverse transcriptase inhibitors [zidovudine (AZT), didanosine (DDI), dideoxycytidine (DDC), TIBO, nevirapine, PMEA, KEPT and the like], from protease inhibitors [such as, for example, A 77003] or from tat protein inhibitors [such as, for example, RO 24-7429].

The following example illustrates a composition according to the invention.

EXAMPLE

Phials are prepared containing a solution containing a measured charge of 10 mg of N-[3β-hydroxy-20(29)-lupen-28-oyl]-11-aminoundecanoic acid by adding 2% of glycine and 0.1% of cysteine to 500 cm³ of a 0.2% solution of N-[3β-hydroxy-20(29)-lupen-28-oyl]-11-aminoundecanoic acid in the isotonic phosphate buffer. The solution is split up and distributed aseptically in phials. Each phial contains 10 mg of active product.

We claim:

1. New lupane derivative of general formula:

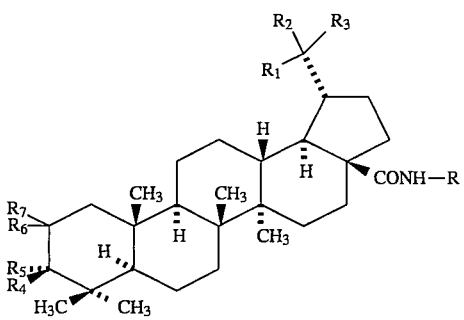

in which:
R represents a radical of general formula:

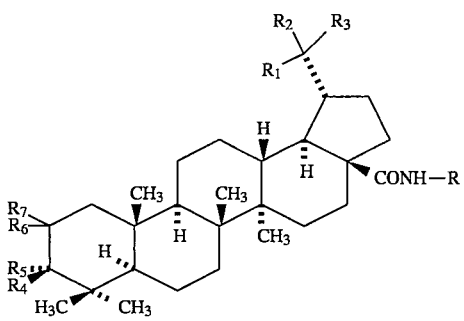
(I)

in which R' and R", which are identical or different, are hydrogen atoms or alkyl radicals, X is a bond or represents a carbamoyl, N-methylcarbamoyl, aminocarbonyl or N-methylaminocarbonyl radical, Y is a bond or represents a phenylene radical, $R^o$ and $R^{oo}$, which are identical or different, are hydrogen atoms or alkyl radicals (it being understood that $R^o$ and $R^{oo}$ are not necessarily identical on each unit —$CR^oR^{oo}$—), or $R^o$ is hydroxyl, hydroxyalkyl, phenyl, benzyl, carbamoylmethyl or else, when Y is a bond and X is carbamoyl, $R^o$ can form a 5- or 6-membered ring with the nitrogen atom contained in X, it being possible for this ring to additionally comprise another hetero atom chosen from oxygen or sulphur and, n, m and p are integers from 0 to 16 such that m+n+p is between 4 and 16, $R_1$ is a methyl radical, or forms, with $R_3$, a methylene radical or an oxo radical, $R_2$ is a hydroxyl, methyl or hydroxymethyl radical or a radical —$CH_2OR'_2$, —$CH_2SR'_2$ or —$CH_2NHR'_2$ for which $R'_2$ is alkyl, hydroxyalkyl, dihydroxyalkyl, acetamidoalkyl or acetyl, or $R_2$ is an amino radical substituted with a hydroxyalkyl or carboxyhydroxyalkyl radical, or a dialkylamino radical, the alkyl parts of which can form, with the nitrogen atom to which they are joined, a 5- or 6-membered heterocycle optionally containing another hetero atom chosen from oxygen, sulphur or nitrogen and, optionally, N-alkyl, $R_3$ is a hydrogen atom or forms, with $R_1$ or $R_2$, a methylene radical or an oxo radical, $R_4$ and $R_5$ are different and represent a hydrogen atom or a hydroxyl radical, or together form an oxo, hydroxyimino or optionally substituted (with a carboxyl or dialkylamino radical, the alkyl parts of which can form, with the nitrogen atom to which they are joined, a 5- or 6-membered heterocycle optionally containing another hetero atom chosen from oxygen, nitrogen or sulphur and optionally substituted with an alkyl radical) alkyloxyimino radical and $R_6$ and $R_7$ are hydrogen atoms, or else $R_4$ and $R_5$, and $R_6$ and $R_7$ together form oxo radicals, it being understood that the alkyl radicals are straight or branched and contain 1 to 4 carbon atoms, as well as their salts when they exist.

2. New lupane derivative according to claim 1, for which:
R represents a radical of general formula:

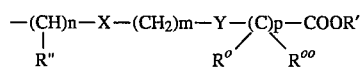

in which R' and R", which are identical or different, are hydrogen atoms or alkyl radicals, X is a bond or represents a carbamoyl, N-methylcarbamoyl or aminocarbonyl radical, Y is a bond or represents a phenylene radical, $R^o$ and $R^{oo}$, which are identical or different, are hydrogen atoms or alkyl radicals (it being understood that $R^o$ and $R^{oo}$ are not necessarily identical on each unit —$CR^oR^{oo}$—), or $R^o$ is hydroxyl, hydroxyalkyl, phenyl, benzyl, carbamoylmethyl or else, when Y is a bond and X is carbamoyl, $R^o$ can form a 5- or 6-membered ring with the nitrogen atom contained in X and, n, m and p are integers from 0 to 16 such that m+n+p is between 4 and 16, $R_1$ is a methyl radical, or forms, with $R_3$, a methylene radical or an oxo radical, $R_2$ is a hydroxyl, methyl or hydroxymethyl radical or a radical —$CH_2SR'_2$ or —$CH_2NHR'_2$ for which $R'_2$ is alkyl, hydroxyalkyl, acetamidoalkyl or acetyl, or $R_2$ is an amino radical substituted with a hydroxyalkyl or carboxyhydroxyalkyl radical, or a dialkylamino radical, the alkyl parts of which can form, with the nitrogen atom to which they are joined, a 5- or 6-membered heterocycle optionally containing another nitrogen atom and optionally N-methylated, $R_3$ is a hydrogen atom or forms, with $R_1$ or $R_2$, a methylene radical or an oxo radical, $R_4$ and $R_5$ are different and represent a hydrogen atom or a hydroxyl radical, or together form an oxo, or optionally substituted (with a carboxyl or dialkylamino radical, the alkyl parts of which can form, with the nitrogen atom to which they are joined, a 5- or 6-membered heterocycle optionally containing another nitrogen atom optionally substituted by a methyl radical) alkyloxyimino radical and $R_6$ and $R_7$ are hydrogen atoms, or else $R_4$ and $R_5$, and $R_6$ and $R_7$, together form oxo radicals, it being understood that the alkyl radicals are straight or branched and contain 1 to 4 carbon atoms, as well as their salts when they exist.

3. A lupane derivative according to claim 1, characterized in that it is N'-[N-[3β-hydroxy-20(29)-lupen-28 -oyl]-8-aminooctanoyl]-β-alanine.

4. A lupane derivative according to claim 1, characterized in that it is N'-[N-[3β-hydroxy-20(29)-lupen-28 -oyl]-8-aminooctanoyl]-L-alanine.

5. A lupane derivative according to claim 1, characterized in that it is N'-[N-[3β-hydroxy-20(29)-lupen-28-oyl]-8-aminooctanoyl]-L-threonine.

6. A lupane derivative according to claim 1, characterized in that it is N'-[N-[3β-hydroxy-20(29)-lupen-28-oyl]-8-aminooctanoyl]-L-statine.

7. A lupane derivative according to claim 1, characterized in that it is N-[3β-hydroxy-20(29)-lupen-28-oyl]-7-aminoheptylcarbamoylacetic acid.

8. Pharmaceutical composition, characterised in that it contains at least one product according to claim 1, in the pure state or in combination with any compatible and pharmaceutically acceptable diluent or adjuvant and/or in combination with another antiviral, immunomodulating or antimicrobial active principle.

* * * * *

UNITED STATES PATENT AND TRADEMARK OFFICE
CERTIFICATE OF CORRECTION

PATENT NO. : 5,468,888
DATED : Nov. 21, 1995
INVENTOR(S) : Romaine Bouboutou, et.al.

It is certified that error appears in the above—identified patent and that said Letters Patent is hereby corrected as shown below:

On the Title page, before Item
"[51] Int. Cl.":

Please insert:

--[30]     Foreign Application Priority Data

November 13, 1991 [FR]     France     9113907--

Signed and Sealed this

Ninth Day of July, 1996

Attest:

BRUCE LEHMAN

Attesting Officer        Commissioner of Patents and Trademarks